(12) United States Patent
Vozone et al.

(10) Patent No.: US 11,596,641 B2
(45) Date of Patent: *Mar. 7, 2023

(54) METHODS AND COMPOSITIONS FOR TREATING MEIBOMIAN GLAND DYSFUNCTION

(71) Applicant: Hovione Scientia Limited, Cork (IE)

(72) Inventors: Carla Maria Dos Santos Vozone, East Windsor, NJ (US); Mohammad Salman, East Windsor, NJ (US); George Nathaniel Magrath, III, Mount Pleasant, SC (US); Courtney Rouse Smith, Gainesville, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/307,275

(22) Filed: May 4, 2021

(65) Prior Publication Data

US 2021/0299149 A1 Sep. 30, 2021

Related U.S. Application Data

(63) Continuation of application No. 17/210,648, filed on Mar. 24, 2021.

(60) Provisional application No. 63/106,657, filed on Oct. 28, 2020, provisional application No. 62/993,827, filed on Mar. 24, 2020.

(51) Int. Cl.
| | | |
|---|---|---|
| *A61K 31/65* | (2006.01) | |
| *A61P 27/02* | (2006.01) | |
| *A61K 9/00* | (2006.01) | |
| *A61K 9/06* | (2006.01) | |
| *A61K 9/10* | (2006.01) | |
| *A61K 9/14* | (2006.01) | |
| *A61K 47/06* | (2006.01) | |
| *A61K 47/32* | (2006.01) | |

(52) U.S. Cl.
CPC ............ *A61K 31/65* (2013.01); *A61K 9/0014* (2013.01); *A61K 9/0048* (2013.01); *A61K 9/06* (2013.01); *A61K 9/10* (2013.01); *A61K 9/14* (2013.01); *A61K 47/06* (2013.01); *A61K 47/32* (2013.01); *A61P 27/02* (2018.01)

(58) Field of Classification Search
CPC .... A61K 31/65; A61K 9/0014; A61K 9/0048; A61K 9/06; A61K 9/10; A61K 9/14; A61K 47/06; A61K 47/32; A61P 27/02
See application file for complete search history.

(56) References Cited

U.S. PATENT DOCUMENTS

| | | |
|---|---|---|
| 8,258,327 B2 | 9/2012 | Marto et al. |
| 8,268,804 B2 | 9/2012 | Wortzman et al. |
| 8,614,178 B2 | 12/2013 | Theisinger et al. |
| 8,748,402 B2 | 6/2014 | Abelson et al. |
| 9,592,246 B2 | 3/2017 | Salman et al. |
| 9,877,975 B2 | 1/2018 | Tsubota et al. |
| 9,999,594 B2 | 6/2018 | Kido et al. |
| 10,179,160 B2 | 1/2019 | Dana et al. |
| 10,213,443 B2 | 2/2019 | Salman et al. |
| 10,350,223 B2 | 7/2019 | Yee et al. |
| 10,653,707 B2 | 5/2020 | Mansouri |
| 10,772,899 B2 | 9/2020 | Alster et al. |
| 10,849,847 B2 | 12/2020 | Tamarkin et al. |
| 2009/0136514 A1 | 5/2009 | Power |
| 2011/0121033 A1* | 5/2011 | Horne ............. A61P 17/10 222/145.1 |
| 2012/0028929 A1 | 2/2012 | Power et al. |
| 2012/0093876 A1* | 4/2012 | Ousler, III ........ A61K 31/65 424/400 |
| 2017/0182071 A1 | 6/2017 | Salman et al. |
| 2018/0064638 A1 | 3/2018 | Tamarkin et al. |
| 2020/0030268 A1 | 1/2020 | Amselem et al. |

FOREIGN PATENT DOCUMENTS

| | | |
|---|---|---|
| WO | WO-2009025763 A2 | 2/2009 |
| WO | WO-2012051313 A2 | 4/2012 |
| WO | WO-2015163821 A1 | 10/2015 |
| WO | WO-2018212955 A1 | 11/2018 |
| WO | WO-2019245382 A1 | 12/2019 |

OTHER PUBLICATIONS

Aronowicz, J.D. et al. in *Br. J. Ophthalmol.* (2006) vol. 90(7), pp. 856-860.
Clinicaltrials Publication for Study NCT 03888378, available from clinicaltrials.gov online on Mar. 25, 2019.
Clinicaltrials Publication for Study NCT 03888378, available from clinicaltrials.gov online on Apr. 24, 2019.
Clinicaltrials Publication for Study NCT 03263273, available from clinicaltrials.gov online on Nov. 5, 2018.
Clinicaltrials Publication for Study NCT 03263273, available from clinicaltrials.gov online on Nov. 8, 2019.
Fu, J. et al. in *Medicine* (2019) vol. 98(31), e16547.
"Oral minocycline appears beneficial in meibomian gland dysfunction" in *American Journal of Ophthalmology* (Dec. 2012).
Park, C. et al. in *Br. J. Ophthalmol.* (2002) vol. 86(11), pp. 1313-1314.
Webster, G. et al. in *Br. J. Dermatol.* (2020) vol. 183(3), pp. 471-479.

(Continued)

*Primary Examiner* — Genevieve S Alley
(74) *Attorney, Agent, or Firm* — Dechert LLP

(57) ABSTRACT

The invention provides methods, compositions, and kits containing a minocycline topical suspension, for treating meibomian gland dysfunction and related disorders.

22 Claims, 21 Drawing Sheets

(56) References Cited

OTHER PUBLICATIONS

International Search Report and Written Opinion for International Patent Application No. PCT/EP2021/057565, dated Jul. 23, 2021, 13 pages.
U.S. Appl. No. 17/210,648, Methods and Compositions for Treating Meibomian Gland Dysfunction, filed Mar. 24, 2021.
U.S. Appl. No. 17/412,328, Methods and Compositions for Treating Rosacea, filed Aug. 26, 2021.

* cited by examiner

METHODS AND COMPOSITIONS FOR TREATING MEIBOMIAN GLAND DYSFUNCTION

CROSS-REFERENCE TO RELATED APPLICATIONS

This application is a continuation of U.S. patent application Ser. No. 17/210,648, filed Mar. 24, 2021, which claims the benefit of and priority to U.S. Provisional Patent Application Ser. No. 63/106,657, filed Oct. 28, 2020 and U.S. Provisional Patent Application Ser. No. 62/993,827, filed Mar. 24, 2020; the contents of each of which are hereby incorporated by reference in their entirety.

FIELD OF THE INVENTION

The invention provides methods, compositions, and kits containing a minocycline topical suspension, for treating meibomian gland dysfunction and related disorders.

BACKGROUND

Functioning meibomian glands play a critical role in maintaining optimal ocular surface conditions. One common disorder observed in patients by eye care professionals, including ophthalmologists and optometrists, is meibomian gland dysfunction. Meibomian gland dysfunction typically features meibomian glands that either hyposecrete or are obstructed. Meibomian gland dysfunction has historically been treated on a chronic basis through either mechanical therapy (e.g., eyelid hygiene, eyelid massage, or eyelid compression/expression) alone or in combination with topical or systemic antibiotics or topical immunosuppressants such as steroids or cyclosporine. The need exists for meibomian gland dysfunction therapies that are more effective and/or have reduced adverse side effects.

Minocycline crystal forms, formulations of minocycline, and medical uses of the foregoing have been described in, for example, U.S. Pat. Nos. 8,258,327; 9,592,246; and 10,213,443. Oral administration of minocycline to human patients has been described in the *American Journal of Ophthalmology* (December 2012). However, oral administration of minocycline raises the risk of adverse side effects due to systemic exposure to minocycline.

The present invention addresses the need for improved therapies for meibomian gland dysfunction and provides other related advantages.

SUMMARY

The invention provides methods, compositions, and kits containing a minocycline topical suspension, for treating meibomian gland dysfunction and related disorders. The minocycline topical suspension is preferably topically administered to the eyelid margin of the patient's eye. Since administering too large a dose of minocycline topical suspension can result in the undesired side effects (e.g., the patient experiencing eye irritation, the patient experiencing a sensation of grit in the eye due to minocycline topical suspension migrating onto the surface of the eye, blurry vision due to minocycline topical suspension migrating onto the surface of the eye, and/or the patient temporarily experiencing a yellow hue to their vision in the effected eye due to the presence of minocycline on the surface of the eye), it is important to administer a dose of minocycline that avoids the foregoing side effects and use a formulation that minimizes the foregoing side effects, while also providing sufficient minocycline to the appropriate tissue in order to achieve a therapeutic effect against meibomian gland dysfunction. The method described herein comprising topically administering minocycline topical suspension to the eyelid margin of a patient treats meibomian gland dysfunction while minimizing the occurrence of local and systemic adverse side effects. Exemplary aspects and embodiments of the invention are described below.

One aspect of the invention provides a method of treating meibomian gland dysfunction, wherein the method comprises topically administering to the eyelid margin of a patient in need thereof once or twice per day a dose of a minocycline topical suspension to treat the meibomian gland dysfunction, wherein the dose provides from about 0.1 mg to about 1.4 mg of minocycline, and the minocycline topical suspension comprises:
  a) minocycline in a suspended form within the topical suspension;
  b) a liquid medium that dissolves less than 5% (w/w) of the minocycline at room temperature after two hours, wherein the liquid medium contains mineral oil; and
  c) a polymeric hydrocarbon gelling agent;
wherein particles of minocycline in the topical suspension have a D90 particle size less than 8 microns, and the topical suspension comprises from about 0.1% (w/w) to about 2% (w/w) minocycline.

The method may be further characterized according to, for example, the dose of minocycline topical suspension, the frequency of administration of minocycline topical suspension, features of the minocycline topical suspension, patients to receive treatment, and results produced by the method. In certain embodiments, the dose of minocycline topical suspension provides about 0.5 mg of minocycline. In certain embodiments, the dose of minocycline topical suspension is administered twice per day. In certain embodiments, the dose of minocycline topical suspension is administered once per day. In certain embodiments, the patient has an inflamed meibomian gland. In certain embodiments, the patient has resultant or associated dry eye disease. In certain embodiments, the method reduces the patient's vascular engorgement score of at least 1. In certain embodiments, after a duration of at least three months where the patient has received a dose of minocycline topical suspension each day, the patient has a vascular engorgement score of no greater than 1. These and other features are described in more detail herein below.

Also provided are methods for treating blepharitis, meibomitis, and ocular rosacea. The method comprises topically administering to the eye of a patient in need thereof a therapeutically effective amount of a minocycline topical suspension to treat the blepharitis, meibomitis, or ocular rosacea.

Also provided is a minocycline topical suspension for use in treating medical conditions described herein. Such use may employ embodiments described herein for the therapeutic methods, such as the dose of minocycline topical suspension, the frequency of administration of minocycline topical suspension, patients to receive treatment, and results produced by the use.

DETAILED DESCRIPTION OF THE INVENTION

Figure 1:
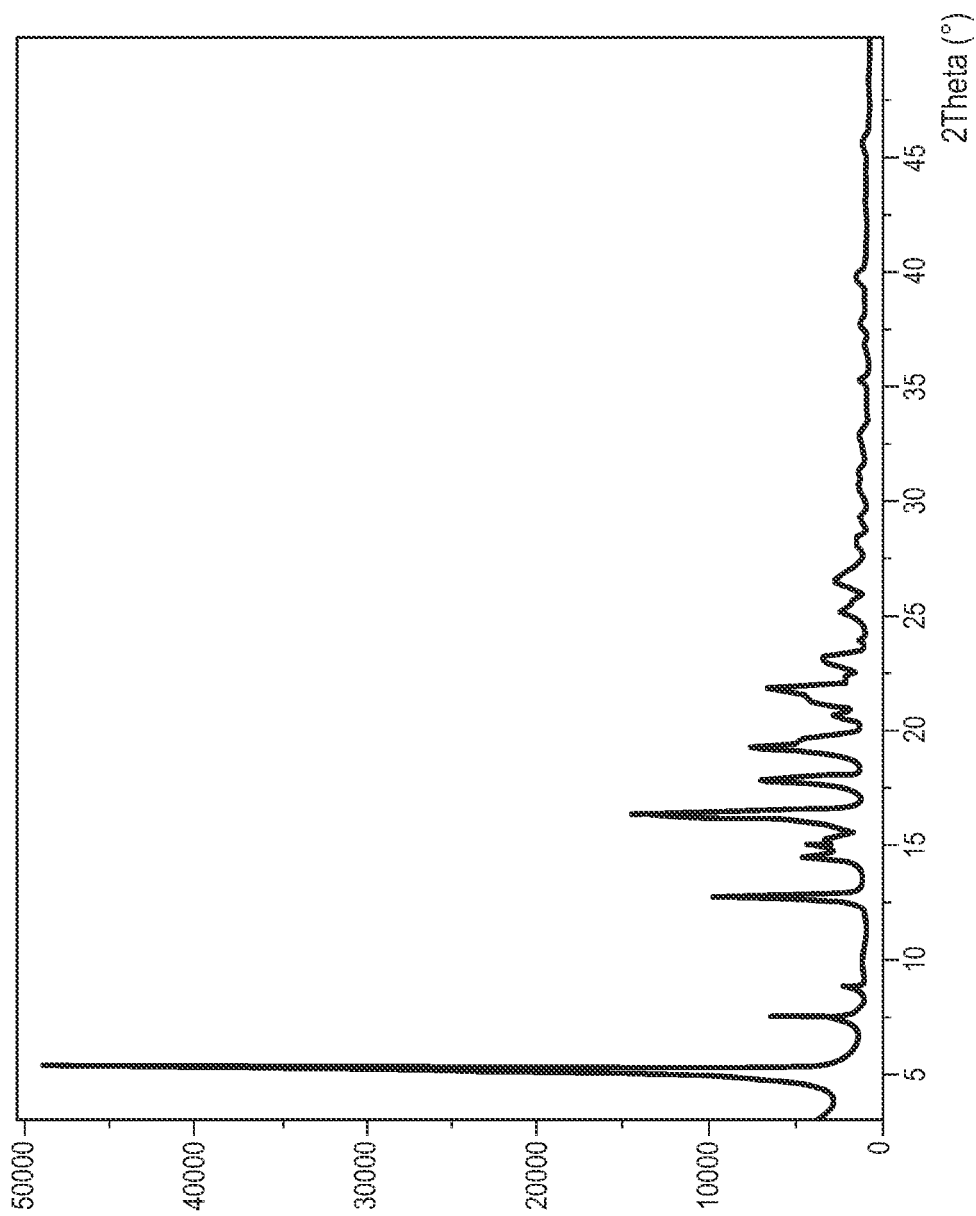
FIG. 1 depicts an X-ray powder diffraction spectrum of crystalline form I of minocycline.

The invention provides methods, compositions, and kits containing a minocycline topical suspension, for treating meibomian gland dysfunction and related disorders. The minocycline topical suspension is preferably topically administered to the eyelid margin of the patient's eye. Since administering too large a dose of minocycline topical suspension can result in the undesired side effects (e.g., the patient experiencing eye irritation, the patient experiencing a sensation of grit in the eye due to minocycline topical suspension migrating onto the surface of the eye, blurry vision due to minocycline topical suspension migrating onto the surface of the eye, and/or the patient temporarily experiencing a yellow hue to their vision in the effected eye due to the presence of minocycline on the surface of the eye), it is important to administer a dose of minocycline that avoids the foregoing side effects and use a formulation that minimizes the foregoing side effects, while also providing sufficient minocycline to the appropriate tissue in order to achieve a therapeutic effect against meibomian gland dysfunction. The method described herein comprising topically administering minocycline topical suspension to the eyelid margin of a patient treats meibomian gland dysfunction while minimizing the occurrence of local and systemic adverse side effects. Various aspects of the invention are set forth below in sections; however, aspects of the invention described in one particular section are not to be limited to any particular section.

Definitions

To facilitate an understanding of the present invention, a number of terms and phrases are defined below.

As used herein, the term "minocycline" refers to a compound having the following chemical structure and tautomers thereof:

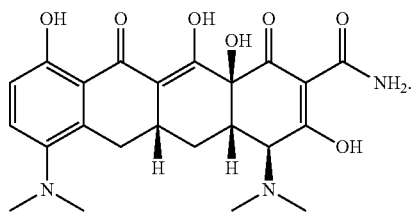 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

The terms "a," "an" and "the" as used herein mean "one or more" and include the plural unless the context is inappropriate.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. Unless specified otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin in Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate (mesylate), 2-naphthalenesulfonate, nicotinate, oxalate, palmoate, pectinate, persulfate, phenylpropionate, picrate, pivalate, propionate, succinate, sulfate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls. Certain numerical values herein are modified by the term about. In certain embodiments, about a stated value is within ±10% of the stated value; also provided are embodiments that are within ±9%, ±8%, ±7%, ±6%, ±5%, ±4%, ±3%, ±2%, or ±1% of the stated value.

I. Therapeutic Methods

The invention provides methods for treating patients suffering from meibomian gland dysfunction by administering minocycline topical suspension to the patient. The invention also provides methods for treating blepharitis, meibomitis, and ocular rosacea by administering minocycline topical suspension to the patient. Various aspects and embodiments of the therapeutic methods are described in the sections below. The sections are arranged for convenience and information in one section is not to be limited to that section, but may be applied to methods in other sections.

A. First Method

One aspect of the invention provides a method of treating meibomian gland dysfunction, wherein the method comprises topically administering to the eyelid margin of a patient in need thereof once or twice per day a dose of a minocycline topical suspension to treat the meibomian gland dysfunction, wherein the dose provides from about 0.1 mg to about 1.4 mg of minocycline, and the minocycline topical suspension comprises:
  a) minocycline in a suspended form within the topical suspension;
  b) a liquid medium that dissolves less than 5% (w/w) of the minocycline at room temperature after two hours, wherein the liquid medium contains mineral oil; and
  c) a polymeric hydrocarbon gelling agent;
  wherein particles of minocycline in the topical suspension have a D90 particle size less than 8 microns, and the topical suspension comprises from about 0.1% (w/w) to about 2% (w/w) minocycline.

B. Second Method

Another aspect of the invention provides a method of treating meibomian gland dysfunction, wherein the method comprises topically administering to the eye of a patient in need thereof a therapeutically effective amount of minocycline to treat the meibomian gland dysfunction. In a more specific embodiment, the invention provides a method of treating meibomian gland dysfunction in a patient having a tear film matrix metalloproteinase-9 (MMP-9) concentration greater than about 40 ng/mL, wherein the method comprises topically administering to the eye of said patient in need thereof a therapeutically effective amount of minocycline to treat the meibomian gland dysfunction. The methods may be further characterized according to additional features. For example, in certain embodiments, the minocycline is in the form of a topical suspension. In certain embodiments, the topical suspension comprises a gelling agent. In certain embodiments, the topical suspension comprises an oil and one or more gelling polymers.

In certain embodiments, the minocycline topical suspension comprises minocycline in a suspended form within the topical suspension. In certain embodiments, particles of minocycline in the topical suspension have a D90 particle size in the range of from about 1 microns to about 10 microns. In certain embodiments, particles of minocycline in the topical suspension have a D90 particle size in the range of from about 1 microns to about 7 microns. In certain embodiments, particles of minocycline in the topical suspension have a D90 particle size in the range of from about 1 microns to about 5 microns. In certain embodiments, particles of minocycline in the topical suspension have a D90 particle size in the range of from about 2 microns to about 4 microns, or from about 3 microns to about 4 microns. In certain embodiments, particles of minocycline in the topical suspension have a D90 particle size less than 8, 7, 6, 5, 4, or 3 microns. In certain embodiments, particles of minocycline in the topical suspension have a D90 particle size less than 5 microns. In certain embodiments, particles of minocycline in the topical suspension have a D90 particle size less than 4 microns.

In certain embodiments, the minocycline topical suspension comprises a liquid medium that dissolves less than 5% (w/w) of the minocycline at room temperature after two hours, wherein the liquid medium contains mineral oil.

In certain embodiments, the minocycline topical suspension comprises a polymeric hydrocarbon gelling agent.

In certain embodiments, the topical suspension comprises from about 0.1% (w/w) to about 2% (w/w) minocycline. In certain embodiments, the topical suspension comprises from about 0.3% (w/w) to about 1% (w/w) minocycline. In certain embodiments, the topical suspension comprises about 0.3% (w/w) minocycline. In certain embodiments, the topical suspension comprises about 1% (w/w) minocycline.

In certain embodiments, the method comprises topically administering to the eyelid margin of a patient in need thereof once or twice per day a dose of a minocycline topical suspension.

C. Third Method

Another aspect of the invention provides a method of treating a disorder selected from the group consisting of blepharitis, meibomitis, and ocular rosacea, wherein the method comprises topically administering to the eye of a patient in need thereof a therapeutically effective amount of a minocycline topical suspension to treat the disorder.

In certain embodiments, the method comprises topically administering to the eyelid margin of the patient in need thereof once or twice per day a dose of a minocycline topical suspension, wherein the dose provides from about 0.1 mg to about 1.4 mg of minocycline, and the minocycline topical suspension comprises:
a) minocycline in a suspended form within the topical suspension;
b) a liquid medium that dissolves less than 5% (w/w) of the minocycline at room temperature after two hours, wherein the liquid medium contains mineral oil; and
c) a polymeric hydrocarbon gelling agent;
wherein particles of minocycline in the topical suspension have a D90 particle size less than 8 microns, and the topical suspension comprises from about 0.1% (w/w) to about 2% (w/w) minocycline.

D. Additional Exemplary Features of the First, Second, and Third Therapeutic Methods Additional exemplary features that may characterize the First, Second, and Third Therapeutic Methods described herein are provided below and include, for example, features of the minocycline topical suspension, the dosing amount of minocycline topical suspension, and dosing regimen used to administer the minocycline topical suspension to the patient. A more thorough description of such features is provided below. The invention embraces all permutations and combinations of these features.

1. Minocycline Topical Suspension

The method may be further characterized according to the composition of the minocycline topical suspension. For example, the method can be characterized according to the amount of minocycline in suspended form within the topical suspension, the physical form of minocycline, and the liquid medium that dissolves less than 5% (w/w) of the minocycline at room temperature after two hours, wherein the liquid medium contains mineral oil. These are described in more detail below.

Amount of Minocycline

The method may be further characterized according to the amount of minocycline in the topical suspension. For example, in certain embodiments, the topical suspension comprises from about 0.3% (w/w) to about 1% (w/w) minocycline. In certain embodiments, the topical suspension comprises from about 0.2% (w/w) to about 0.4% (w/w) minocycline. In certain embodiments, the topical suspension comprises about 0.3% (w/w) minocycline. In certain embodiments, the topical suspension comprises 0.3% (w/w) minocycline. In certain embodiments, the topical suspension comprises from about 0.9% (w/w) to about 1.1% (w/w) minocycline. In certain embodiments, the topical suspension comprises about 1% (w/w) minocycline. In certain embodiments, the topical suspension comprises 1% (w/w) minocycline.

Form of Minocycline

The method may be further characterized according to the physical form of the minocycline. For example, in certain embodiments, the minocycline is crystalline. Particular crystalline forms include Form I, Form II, and Form III. Additional details on minocycline crystalline Form I, Form II, and Form III are described herein below and in U.S. Pat. No. 8,258,327, which is hereby incorporated by reference.

Minocycline is understood to provide advantages over minocycline hydrochloride when used in a topical suspension for administration to the eye. One advantage of minocycline is that it is less acidic than minocycline hydrochloride—the less acidic minocycline is better tolerated by the eye. That is, minocycline causes less stinging and/or burning upon administration to the eye than minocycline hydrochloride. An aqueous solution containing 1% w/v minocycline has a pH in the range of 6.0 to 6.5, whereas an aqueous solution containing 1% w/v minocycline hydrochloride has a pH in the range of 3.5 to 4.5. A further characterization of the acidity of minocycline is pKa values—minocycline has pKa values of 3.5, 7.6, and 9.2, whereas minocycline hydrochloride has pKa values of 2.8, 5.0, and 9.3. Another advantage of minocycline is that it is more lipophilic than minocycline hydrochloride. Minocycline has a log P value of 0.11, whereas minocycline hydrochloride has a log P value of 0.05.

A. Minocycline Crystalline Form I.

Figure 2:
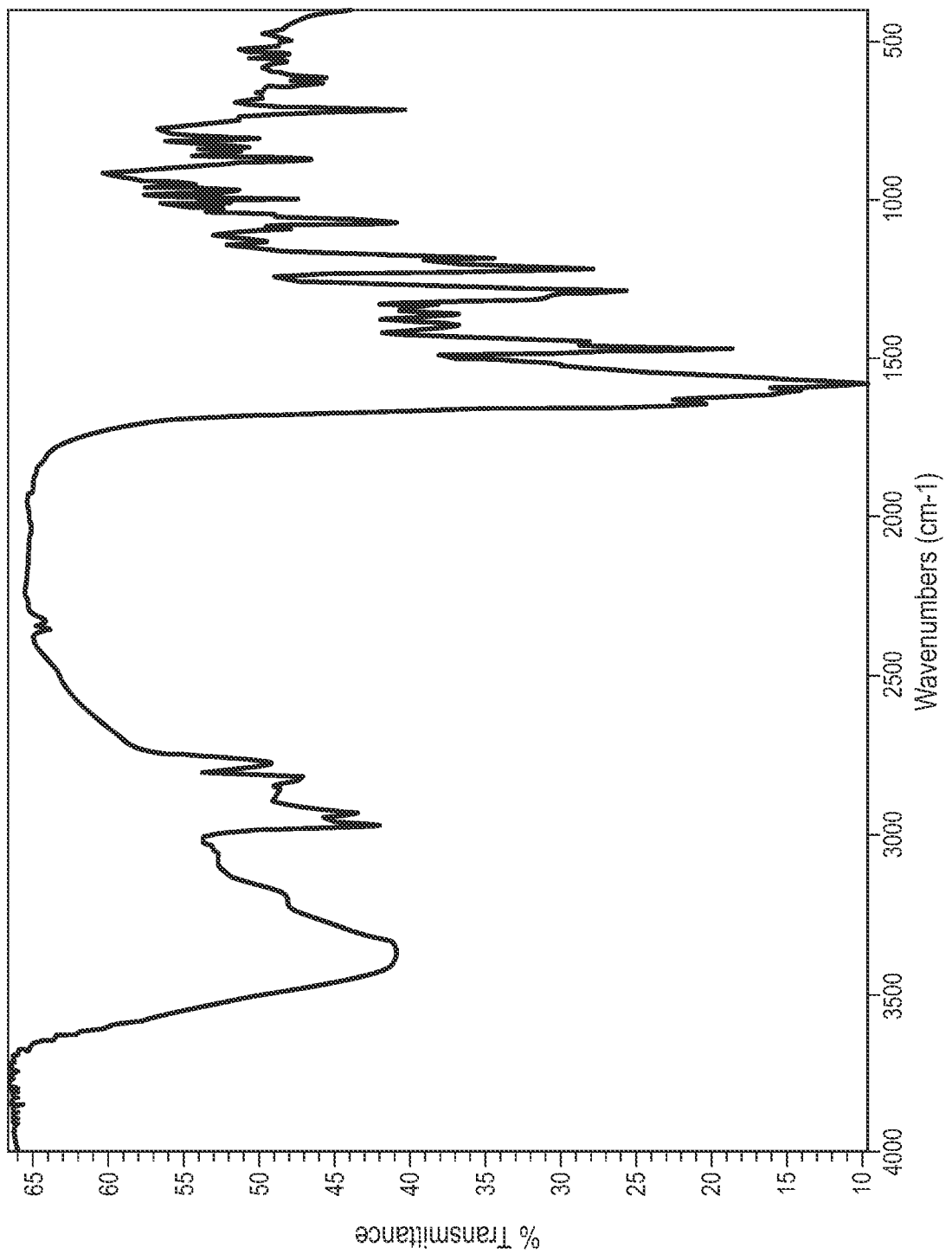
FIG. 2 depicts an infrared spectrum of crystalline form I of minocycline.

In certain embodiments, the minocycline is crystalline and characterized by an X-ray diffraction pattern having peaks at 5.2, 7.6, 8.8, 12.8, 14.5, 15.0, 15.3, 15.9, 16.4, 17.8, 19.3, 19.5, 20.7, 21.3, 21.8, 22.3, 23.1, 24.0, 25.3, 25.7 and 26.5±0.2 degrees 2θ. In certain embodiments, the minocycline is crystalline and has an X-ray diffraction pattern substantially as shown in FIG. 1. In certain embodiments, the minocycline is crystalline and characterized by an infrared spectrum having peaks at 1646, 1602, 1581, 1470, 1397, 1364, 1286, 1218, 1182, 1134, 1072, 1061, 1023, 1001, 969, 950, 874, 850, 716, 636, 620 and 545±4 cm$^{-1}$. In certain embodiments, the minocycline is crystalline and has an infrared spectrum substantially as shown in FIG. 2.

B. Minocycline Crystalline Form II.

Figure 3:
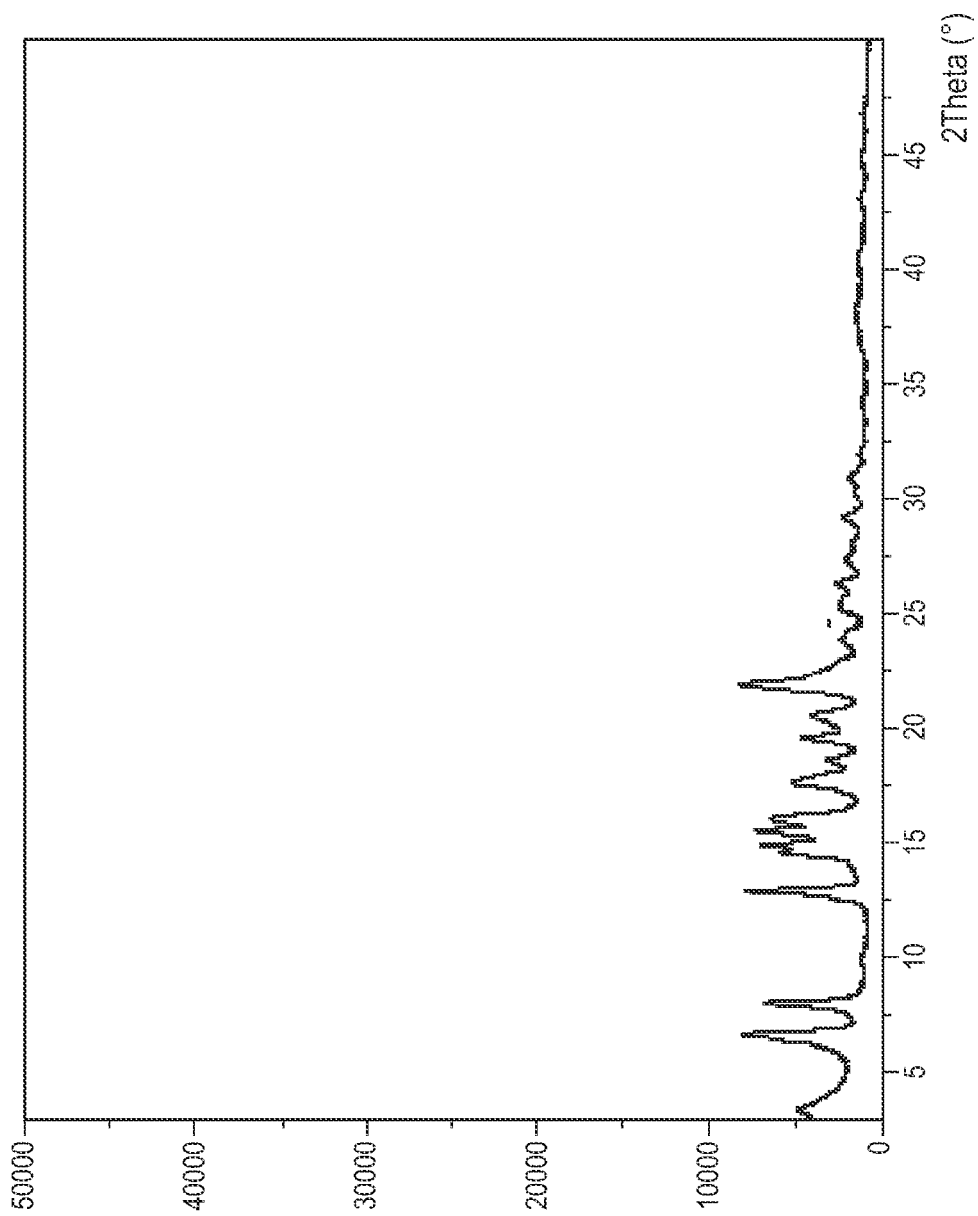
FIG. 3 depicts an X-ray powder diffraction spectrum of crystalline form II of minocycline.
Figure 4:
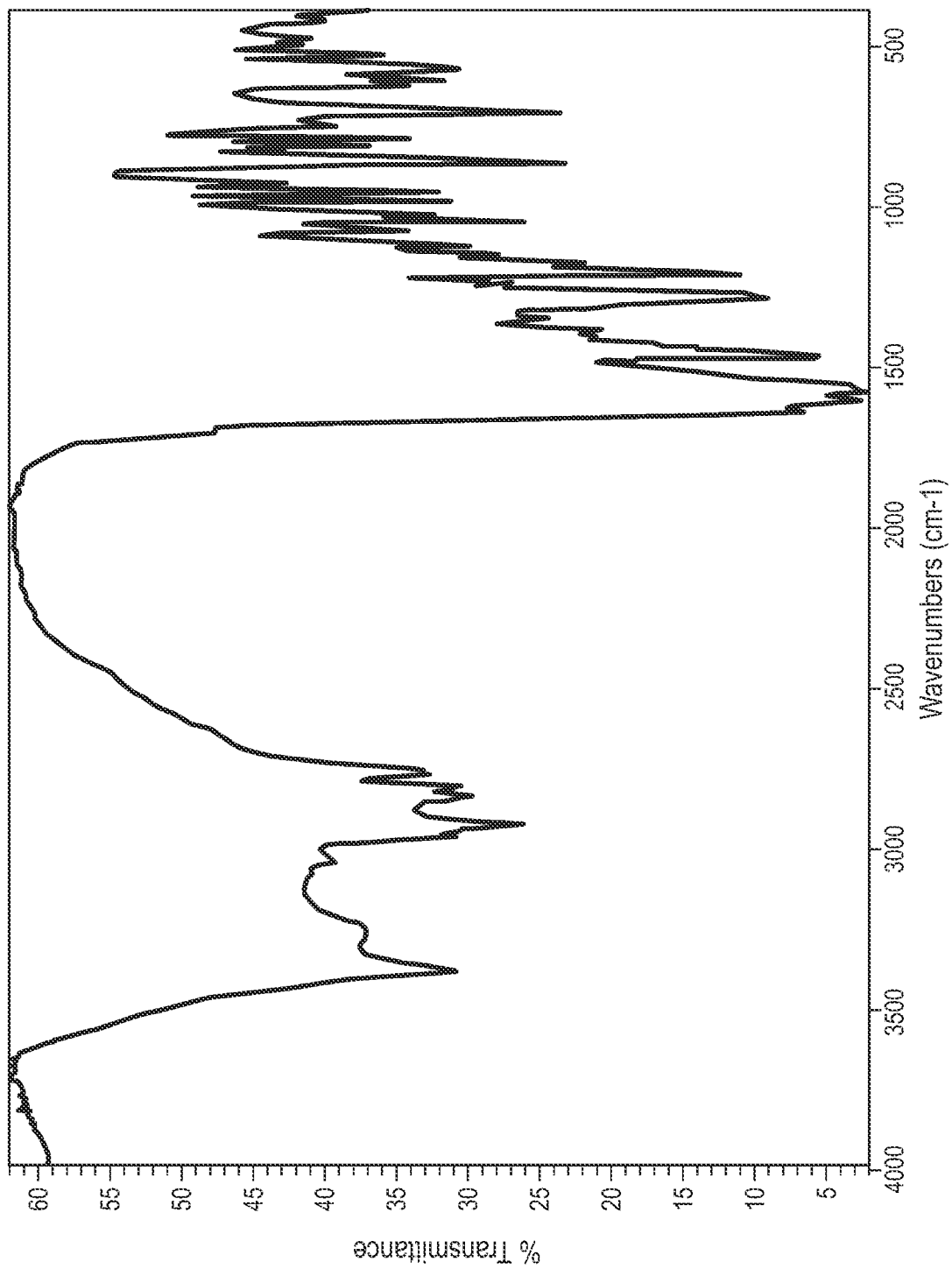
FIG. 4 depicts an infrared spectrum of crystalline form II of minocycline.

In certain embodiments, the minocycline is crystalline and characterized by an X-ray diffraction pattern having peaks at 3.4, 6.8, 8.0, 10.0, 13.0, 13.8, 22.6, and 23.9±0.2 degrees 2θ. In certain embodiments, the minocycline is crystalline and characterized by an X-ray diffraction pattern having peaks at 3.4, 6.8, 8.0, 10.0, 13.0, 13.8, 14.6, 14.9, 15.5, 16.1, 17.6, 17.8, 18.6, 19.5, 20.2, 20.6, 21.9, 22.6, 23.9, 24.2, 25.4, 26.3, 27.1, 27.5, 28.0 and 29.1±0.2 degrees 2θ. In certain embodiments, the minocycline is crystalline and has an X-ray diffraction pattern substantially as shown in FIG. 3. In certain embodiments, the minocycline is crystalline and characterized by an infrared spectrum having peaks at 1644, 1607, 1582, 1469, 1453, 1413, 1396, 1358, 1287, 1251, 1217, 1186, 1166, 1136, 1061, 999, 970, 874, 716, 621 and 585±4 cm$^{-1}$. In certain embodiments, the minocycline is crystalline and has an infrared spectrum substantially as shown in FIG. 4.

C. Minocycline Crystalline Form III.

Figure 5:
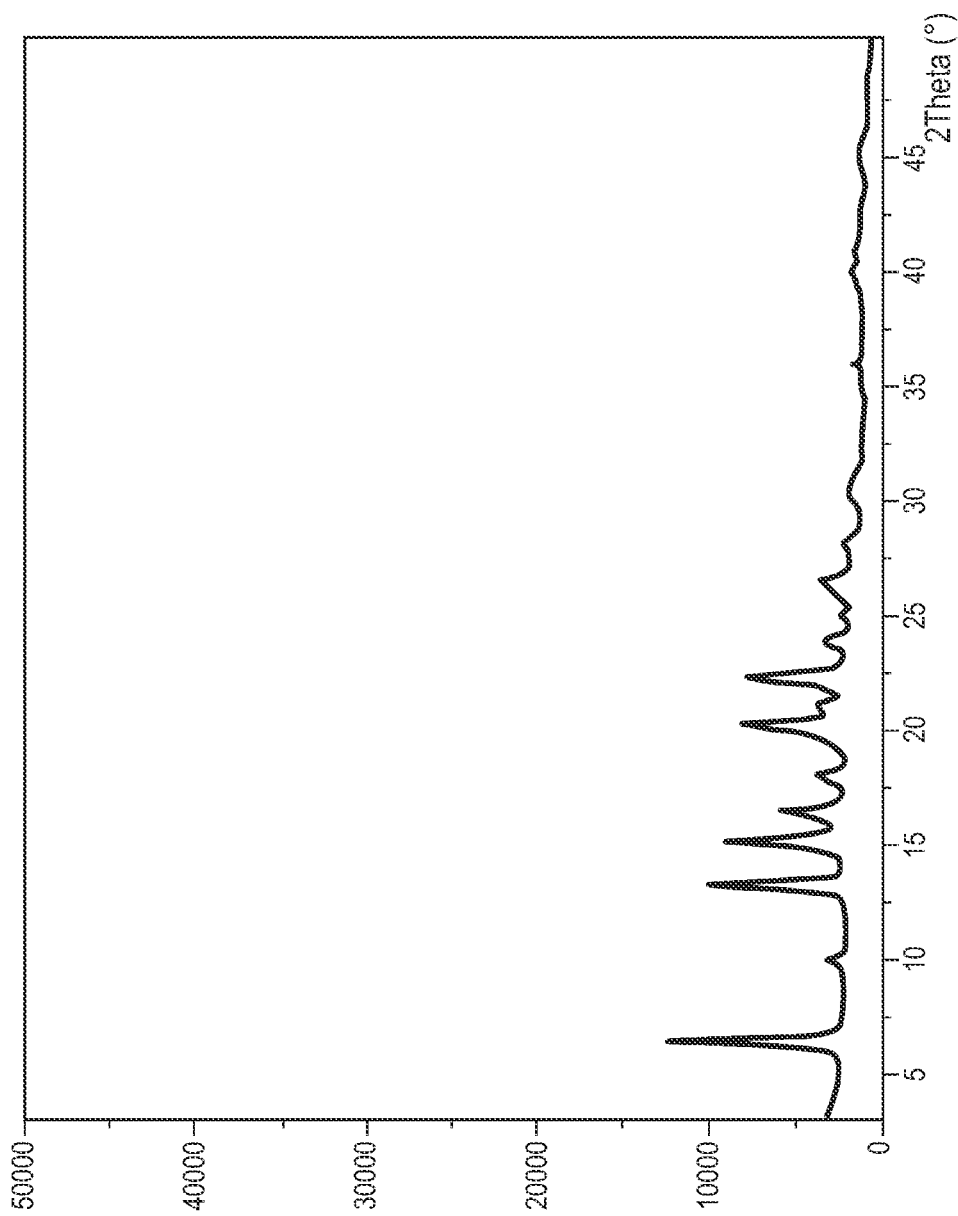
FIG. 5 depicts an X-ray powder diffraction spectrum of crystalline form III of minocycline.
Figure 6:
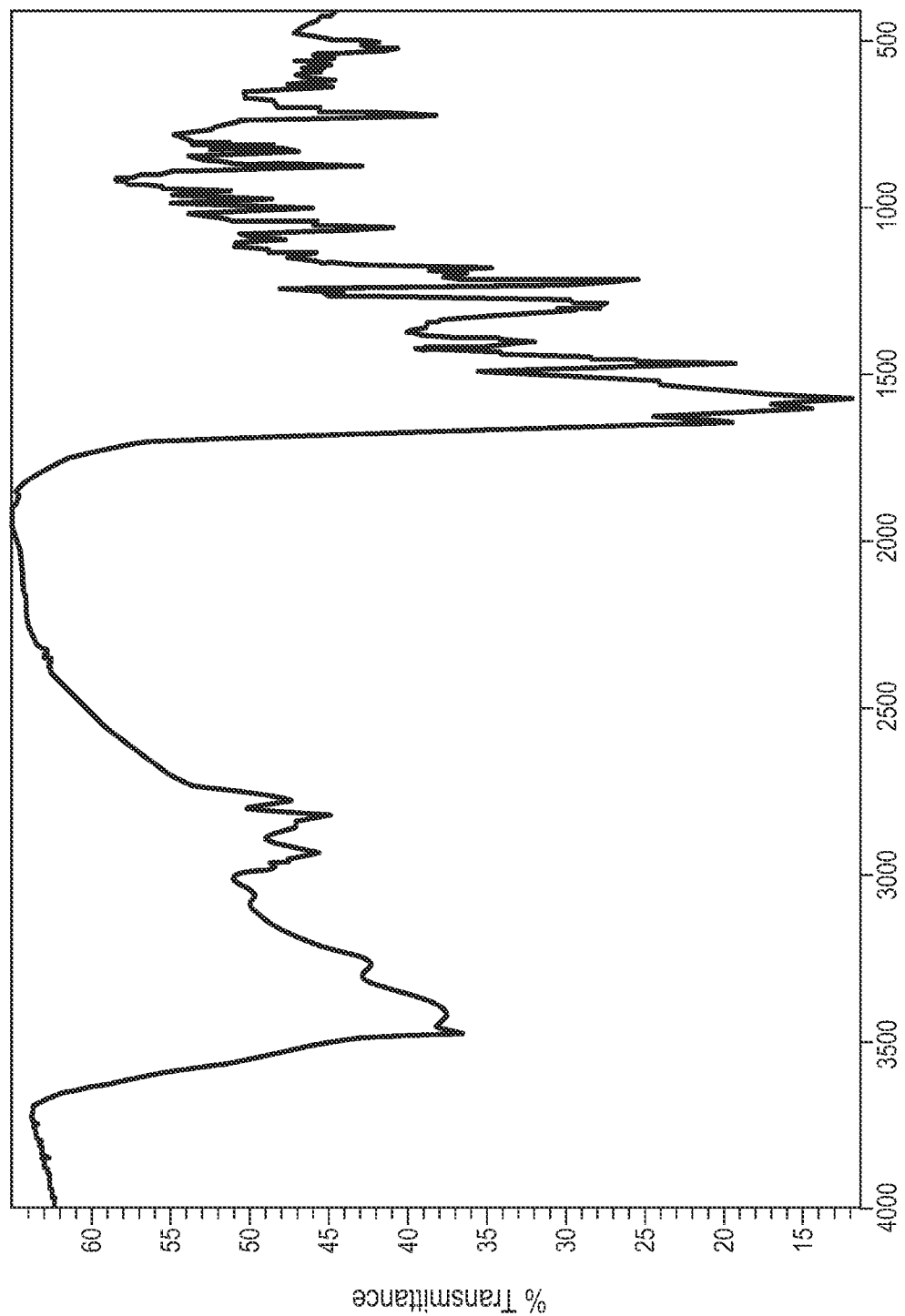
FIG. 6 depicts an infrared spectrum of crystalline form III of minocycline.

In certain embodiments, the minocycline is crystalline and characterized by an X-ray diffraction pattern having peaks at 6.5, 10.0, 13.2, 15.1, 16.5, 17.9, 19.6, 20.2, 21.1, 22.3, 23.7, 24.8, 26.4, 28.1 and 30.5±0.2 degrees 2θ. In certain embodiments, the minocycline is crystalline and has an X-ray diffraction pattern substantially as shown in FIG. 5. In certain embodiments, the minocycline is crystalline and characterized by an infrared spectrum having peaks at 1647, 1605, 1581, 1470, 1399, 1307, 1286, 1251, 1216, 1195, 1179, 1136, 1094, 1058, 1024, 1000, 973, 950, 870, 825, 806, 716, 680, 634, 615, 584, 515, 496 and 413±4 cm$^{-1}$. In certain embodiments, the minocycline is crystalline and has an infrared spectrum substantially as shown in FIG. 6.

Size of Particles of Minocycline

The method may be further characterized according to the size of particles of minocycline in the minocycline topical suspension. In certain embodiments, minocycline particles in the minocycline topical suspension have a D50 particle size that is from about 1 micron to about 4 microns. In certain embodiments, minocycline particles in the minocycline topical suspension have a D50 particle size that is from about 1 micron to about 3 microns. In certain embodiments, minocycline particles in the minocycline topical suspension have a D50 particle size that is from about 2 micron to about 3 microns. In certain embodiments, minocycline particles in the minocycline topical suspension have a D50 particle size that is about 2.5 microns. In certain embodiments, minocycline particles in the minocycline topical suspension have a D50 particle size that is less than about 3 microns. In certain embodiments, minocycline particles in the minocycline topical suspension have a D50 particle size that is less than about 2 microns.

In certain embodiments, minocycline particles in the minocycline topical suspension have a D10 particle size that is from about 0.1 microns to about 3 microns. In certain embodiments, minocycline particles in the minocycline topical suspension have a D10 particle size that is from about 0.1 microns to about 2 microns. In certain embodiments, minocycline particles in the minocycline topical suspension have a D10 particle size that is from about 0.1 microns to about 1 micron. In certain embodiments, minocycline particles in the minocycline topical suspension have a D10 particle size that is from about 0.1 microns to about 1.5 microns. In certain embodiments, minocycline particles in the minocycline topical suspension have a D10 particle size that is from about 0.1 micron to about 2 microns. In certain embodiments, minocycline particles in the minocycline topical suspension have a D10 particle size that is less than 2 microns. In certain embodiments, minocycline particles in the minocycline topical suspension have a D10 particle size that is less than 1 micron.

In certain embodiments, minocycline particles in the minocycline topical suspension have a D50 particle size that is from about 1 micron to about 3 microns, and a D10 particle size that is from about 0.1 microns to about 1 micron.

In certain embodiments, minocycline particles in the minocycline topical suspension have a D90 particle size that is from 1 micron to 8 microns. In certain embodiments, minocycline particles in the minocycline topical suspension have a D90 particle size that is from 1 micron to 7 microns. In certain embodiments, minocycline particles in the minocycline topical suspension have a D90 particle size that is from 1 micron to 5 microns. In certain embodiments, minocycline particles in the minocycline topical suspension have a D90 particle size that is from 2 microns to 5 microns. In certain embodiments, minocycline particles in the minocycline topical suspension have a D90 particle size that is from 2 microns to 4 microns. In certain embodiments, minocycline particles in the minocycline topical suspension have a D90 particle size that is from 3 microns to 4 microns. In certain embodiments, minocycline particles in the minocycline topical suspension have a D90 particle size that is less than 4 microns. In certain embodiments, minocycline particles in the minocycline topical suspension have a D90 particle size that is less than 3 microns. In certain embodiments, minocycline particles in the minocycline topical suspension have a D90 particle size that is one of about 3 microns, about 4 microns, about 5 microns, about 6 microns, about 7 microns, about 8 microns, or about 9 microns, or a fractional value in between any of these values. In certain embodiments, minocycline particles in the minocycline topical suspension have a D90 particle size that is about 3 microns. In certain embodiments, minocycline particles in the minocycline topical suspension have a D90 particle size that is one of about 3.5 microns.

Polymeric Hydrocarbon Gelling Agent

The method may be further characterized according to the amount of polymeric hydrocarbon gelling agent in the topical suspension. For example, in certain embodiments, the minocycline topical suspension comprises from about 60% (w/w) to about 80% (w/w) of the polymeric hydrocarbon gelling agent. In certain embodiments, the minocycline topical suspension comprises from about 65% (w/w) to about 75% (w/w) of the polymeric hydrocarbon gelling agent. In certain embodiments, the minocycline topical suspension comprises from about 67% (w/w) to about 71% (w/w) of the polymeric hydrocarbon gelling agent. In certain embodiments, the minocycline topical suspension comprises about 69% (w/w) of the polymeric hydrocarbon gelling agent.

In certain embodiments, the polymeric hydrocarbon gelling agent comprises an ethylene-propylene-styrene copolymer. In certain embodiments, the polymeric hydrocarbon gelling agent comprises an ethylene-propylene-styrene copolymer having a weight-average molecular weight in the range of from about 150,000 g/mol to about 250,000 g/mol. In certain embodiments, the polymeric hydrocarbon gelling agent comprises an ethylene-propylene-styrene copolymer having a weight-average molecular weight of about 200,000 g/mol.

In certain embodiments, the polymeric hydrocarbon gelling agent comprises from about 1% (w/w) to about 15% (w/w) of ethylene-propylene-styrene copolymer. In certain embodiments, the polymeric hydrocarbon gelling agent comprises from about 2.5% (w/w) to about 10% (w/w) of ethylene-propylene-styrene copolymer.

In certain embodiments, the ethylene-propylene-styrene copolymer is a copolymer formed by polymerization of isoprene and styrene monomers that is terminated by hydrogenation. In certain embodiments, the ethylene-propylene-styrene copolymer is a copolymer formed by polymerization of isoprene and styrene followed by hydrogenation.

In certain embodiments, the polymeric hydrocarbon gelling agent comprises a butylene-ethylene-styrene copolymer. In certain embodiments, the polymeric hydrocarbon gelling agent comprises a butylene-ethylene-styrene copolymer having a weight-average molecular weight in the range of from about 50,000 g/mol to about 150,000 g/mol. In certain embodiments, the polymeric hydrocarbon gelling agent comprises a butylene-ethylene-styrene copolymer having a weight-average molecular weight of about 100,000 g/mol.

In certain embodiments, the polymeric hydrocarbon gelling agent comprises from about 0.01% (w/w) to about 2.5% (w/w) of butylene-ethylene-styrene copolymer. In certain embodiments, the polymeric hydrocarbon gelling agent comprises from about 0.1% (w/w) to about 2.5% (w/w) of butylene-ethylene-styrene copolymer.

In certain embodiments, the butylene-ethylene-styrene copolymer is a copolymer formed by polymerization of 1,3-butadiene and styrene monomers that is terminated by hydrogenation. In certain embodiments, the butylene-ethylene-styrene copolymer is a copolymer formed by polymerization of 1,3-butadiene and styrene followed by hydrogenation.

In certain embodiments, the polymeric hydrocarbon gelling agent comprises butylated-hydroxytoluene. In certain embodiments, the polymeric hydrocarbon gelling agent comprises from about 0.01% (w/w) to about 0.5% (w/w) of butylated-hydroxytoluene. In certain embodiments, the polymeric hydrocarbon gelling agent comprises butylated-hydroxytoluene in an amount less than 0.5% (w/w).

In certain embodiments, the polymeric hydrocarbon gelling agent comprises mineral oil. In certain embodiments, the polymeric hydrocarbon gelling agent comprises at least about 80% (w/w) mineral oil. In certain embodiments, the polymeric hydrocarbon gelling agent comprises at least about 90% (w/w) mineral oil. In certain embodiments, the mineral oil component of the polymeric hydrocarbon gelling agent has a weight-average molecular weight in the range of from about 100 g/mol to about 1,000 g/mol. In certain embodiments, the mineral oil component of the polymeric hydrocarbon gelling agent has a weight-average molecular weight in the range of from about 200 g/mol to about 700 g/mol. In certain embodiments, the mineral oil is white mineral oil.

In certain embodiments, the polymeric hydrocarbon gelling agent comprises
(a) at least 80% (w/w) mineral oil;
(b) from about 2.5% (w/w) to about 10% (w/w) of ethylene-propylene-styrene copolymer; and
(c) comprises from about 0.1% (w/w) to about 2.5% (w/w) of butylene-ethylene-styrene copolymer.

In certain embodiments, the polymeric hydrocarbon gelling agent comprises
(a) at least 80% (w/w) mineral oil having a weight-average molecular weight in the range of from about 100 g/mol to about 1,000 g/mol;
(b) from about 2.5% (w/w) to about 10% (w/w) of ethylene-propylene-styrene copolymer having a weight-average molecular weight of about 200,000 g/mol; and
(c) comprises from about 0.1% (w/w) to about 2.5% (w/w) of butylene-ethylene-styrene copolymer having a weight-average molecular weight of about 100,000 g/mol.

In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity in the range of from about 13,000 to about 28,000 cps at 25° C., as sold by Calumet Specialty Products Partners, L.P. under the tradename VERSAGEL® M200. In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity of about 20,0000 cps at 25° C., as sold by Calumet Specialty Products Partners, L.P. under the tradename VERSAGEL® M200.

In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity in the range of from about 47,000 to about 57,000 cps at 25° C., as sold by Calumet Specialty Products Partners, L.P. under the tradename VERSAGEL® M500. In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity of about 50,0000 cps at 25° C., as sold by Calumet Specialty Products Partners, L.P. under the tradename VERSAGEL® M500.

In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity in the range of from about 67,000 to about 83,000 cps at 25° C., as sold by Calumet Specialty Products Partners, L.P. under the tradename VERSAGEL® M750. In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity of about 75,000 cps at 25° C., as sold by Calumet Specialty Products Partners, L.P. under the tradename VERSAGEL® M750.

In certain embodiments, the polymeric hydrocarbon gelling agent is a mixture of mineral oil, ethylene-propylene-styrene copolymer, butylene-ethylene-styrene copolymer, and optionally butylated-hydroxytoluene having a viscosity of about 160,0000 cps at 25° C., as sold by Calumet Specialty Products Partners, L.P. under the tradename VERSAGEL® M1600.

Liquid Medium

The method may be further characterized according to the amount of liquid medium that dissolves less than 5% (w/w) of the minocycline at room temperature after two hours. For example, in certain embodiments, the minocycline topical suspension comprises from about 20% (w/w) to about 40% (w/w) of the liquid medium that dissolves less than 5% (w/w) of the minocycline at room temperature after two hours, wherein the liquid medium contains mineral oil. In certain embodiments, the minocycline topical suspension comprises from about 25% (w/w) to about 35% (w/w) of the liquid medium that dissolves less than 5% (w/w) of the minocycline at room temperature after two hours, wherein the liquid medium contains mineral oil. In certain embodiments, the minocycline topical suspension comprises from about 28% (w/w) to about 32% (w/w) of the liquid medium that dissolves less than 5% (w/w) of the minocycline at room temperature after two hours, wherein the liquid medium contains mineral oil. In certain embodiments, the minocycline topical suspension comprises about 30% (w/w) of the liquid medium that dissolves less than 5% (w/w) of the minocycline at room temperature after two hours, wherein the liquid medium contains mineral oil.

In certain embodiments, the liquid medium that dissolves less than 5% (w/w) of the minocycline at room temperature after two hours comprises at least 90% (w/w) mineral oil. In certain embodiments, the liquid medium that dissolves less than 5% (w/w) of the minocycline at room temperature after two hours comprises at least 99% (w/w) mineral oil. In certain embodiments, the liquid medium that dissolves less than 5% (w/w) of the minocycline at room temperature after two hours is mineral oil.

In certain embodiments, the mineral oil has a weight-average molecular weight in the range of from about 100 g/mol to about 1,000 g/mol. In certain embodiments, the mineral oil has a weight-average molecular weight in the range of from about 200 g/mol to about 700 g/mol. In certain embodiments, the mineral oil has a weight-average molecular weight in the range of from about 230 g/mol to about 700 g/mol.

In certain embodiments, the mineral oil has a weight-average molecular weight in the range of from about 200 g/mol to about 500 g/mol. In certain embodiments, the mineral oil has a weight-average molecular weight in the range of from about 300 g/mol to about 600 g/mol. In certain embodiments, the mineral oil has a weight-average molecular weight in the range of from about 400 g/mol to about 700 g/mol. In certain embodiments, the mineral oil has a weight-average molecular weight in the range of from about 400 g/mol to about 500 g/mol. In certain embodiments, the mineral oil has a weight-average molecular weight in the range of from about 440 g/mol to about 465 g/mol.

In certain embodiments, the mineral oil has a molecular weight in the range of from about 440 g/mol to about 465 g/mol. In certain embodiments, the mineral oil has a molecular weight of about 452 g/mol.

In certain embodiments, the mineral oil has a viscosity greater than 34.5 centistokes when measured at 40° C. In certain embodiments, the mineral oil has a viscosity in the range of from about 34.5 centistokes to about 150 centistokes when measured at 40° C. In certain embodiments, the mineral oil has a viscosity in the range of from about 34.5 centistokes to about 50 centistokes, from about 50 centistokes to about 75 centistokes, from about 75 centistokes to about 100 centistokes, from about 100 centistokes to about 125 centistokes, from about 125 centistokes to about 150 centistokes, or from about 34.5 centistokes to about 100 centistokes when measured at 40° C.

In certain embodiments, the mineral oil has a specific gravity of from about 0.845 to about 0.905. In certain embodiments, the mineral oil has a specific gravity of from about 0.8 to about 0.95. In certain embodiments, the mineral oil has a specific gravity of from about 0.8 to about 0.9. In certain embodiments, the mineral oil has a specific gravity of from about 0.84 to about 0.91. In certain embodiments, the mineral oil has a specific gravity of from about 0.845 to about 0.905, when measured at 20° C. In certain embodiments, the mineral oil has a specific gravity of from about 0.8 to about 0.95, when measured at 20° C. In certain embodiments, the mineral oil has a specific gravity of from about 0.8 to about 0.9, when measured at 20° C. In certain embodiments, the mineral oil has a specific gravity of from about 0.84 to about 0.91, when measured at 20° C. In certain embodiments, the mineral oil has a density of about 0.83 g/mL.

In certain embodiments, the mineral oil corresponds to the mineral oil identified by CAS registry number 8042-47-5.

In certain embodiments, the mineral oil has a viscosity less than 34.5 centistokes when measured at 40° C. In certain embodiments, the mineral oil has a viscosity less than 33.5 centistokes when measured at 40° C. In certain embodiments, the mineral oil has a viscosity in the range of from about 1 centistoke to about 34.4 centistokes when measured at 40° C. In certain embodiments, the mineral oil has a viscosity in the range of from about 1 centistoke to about 10 centistokes, from about 10 centistokes to about 20 centistokes, from about 20 centistokes to about 30 centistokes, or from about 25 centistokes to about 34.4 centistokes, when measured at 40° C.

In certain embodiments, the mineral oil has a specific gravity of from about 0.818 to about 0.88. In certain embodiments, the mineral oil has a specific gravity of from about 0.8 to about 0.9. In certain embodiments, the mineral oil has a specific gravity of from about 0.818 to about 0.88, when measured at 20° C. In certain embodiments, the mineral oil has a specific gravity of from about 0.8 to about 0.9, when measured at 20° C.

In certain embodiments, said liquid medium dissolves less than 4% (w/w) of the minocycline at room temperature after two hours. In certain embodiments, said liquid medium dissolves less than 3% (w/w) of the minocycline at room temperature after two hours. In certain embodiments, said liquid medium dissolves less than 2% (w/w) of the minocycline at room temperature after two hours. In certain embodiments, said liquid medium dissolves less than 1% (w/w) of the minocycline at room temperature after two hours. In certain embodiments, said liquid medium dissolves less than 0.1% (w/w) of the minocycline at room temperature after two hours. In certain embodiments, said liquid medium dissolves from about 0.01% (w/w) to about 4% (w/w) of the minocycline at room temperature after two hours. In certain embodiments, said liquid medium dissolves from about 0.1% (w/w) to about 4% (w/w) of the minocycline at room temperature after two hours. In certain embodiments, said liquid medium dissolves from about 0.1% (w/w) to about 3% (w/w) of the minocycline at room temperature after two hours. In certain embodiments, said liquid medium dissolves from about 0.1% (w/w) to about 2% (w/w) of the minocycline at room temperature after two hours. In certain embodiments, said liquid medium dissolves from about 0.1% (w/w) to about 1% (w/w) of the minocycline at room temperature after two hours. In certain embodiments, said liquid medium dissolves from about 0.5% (w/w) to about 2% (w/w) of the minocycline at room temperature after two hours. In certain embodiments, said liquid medium dissolves from about 0.5% (w/w) to about 1% (w/w) of the minocycline at room temperature after two hours.

In certain embodiments, the liquid medium is characterized by dissolving less than about 4% (w/w) of minocycline when held at room temperature for two hours. In certain embodiments, the liquid medium is characterized by dissolving less than about 3% (w/w) of minocycline when held at room temperature for two hours. In certain embodiments, the liquid medium is characterized by dissolving less than about 2% (w/w) of minocycline when held at room temperature for two hours. In certain embodiments, the liquid medium is characterized by dissolving less than about 1% (w/w) of minocycline when held at room temperature for two hours.

In certain embodiments, the liquid medium is characterized by dissolving from about 0.01% (w/w) to about 4% (w/w) minocycline when held at room temperature for two hours. In certain embodiments, the liquid medium is characterized by dissolving from about 0.1% (w/w) to about 4% (w/w) minocycline when held at room temperature for two hours. In certain embodiments, the liquid medium is characterized by dissolving from about 0.1% (w/w) to about 3% (w/w) minocycline when held at room temperature for two hours. In certain embodiments, the liquid medium is characterized by dissolving from about 0.1% (w/w) to about 2% (w/w) minocycline when held at room temperature for two hours. In certain embodiments, the liquid medium is characterized by dissolving from about 0.1% (w/w) to about 1% (w/w) minocycline when held at room temperature for two hours. In certain embodiments, the liquid medium is characterized by dissolving from about 0.5% (w/w) to about 2% (w/w) minocycline when held at room temperature for two hours. In certain embodiments, the liquid medium is characterized by dissolving less about 4%, 3%, 2%, 1%, or 0.1% (w/w) minocycline when held at room temperature for two hours.

Stability of Minocycline Topical Suspension

The method may be further characterized according to the stability of the minocycline topical suspension used. For example, in certain embodiments, the minocycline topical suspension contains less than 4% (w/w) of 4-epi-minocycline when the minocycline topical suspension is stored for 1 month at room temperature. In certain embodiments, the minocycline topical suspension contains less than 3%, 2%, or 1% (w/w) of 4-epi-minocycline when the minocycline topical suspension is stored for 1 month at room temperature.

In certain embodiments, the minocycline topical suspension contains less than 3%, 2%, or 1% (w/w) of 4-epi-minocycline when the minocycline topical suspension is stored at 25° C.±2° C. under 60%±5% relative humidity for 36 months. In certain embodiments, the minocycline topical suspension contains less than 1% (w/w) of 4-epi-minocycline when the minocycline topical suspension is stored at 25° C.±2° C. under 60%±5% relative humidity for 36 months. In certain embodiments, the minocycline topical suspension contains less than 3%, 2%, or 1% (w/w) of 4-epi-minocycline when the minocycline topical suspension is stored at 40° C.±2° C. under 75%±5% relative humidity for 6 months.

In certain embodiments, less than 1% (w/w) of minocycline in the minocycline topical suspension degrades upon storage of the minocycline topical suspension at 25° C.±2° C. under 60%±5% relative humidity for 36 months. In certain embodiments, less than 1.5% (w/w) of minocycline in the minocycline topical suspension degrades upon storage of the minocycline topical suspension at 25° C.±2° C. under 60%±5% relative humidity for 36 months. In certain embodiments, less than 2% (w/w) of minocycline in the minocycline topical suspension degrades upon storage of the minocycline topical suspension at 25° C.±2° C. under 60%±5% relative humidity for 36 months. In certain embodiments, less than 5, 4, 3, 2, 1, 0.5, or 0.1% (w/w) of minocycline in the minocycline topical suspension degrades upon storage of the minocycline topical suspension at 25° C.±2° C. under 60%±5% relative humidity for 36 months. In certain embodiments, less than 5, 4, 3, 2, 1, 0.5, or 0.1% (w/w) of minocycline in the minocycline topical suspension degrades upon storage of the minocycline topical suspension at 25° C.±2° C. under 60%±5% relative humidity for 24 months. In certain embodiments, less than 5, 4, 3, 2, 1, 0.5, or 0.1% (w/w) of minocycline in the minocycline topical suspension degrades upon storage of the minocycline topical suspension at 405° C.±2° C. under 75%±5% relative humidity for 6 months.

In certain embodiments, storage of the minocycline topical suspension at 25° C.±2° C. under 60%±5% relative humidity for 36 months results in the formulation of less than 2% (w/w) total impurities. In certain embodiments, storage of the minocycline topical suspension at 25° C.±2° C. under 60%±5% relative humidity for 36 months results in the formulation of less than 3% (w/w) total impurities. In certain embodiments, storage of the minocycline topical suspension at 25° C.±2° C. under 60%±5% relative humidity for 36 months results in the formulation of less than 8%, 7%, 6%, 5%, 4%, 3%, 2%, or 1% (w/w) total impurities. In certain embodiments, storage of the minocycline topical suspension at 25° C.±2° C. under 60%±5% relative humidity for 24 months results in the formulation of less than 8%, 7%, 6%, 5%, 4%, 3%, 2%, or 1% (w/w) total impurities. In certain embodiments, storage of the minocycline topical suspension at 40° C.±2° C. under 75%±5% relative humidity for 6 months results in the formulation of less than 8%, 7%, 6%, 5%, 4%, 3%, 2%, or 1% (w/w) total impurities.

Sterility Level of the Minocycline Topical Suspension

The method may be further characterized according to the sterility of the minocycline topical suspension used. For example, in certain embodiments, the minocycline topical suspension has undergone sterilization, such as by exposing the minocycline topical suspension gamma or e-beam sterilization. The level of sterility of the minocycline topical suspension may be characterized, e.g., where the minocycline topical suspension has a sterility assurance level that is more sterile than $10^{-1}$, $10^{-2}$, $10^{-3}$, $10^{-4}$, $10^{-5}$, $10^{-6}$, $10^{-7}$, $10^{-8}$, or $10^{-9}$. In certain embodiments, the minocycline topical suspension has a sterility assurance level of from about $10^{-1}$ to $10^{-3}$, about $10^{-3}$ to about $10^{-4}$, about $10^{-4}$ to about $10^{-5}$, about $10^{-5}$ to about 10', or about $10^{-6}$ to about $10^{-7}$, or a sterility assurance level that is more sterile than $10^{-7}$. In certain embodiments, the minocycline topical suspension has a sterility assurance level of about $10^{-6}$.

Non-Newtonian Physical Properties

The minocycline topical suspension desirably displays non-Newtonian physical properties. That is, minocycline topical suspension is a non-Newtonian fluid. Such non-Newtonian physical properties provide superior residence time on the eyelid margin when the minocycline topical suspension is applied to the eyelid margin. Such non-Newtonian physical properties also minimize exposure of the cornea surface to topical minocycline suspension when the minocycline topical suspension is applied to the eyelid margin.

A desired non-Newtonian physical property is where the minocycline topical suspension undergoes a reduction in viscosity due to mechanical forces imposed on the minocycline topical suspension due to the patient blinking their eye.

Viscosity of the topical minocycline suspension can be measured a different shear rates. For example, in certain embodiments, at a shear rate of 6 (1/s), the minocycline topical suspension has a viscosity in the range of from about 1,000 cP to about 45,000 cP, from about 3,000 cP to about 30,000 cP, from about 3,000 cP to about 25,000 cP, from about 3,000 cP to about 20,000 cP, from about 3,000 cP to about 15,000 cP, from about 5,000 cP to about 30,000 cP, from about 5,000 cP to about 25,000 cP, from about 5,000 cP to about 20,000 cP, from about 5,000 cP to about 15,000 cP, from about 6,000 cP to about 20,000 cP. In certain embodiments, at a shear rate of 6 (1/s), the minocycline topical suspension has a viscosity in the range of from about 7,000 cP to about 15,000 cP. In certain embodiments, at a shear rate of 6 (1/s), the minocycline topical suspension has a viscosity in the range of from about 25 Pa·s to about 35 Pa·s. In certain embodiments, at a shear rate of 6 (1/s), the minocycline topical suspension has a viscosity in the range of from about 28 Pa·s to about 32 Pa·s. In certain embodiments, at a shear rate of 6 (1/s), the minocycline topical suspension has a viscosity of about 30 Pa·s.

In certain embodiments, at a shear rate of 1000/s, the minocycline topical suspension has a viscosity in the range of from about 0.5 Pa·s to about 0.9 Pa·s. In certain embodiments, at a shear rate of 1000/s, the minocycline topical suspension has a viscosity in the range of from about 0.65 Pa·s to about 0.8 Pa·s. In certain embodiments, at a shear rate of 1000/s, the minocycline topical suspension has a viscosity in the range of from about 0.70 Pa·s to about 0.74 Pa·s. In certain embodiments, at a shear rate of 1000/s, the minocycline topical suspension has a viscosity of about 0.72 Pa·s.

The topical minocycline suspension can also be characterized according to Oscillatory Stress Sweep, Oscillatory Frequency Sweep, Yield stress, Complex Modulus, and Loss Modulus. Additionally, the topical minocycline suspension can also be characterized according to normal stress test, which monitors the normal stress exhibited at a range of shear rates.

In certain embodiments, the minocycline topical suspension has a zero shear viscosity in the range of from about 250 Pa·s to about 350 Pa·s. In certain embodiments, the minocycline topical suspension has a zero shear viscosity in the range of from about 275 Pa·s to about 315 Pa·s. In certain embodiments, the minocycline topical suspension has a zero shear viscosity in the range of from about 290 Pa·s to about 300 Pa·s. In certain embodiments, the minocycline topical suspension has a zero shear viscosity of about 295 Pa·s. In certain embodiments, the minocycline topical suspension has a zero shear viscosity in the range of from about 300 Pa·s to about 350 Pa·s. In certain embodiments, the minocycline topical suspension has a zero shear viscosity in the range of from about 320 Pa·s to about 335 Pa·s. In certain embodiments, the minocycline topical suspension has a zero shear viscosity of about 328 Pa·s In certain embodiments, the minocycline topical suspension has a complex modulus plateau in the range of from about 130 Pa to about 150 Pa. In certain embodiments, the minocycline topical suspension has a complex modulus plateau in the range of from about 135 Pa to about 145 Pa. In certain embodiments, the minocycline topical suspension has a complex modulus plateau in the range of from about 138 Pa to about 141 Pa. In certain embodiments, the minocycline topical suspension has a phase angle plateau in the range of from about 20 degrees to about 30 degrees. In certain embodiments, the minocycline topical suspension has a phase angle plateau in the range of from about 24 degrees to about 28 degrees. In certain embodiments, the minocycline topical suspension has a phase angle plateau in the range of from about 25 degrees to about 27 degrees. In certain embodiments, the minocycline topical suspension has a yield stress in the range of from about 15 Pa to about 25 Pa. In certain embodiments, the minocycline topical suspension has a yield stress in the range of from about 18 Pa to about 24 Pa. In certain embodiments, the minocycline topical suspension has a yield stress in the range of from about 20 Pa to about 22 Pa.

Exemplary More Specific Embodiments

The disclosure provides the following additional specific embodiments. Accordingly, in certain embodiments, the minocycline topical suspension comprises:
(a) about 0.3% (w/w) to about 1% (w/w) minocycline;
(b) about 60% (w/w) to about 80% (w/w) of the polymeric hydrocarbon gelling agent; and
(c) about 20% (w/w) to about 40% (w/w) of the liquid medium that dissolves less than 5% (w/w) of the minocycline at room temperature after two hours, wherein the liquid medium contains mineral oil.

In certain embodiments, the minocycline topical suspension comprises:
(a) about 0.3% (w/w) minocycline;
(b) about 69% (w/w) of the polymeric hydrocarbon gelling agent; and
(c) about 30% (w/w) of the liquid medium that dissolves less than 5% (w/w) of the minocycline at room temperature after two hours, wherein the liquid medium contains mineral oil.

In certain embodiments, the minocycline topical suspension comprises:
(a) about 1% (w/w) minocycline;
(b) about 69% (w/w) of the polymeric hydrocarbon gelling agent; and
(c) about 30% (w/w) of the liquid medium that dissolves less than 5% (w/w) of the minocycline at room temperature after two hours, wherein the liquid medium contains mineral oil.

2. Dosage Considerations

The method may be further characterized according, for example, to the dosage, location to which the dosage is administered on the patient, and timing for the administration of the minocycline suspension to the patient.

Dosing Amounts

The method may be further characterized according to the dosing amount of minocycline. For example, in certain embodiments, the dose of minocycline topical suspension provides from about 0.1 mg to about 1.2 mg of minocycline. In certain embodiments, the dose of minocycline topical suspension provides from about 0.1 mg to about 1 mg of minocycline. In certain embodiments, the dose of minocycline topical suspension provides from about 0.1 mg to about 0.3 mg of minocycline. In certain embodiments, the dose of minocycline topical suspension provides from about 0.1 mg to about 0.2 mg of minocycline. In certain embodiments, the dose of minocycline topical suspension provides about 0.15 mg of minocycline.

In certain embodiments, the dose of minocycline topical suspension provides from about 0.3 mg to about 0.7 mg of minocycline. In certain embodiments, the dose of minocycline topical suspension provides from about 0.4 mg to about 0.6 mg of minocycline. In certain embodiments, the dose of minocycline topical suspension provides from about 0.45 mg to about 0.55 mg of minocycline. In certain embodiments, the dose of minocycline topical suspension provides about 0.5 mg of minocycline. In certain embodiments, the dose of minocycline topical suspension provides from about 0.9 mg to about 1.1 mg of minocycline. In certain embodiments, the dose of minocycline topical suspension provides about 1 mg of minocycline.

In certain embodiments, an amount of from about 35 µL to about 65 µL of the minocycline topical suspension is topically administered to the eyelid margin of the patient. In certain embodiments, an amount of from about 40 µL to about 50 µL of the minocycline topical suspension is topically administered to the eyelid margin of the patient. In certain embodiments, an amount of from about 45 µL to about 55 µL of the minocycline topical suspension is topically administered to the eyelid margin of the patient. In certain embodiments, an amount of about 50 µL of the minocycline topical suspension is topically administered to the eyelid margin of the patient.

In certain embodiments, the minocycline topical suspension is topically administered to the eyelid margin of the patient using either a fingertip, application directly from a container containing the minocycline topical suspension, or a device for application of the minocycline topical suspension.

Location for Administration

The method may be further characterized according to the location for administration of the minocycline topical suspension. For example, in certain embodiments, the minocycline topical suspension is topically administered to the eyelid margin of the patient to form a strip having a width less than or equal to one-quarter inches. In certain embodiments, the minocycline topical suspension is topically administered to the eyelid margin of the patient to form a strip having a width of about one-quarter inches. In certain embodiments, the minocycline topical suspension is topically administered across the full margin of the eyelid.

When administering minocycline topical suspension to the eyelid margin, one embodiment is for the patient to pull down the lower eyelid and look up, then use their finger to apply minocycline topical suspension (e.g., a pea sized amount of minocycline topical suspension) to the inside of the lower eyelid, between the lower eyelid and the eye. The patient may optionally apply the minocycline topical suspension as a thin ribbon on the lower eyelid close to their nose (inner canthus) and direct outward without touching the eyelash or the eye. The ribbon of minocycline topical suspension is desirably deposited on the inside lining of the lower eyelid.

Application of minocycline topical suspension to the eyelid margin desirably brings the minocycline topical suspension into contact with one or more of the tarsal conjunctiva, conjunctival fornix, bulbar conjunctiva, or conjunctival sac. This disclosure provides methods where, in lieu of applying minocycline topical suspension as a strip across the eyelid margin, the minocycline topical suspension is administered directly to one or more of the tarsal conjunctiva, conjunctival fornix, bulbar conjunctiva, or conjunctival sac.

In certain embodiments, the minocycline topical suspension is administered to the eyelid margin of the patient using an applicator. In certain embodiments, the minocycline topical suspension is administered to the eyelid margin of the patient using a fingertip. In certain embodiments, the minocycline topical suspension is administered to the eyelid margin of the patient using a container or vessel containing the minocycline topical suspension.

Frequency of Administration

The method may be further characterized according to the frequency of administration of the dose of minocycline topical suspension. For example, in certain embodiments, the dose of minocycline topical suspension is administered twice per day. In certain embodiments, the dose of minocycline topical suspension is administered twice per day, wherein the first dose of minocycline topical suspension is administered in the morning and the second dose of minocycline topical suspension is administered in the evening. In certain embodiments, the dose of minocycline topical suspension is administered twice per day, wherein there is from about 8 hours to about 12 hours between administering the first dose of minocycline topical suspension and administering the second dose of minocycline topical suspension. In certain embodiments, the dose of minocycline topical suspension is administered twice per day, wherein there is at least about 8 hours between administering the first dose of minocycline topical suspension and administering the second dose of minocycline topical suspension. In certain embodiments, the dose of minocycline topical suspension is administered once per day.

In certain embodiments, for a duration of at least thirty days the patient receives a dose of minocycline topical suspension each day. In certain embodiments, for a duration of at least two months the patient receives a dose of minocycline topical suspension each day. In certain embodiments, for a duration of at least three months the patient receives a dose of minocycline topical suspension each day. In certain embodiments, for a duration of at least six months the patient receives a dose of minocycline topical suspension each day. In certain embodiments, for a duration of at least twelve months the patient receives a dose of minocycline topical suspension each day.

Blood Plasma Concentration

The method may be further characterized according to the blood plasma concentration measurements of minocycline resulting from administration of the topical minocycline topical suspension. For example, in certain embodiments, administration of the minocycline topical suspension results in a maximum blood plasma concentration of minocycline in the patient that does not exceed 5, 4, 3, 2, 1, or 0.5 µg/mL. In certain embodiments, administration of the minocycline topical suspension results in a maximum blood plasma concentration of minocycline in the patient that does not exceed 3 µg/mL. In certain embodiments, administration of the minocycline topical suspension results in a maximum blood plasma concentration of minocycline in the patient that does not exceed 1 µg/mL.

In certain embodiments, administration of the minocycline topical suspension results in an AUC of minocycline determined from monitoring blood plasma amounts of minocycline that does not exceed 46, 40, 35, 30, 25, 20, 15, 10, 9, 8, 7, 6, 5, 4, 3, 2, 1, or 0.5 h*µg/mL. In certain embodiments, administration of the minocycline topical suspension results in an AUC of minocycline determined from monitoring blood plasma amounts of minocycline that does not exceed 46 h*µg/mL. In certain embodiments, administration of the minocycline topical suspension results in an AUC of minocycline determined from monitoring blood plasma amounts of minocycline that does not exceed 1 h*µg/mL.

3. Patient Populations That May Derive Particular Benefits from the Therapeutic Methods The method may be further characterized according to the patient suffering from meibomian gland dysfunction that is being treated. For example, in certain embodiments, the patient is a human. In certain embodiments, the patient is an adult human. In certain embodiments, the patient has mild meibomian gland dysfunction. In certain embodiments, the patient has moderate meibomian gland dysfunction. In certain embodiments, the patient has severe meibomian gland dysfunction.

In certain embodiments, the patient suffers from dry eye. In certain embodiments, the patient suffers from evaporative dry eye disease.

In certain embodiments, the patient has an inflamed meibomian gland.

Tear Osmolarity

The method may be further characterized according to the tear osmolarity of the patient to be treated. For example, in certain embodiments, the patient has a tear osmolarity value greater than about 315 mOsmol/L. In certain embodiments, the patient has a tear osmolarity value greater than about 310, 312, 315, 320, 325, or 330 mOsmol/L. In certain embodiments, the patient has a tear osmolarity value in the range of from about 310 mOsmol/L to 330 mOsmol/L. In certain embodiments, the patient has a tear osmolarity value in the range of from about 310 mOsmol/L to 315 mOsmol/L. In certain embodiments, the patient has a tear osmolarity value in the range of from about 315 mOsmol/L to 330 mOsmol/L.

Tear Film Matrix Metalloproteinase-9 (MMP-9) Concentration

The method may be further characterized according to the tear film matrix metalloproteinase-9 (MMP-9) concentration of the patient to be treated. For example, in certain embodiments, the patient's tear film has a concentration of MMP-9 greater than about 40 ng/mL. In certain embodiments, the patient's tear film has a concentration of MMP-9 greater than or equal 40 ng/mL. In certain embodiments, the patient's tear film has a concentration of MMP-9 greater than about 45, 50, 55, 60, 65, 70, 75, or 80 ng/mL. In certain embodiments, the patient's tear film has a concentration of MMP-9 in the range of from about 40 ng/mL to about 60 ng/mL. In certain embodiments, the patient's tear film has a concentration of MMP-9 in the range of from about 60 ng/mL to about 80 ng/mL. In certain embodiments, the patient's tear film has a concentration of MMP-9 in the range of from about 40 ng/mL to about 80 ng/mL.

Tear Film Breakup Time

The method may be further characterized according to the tear film breakup time of the patient to be treated. For example, in certain embodiments, the patient's tear film breakup time has a breakup time of less than 10 seconds. For example, in certain embodiments, the tear film break up time is less than 8 seconds, 6 seconds, 4 seconds, or 2 seconds. In certain embodiments, the tear film break up time is in the range of 1 second to 10 seconds. In certain embodiments, the tear film break up time is in the range of 1 second to 5 seconds. In certain embodiments, the tear film break up time is in the range of 1 second to 4 seconds. In certain embodiments, the tear film break up time is in the range of 1 second to 2 seconds.

Meibomian Gland Dysfunction Symptom Flare Frequency

When treating meibomian gland dysfunction, the method may be further characterized according to the frequency of symptom flare due to meibomian gland dysfunction in the patient to be treated. For example, in certain embodiments, the patient experiences a symptom flare due to meibomian gland dysfunction on an average of at least 1, 2, 3, 4, 5, 6, 7, 8, 9, 10, 15, 20, 25, or 30 times per day. In certain embodiments, the patient experiences a symptom flare due to meibomian gland dysfunction on an average of at least one time per day. In certain embodiments, the patient experiences a symptom flare due to meibomian gland dysfunction on an average of at least 2 times per day. In certain embodiments, the patient experiences a symptom flare due to meibomian gland dysfunction on an average of at least 3 times per day. In certain embodiments, the patient experiences a symptom flare due to meibomian gland dysfunction on an average of at least one time per every two days. In certain embodiments, the patient experiences a symptom flare due to meibomian gland dysfunction on an average of from once per day to 5 times per day.

In certain embodiments, the patient experiences a symptom flare due to meibomian gland dysfunction on an average of at least 1, 2, 3, 4, 5, 6, 7, 8, 9, 10, 15, 20, 25, or 30 times per week. In certain embodiments, the patient experiences a symptom flare due to meibomian gland dysfunction on an average of at least 5 times per week. In certain embodiments, the patient experiences a symptom flare due to meibomian gland dysfunction on an average of at least 10 times per week. In certain embodiments, the patient experiences a symptom flare due to meibomian gland dysfunction on an average of at least 20 times per week. In certain embodiments, the patient experiences a symptom flare due to meibomian gland dysfunction on an average of at least 40 times per week. In certain embodiments, the patient experiences a symptom flare due to meibomian gland dysfunction on an average of from once per week to 15 times per week.

In certain embodiments, the patient has experienced an average of at least 2, 3, 4, 5, 6, 7, 8, 9, 10, 11, 12, 13, 14, 15, 20, 25, or 30 symptom flares due to meibomian gland dysfunction during the month prior to first administration of the minocycline topical suspension. In certain embodiments, the patient has experienced an average of at least five symptom flares due to meibomian gland dysfunction during the month prior to first administration of the minocycline topical suspension. In certain embodiments, the patient experiences a symptom flare due to meibomian gland dysfunction on an average of from 10 times per month to 30 times per month.

Therapeutic Improvements & Other Characteristics

The method may be further characterized according to therapeutic benefits of administration of minocycline topical suspension to the eyelid margin of the patient. Exemplary therapeutic benefits that may be measured are described herein below.

Reduction in Vascular Engorgement

The method may be further characterized according to the reduction in vascular engorgement experienced by the patient. For example, in certain embodiments, the method produces a reduction in vascular engorgement score of at least 1. In certain embodiments, the method produces a reduction in vascular engorgement score of at least 2. For example, in certain embodiments, the method produces a reduction in vascular engorgement score of at least 0.8, 0.9, 1, 1.1, or 1.2. In certain embodiments, after a duration of at least three months where the patient has received a dose of minocycline topical suspension each day, the patient has a vascular engorgement score of no greater than 1.5. In certain embodiments, after a duration of at least three months where the patient has received a dose of minocycline topical suspension each day, the patient has a vascular engorgement score of no greater than 1. In certain embodiments, after a duration of at least three months where the patient has received a dose of minocycline topical suspension each day, the patient has a vascular engorgement score of 0. In certain embodiments, after a duration of at least three months where the patient has received a dose of minocycline topical suspension each day, the patient has a vascular engorgement score of no greater than 2.0, 1.9, 1.8, 1.7, 1.6, 1.5, 1.4, 1.3, 1.2, 1.1, 1.0, 0.9, 0.8, or 0.7.

Reduction in Eye Discomfort Visual Analog Score

The method may be further characterized according to the reduction in the patient's eye discomfort visual analog score. For example, in certain embodiments, the method produces a reduction in Eye Discomfort Visual Analog Score of at least 20 percent. In certain embodiments, the method produces a reduction in Eye Discomfort Visual Analog Score of at least 20, 21, 22, 23, 24, 25, 26, 27, 28, 29, 30, 31, 32, 33, 34, or 35 percent. In certain embodiments, after a duration of at least three months where the patient has received a dose of minocycline topical suspension each day, the patient has an Eye Discomfort Visual Analog Score of no greater than 50. In certain embodiments, after a duration of at least three months where the patient has received a dose of pharmaceutical composition each day, the patient has an Eye Discomfort Visual Analog Score of no greater than 40. In certain embodiments, after a duration of at least three months where the patient has received a dose of pharmaceutical composition each day, the patient has an Eye Discomfort Visual Analog Score of no greater than 30. In certain embodiments, after a duration of at least three months where the patient has received a dose of minocycline topical suspension each day, the patient has an Eye Discomfort Visual Analog Score of no greater than 25. In certain embodiments, after a duration of at least three months where the patient has received a dose of minocycline topical suspension each day, the patient has an Eye Discomfort Visual Analog Score of no greater than 10. In certain embodiments, after a duration of at least three months where the patient has received a dose of minocycline topical suspension each day, the patient has an Eye Discomfort Visual Analog Score of no greater than 50, 45, 40, 39, 38, 37, 36, 35, 34, 33, 32, 31, or 30.

Reduction in Meibomian Gland Dysfunction Symptoms

When treating meibomian gland dysfunction, the method may be further characterized according to the reduction in meibomian gland dysfunction symptoms experienced by the patient. For example, in certain embodiments, the method produces a reduction in the number of symptom flares due to meibomian gland dysfunction. In certain embodiments, the method produces at least a 5%, 10%, 20%, 30%, 40%, 50%, 60%, 70%, 80%, 90%, or 100% reduction in the average number of symptom flares per month due to meibomian gland dysfunction compared to the average number of symptom flares due to meibomian gland dysfunction experienced by the patient in the month prior to first administering the minocycline topical suspension. In certain embodiments, the method produces at least a 10% reduction in the average number of symptom flares per month due to meibomian gland dysfunction compared to the average number of symptom flares due to meibomian gland dysfunction experienced by the patient in the month prior to first administering the minocycline topical suspension. In certain embodiments, the method produces at least a 50% reduction in the average number of symptom flares per month due to meibomian gland dysfunction compared to the average number of symptom flares due to meibomian gland dysfunction experienced by the patient in the month prior to first administering the minocycline topical suspension. In certain embodiments, said reduction is achieved within twelve weeks after first administering the minocycline topical suspension. In certain embodiments, said reduction is achieved within 4, 5, 6, 7, 8, 9 or 10 weeks after first administering the minocycline topical suspension.

Tear Osmolarity

The method may be further characterized according to the patient's tear osmolarity after receiving the minocycline topical suspension. For example, in certain embodiments, the method produces a reduction in tear osmolarity value in the patient. For example, in certain embodiments, the patient's tear osmolarity value is reduced to less than about 310, 312, or 315 mOsmol/L. In certain embodiments, the patient's tear osmolarity value is reduced to about 308 mOsmol/L.

In certain embodiments, the method produces at least a 1%, 2%, 3%, 4%, 5%, 6%, 7%, 8%, 9%, 10%, 12%, 14%, 16%, 18%, or 20% reduction in tear osmolarity value in the patient compared to the patient's tear osmolarity value prior to starting treatment using minocycline topical suspension. In certain embodiments, the method produces at least a 1%, 2%, 3%, or 4% reduction in tear osmolarity value in the patient compared to the patient's tear osmolarity value prior to starting treatment using minocycline topical suspension. In certain embodiments, the method produces at least a 1% to 5% reduction in tear osmolarity value in the patient compared to the patient's tear osmolarity value prior to starting treatment using minocycline topical suspension. In certain embodiments, the method produces a reduction in tear osmolarity value in the range of from about 5% to about 10%, from about 10% to about 20%, or from about 20% to about 50% in the patient compared to the patient's tear osmolarity value prior to starting treatment using minocycline topical suspension.

In certain embodiments, said reduction is achieved within twelve weeks after first administering the minocycline topical suspension. In certain embodiments, said reduction is achieved within 4, 5, 6, 7, 8, 9 or 10 weeks after first administering the minocycline topical suspension.

Tear Film MMP-9 Concentration

The method may be further characterized according to the patient's tear film MMP-9 concentration after receiving the minocycline topical suspension. For example, in certain embodiments, the method produces a reduction in MMP-9 concentration in the patient's tear film. For example, in certain embodiments, the patient's tear film MMP-9 concentration is reduced to less than about 5, 10, 15, 20, 25, 30, 35, or 40 ng/mL. In certain embodiments, the patient's tear film MMP-9 concentration is reduced to less than about 20 ng/mL. In certain embodiments, the patient's tear film MMP-9 concentration is reduced to less than about 40 ng/mL. In certain embodiments, the patient's tear film MMP-9 concentration is reduced to less than 40 ng/mL. In certain embodiments, the patient's tear film MMP-9 concentration is reduced to a concentration in the range of from about 3 ng/mL to about 40 ng/mL. In certain embodiments, the patient's tear film MMP-9 concentration is reduced to a concentration in the range of from about 3 ng/mL to about 20 ng/mL. In certain embodiments, the patient's tear film MMP-9 concentration is reduced to a concentration in the range of from about 20 ng/mL to about 40 ng/mL. In certain embodiments, the patient's tear film MMP-9 concentration is reduced to a concentration in the range of from about 3 ng/mL to less than 40 ng/mL.

In certain embodiments, the method produces at least a 1%, 2%, 3%, 4%, 5%, 6%, 7%, 8%, 9%, 10%, 12%, 14%, 16%, 18%, 20%, 30%, 40%, 50%, 60%, 70%, 80%, 90%, or 100% reduction in MMP-9 concentration in the patient's tear film compared to the patient's tear film MMP-9 concentration prior to starting treatment using minocycline topical suspension. In certain embodiments, the method produces at least a 5% reduction in MMP-9 concentration in the patient's tear film compared to the patient's tear film MMP-9 concentration prior to starting treatment using minocycline topical suspension. In certain embodiments, the method produces at least a 10% reduction in MMP-9 concentration in the patient's tear film compared to the patient's tear film MMP-9 concentration prior to starting treatment using minocycline topical suspension. In certain embodiments, the method produces at least a 20% reduction in MMP-9 concentration in the patient's tear film compared to the patient's tear film MMP-9 concentration prior to starting treatment using minocycline topical suspension.

In certain embodiments, said reduction is achieved within twelve weeks after first administering the minocycline topical suspension. In certain embodiments, said reduction is achieved within 4, 5, 6, 7, 8, 9 or 10 weeks after first administering the minocycline topical suspension.

In certain embodiments, after twelve weeks of administering the minocycline topical suspension, at least 20% of patients that originally had a tear film MMP-9 concentration of at least 40 ng/mL now have a tear film MMP-9 concentration less than 40 ng/mL. In certain embodiments, after twelve weeks of administering the minocycline topical suspension, at least 30% of patients that originally had a tear film MMP-9 concentration of at least 40 ng/mL now have a tear film MMP-9 concentration less than 40 ng/mL. In certain embodiments, after twelve weeks of administering the minocycline topical suspension, at least 40% of patients that originally had a tear film MMP-9 concentration of at least 40 ng/mL now have a tear film MMP-9 concentration less than 40 ng/mL. In certain embodiments, after twelve weeks of administering the minocycline topical suspension, at least 32%, 34%, 36%, 38%, 40%, 42%, 44%, 46%, or 48% of patients that originally had a tear film MMP-9 concentration of at least 40 ng/mL now have a tear film MMP-9 concentration less than 40 ng/mL.

Tear Film Breakup Time

The method may be further characterized according to the patient's tear film breakup time after receiving the minocycline topical suspension. For example, in certain embodiments, the method produces an increase in tear film breakup time. For example, in certain embodiments, the tear film break up time is increased to at least 10, 12, 14, or 16 seconds. In certain embodiments, the tear film break up time is increased to at least 10 seconds. In certain embodiments, the tear film break up time is increased to within the range of 10 seconds to 20 seconds. In certain embodiments, the tear film break up time is increased to within the range of 10 seconds to 14 seconds.

In certain embodiments, the method produces at least a 1%, 2%, 3%, 4%, 5%, 6%, 7%, 8%, 9%, 10%, 12%, 14%, 16%, 18%, 20%, 30%, 40%, 50%, 60%, 70%, 80%, 90%, or 100% increase in tear film breakup time compared to the patient's tear film break up time prior to starting treatment using minocycline topical suspension. In certain embodiments, the method produces at least a 10% increase in tear film breakup time compared to the patient's tear film break up time prior to starting treatment using minocycline topical suspension. In certain embodiments, the method produces at least a 25% increase in tear film breakup time compared to the patient's tear film break up time prior to starting treatment using minocycline topical suspension. In certain embodiments, the method produces at least a 50% increase in tear film breakup time compared to the patient's tear film break up time prior to starting treatment using minocycline topical suspension.

In certain embodiments, said increase is achieved within twelve weeks after first administering the minocycline topical suspension. In certain embodiments, said increase is achieved within 4, 5, 6, 7, 8, 9 or 10 weeks after first administering the minocycline topical suspension.

Symptom Flares Due to Meibomian Gland Dysfunction

When treating meibomian gland dysfunction, the method may be further characterized according to the number of symptom flares due to meibomian gland dysfunction experienced by the patient after receiving the minocycline topical suspension. For example, in certain embodiments, the method produces a reduction in the number of symptom flares experienced by the patient per day due to meibomian gland dysfunction. In certain embodiments, as a result of the method, the average number of symptom flares experienced by the patient per day due to meibomian gland dysfunction is less than 2. In certain embodiments, as a result of the method, the average number of symptom flares experienced by the patient per day due to meibomian gland dysfunction is less than 1.

In certain embodiments, as a result of the method, the average number of symptom flares experienced by the patient per week due to meibomian gland dysfunction is less than 3. In certain embodiments, as a result of the method, the average number of symptom flares experienced by the patient per week due to meibomian gland dysfunction is less than 2. In certain embodiments, as a result of the method, the average number of symptom flares experienced by the patient per week due to meibomian gland dysfunction is less than 1.

In certain embodiments, as a result of the method, the average number of symptom flares experienced by the patient per month due to meibomian gland dysfunction is less than 50, 40, 30, 25, 20, 10, 5, or 1. In certain embodiments, as a result of the method, the average number of symptom flares experienced by the patient per month due to meibomian gland dysfunction is less than 10. In certain embodiments, as a result of the method, the average number of symptom flares experienced by the patient per month due to meibomian gland dysfunction is less than 4. In certain embodiments, as a result of the method, the average number of symptom flares experienced by the patient per month due to meibomian gland dysfunction is less than 2.

In certain embodiments, the method produces at least a 1%, 2%, 3%, 4%, 5%, 6%, 7%, 8%, 9%, 10%, 12%, 14%, 16%, 18%, 20%, 30%, 40%, 50%, 60%, 70%, 80%, 90%, or 100% reduction in the average number of symptom flares per day due to meibomian gland dysfunction compared to the average number of symptom flares per day prior to starting treatment using minocycline topical suspension. In certain embodiments, the method produces at least a 10% reduction in the average number of symptom flares per day due to meibomian gland dysfunction compared to the average number of symptom flares per day prior to starting treatment using minocycline topical suspension. In certain embodiments, the method produces at least a 50% reduction in the average number of symptom flares per day due to meibomian gland dysfunction compared to the average number of symptom flares per day prior to starting treatment using minocycline topical suspension.

In certain embodiments, the method produces at least a 1%, 2%, 3%, 4%, 5%, 6%, 7%, 8%, 9%, 10%, 12%, 14%, 16%, 18%, 20%, 30%, 40%, 50%, 60%, 70%, 80%, 90%, or 100% reduction in the average number of symptom flares per week due to meibomian gland dysfunction compared to the average number of symptom flares per week prior to starting treatment using minocycline topical suspension. In certain embodiments, the method produces at least a 10% reduction in the average number of symptom flares per week due to meibomian gland dysfunction compared to the average number of symptom flares per week prior to starting treatment using minocycline topical suspension. In certain embodiments, the method produces at least a 50% reduction in the average number of symptom flares per week due to meibomian gland dysfunction compared to the average number of symptom flares per week prior to starting treatment using minocycline topical suspension.

In certain embodiments, the method produces at least a 1%, 2%, 3%, 4%, 5%, 6%, 7%, 8%, 9%, 10%, 12%, 14%, 16%, 18%, 20%, 30%, 40%, 50%, 60%, 70%, 80%, 90%, or 100% reduction in the average number of symptom flares per month due to meibomian gland dysfunction compared to the average number of symptom flares per month prior to starting treatment using minocycline topical suspension. In certain embodiments, the method produces at least a 10% reduction in the average number of symptom flares per month due to meibomian gland dysfunction compared to the average number of symptom flares per month prior to starting treatment using minocycline topical suspension. In certain embodiments, the method produces at least a 50% reduction in the average number of symptom flares per month due to meibomian gland dysfunction compared to the average number of symptom flares per month prior to starting treatment using minocycline topical suspension.

In certain embodiments, said reduction is achieved within twelve weeks after first administering the minocycline topical suspension. In certain embodiments, said reduction is achieved within 4, 5, 6, 7, 8, 9 or 10 weeks after first administering the minocycline topical suspension.

Minocycline-Induced Hyperpigmentation of the Conjunctiva

Because minocycline-induced hyperpigmentation of the conjunctiva can occur as an adverse side effect when too large a dose of minocycline is administered to the patient's eye, the method can be further characterized according to number of occurrences of minocycline-induced hyperpigmentation of the conjunctiva. In certain embodiments, the patient experiences fewer than 1, 2, 3, 4, or 5 occurrences of minocycline-induced hyperpigmentation of the conjunctiva while receiving the minocycline topical suspension. In certain embodiments, the patient experiences no occurrences of minocycline-induced hyperpigmentation of the conjunctiva while receiving the minocycline topical suspension.

In certain embodiments, the foregoing occurrences of minocycline-induced hyperpigmentation of the conjunctiva is the sum of the occurrences that occurred over 2, 3, 4, 5, 6, 7, 8, 9 or 10 weeks of administering the minocycline topical suspension.

Minocycline-Induced Hyperpigmentation of the Retina

Because minocycline-induced hyperpigmentation of the retina can occur as an adverse side effect when too large a dose of minocycline is administered to the patient's eye, the method can be further characterized according to number of occurrences of minocycline-induced hyperpigmentation of the retina. In certain embodiments, the patient experiences fewer than 1, 2, 3, 4, or 5 occurrences of minocycline-induced hyperpigmentation of the retina while receiving the minocycline topical suspension. In certain embodiments, the patient experiences no occurrences of minocycline-induced hyperpigmentation of the retina while receiving the minocycline topical suspension.

In embodiments, the foregoing occurrences of minocycline-induced hyperpigmentation of the retina is the sum of the occurrences that occurred over 2, 3, 4, 5, 6, 7, 8, 9 or 10 weeks of administering the minocycline topical suspension.

5. Compositions for Medical Use

Minocycline topical suspensions described herein may be used to treat a medical condition described herein. The use may be according to a method described herein. For example, one aspect of the invention provides a minocycline topical suspension for use in treating meibomian gland dysfunction by topical administration to the eyelid margin of a patient in need thereof once or twice per day a dose of the minocycline topical suspension, wherein the dose provides from about 0.1 mg to about 1.4 mg of minocycline, and the minocycline topical suspension comprises:

a) minocycline in a suspended form within the topical suspension;
b) a liquid medium that dissolves less than 5% (w/w) of the minocycline at room temperature after two hours, wherein the liquid medium contains mineral oil; and
c) a polymeric hydrocarbon gelling agent;
wherein particles of minocycline in the topical suspension have a D90 particle size less than 8 microns, and the topical suspension comprises from about 0.1% (w/w) to about 2% (w/w) minocycline.

Embodiments described herein in connection with the methods for treatment may be applied in connection with the minocycline topical suspensions for use.

6. Preparation of a Medicament

Minocycline topical suspensions described herein may be used in the preparation of a medicament to treat a medical condition described herein. For example, one aspect of the invention provides for the use a minocycline topical suspension described herein in the preparation of a medicament treating meibomian gland dysfunction by topical administration to the eyelid margin of a patient in need thereof once or twice per day a dose of the minocycline topical suspension, wherein the dose provides from about 0.1 mg to about 1.4 mg of minocycline, and the minocycline topical suspension comprises:

a) minocycline in a suspended form within the topical suspension;
b) a liquid medium that dissolves less than 5% (w/w) of the minocycline at room temperature after two hours, wherein the liquid medium contains mineral oil; and
c) a polymeric hydrocarbon gelling agent; and
wherein particles of minocycline in the topical suspension have a D90 particle size less than 8 microns, and the topical suspension comprises from about 0.1% (w/w) to about 2% (w/w) minocycline.

Embodiments described herein in connection with the methods for treatment may be applied in connection with the minocycline topical suspensions for use in the preparation of a medicament.

II. Medical Kits

Another aspect of the invention provides a medical kit comprising, for example, (i) a composition described herein, and (ii) instructions for treating meibomian gland dysfunction according to methods described herein.

EXAMPLES

The invention now being generally described, will be more readily understood by reference to the following examples, which are included merely for purposes of illustrating certain aspects and embodiments of the present invention, and are not intended to limit the invention.

Example 1—Treatment of Meibomian Gland Dysfunction by Minocycline Topical Suspension in Human Subjects The ability of minocycline topical suspension to treat a human subject suffering from meibomian gland dysfunction was evaluated according to the clinical study described below in which minocycline topical suspension was administered to the eyelid margin of the patient, and then the patient was evaluated for improvement. Experimental procedures and results are described below.

Part I—Experimental Procedures

A. Study Summary

In order to evaluate the efficacy and safety of two strengths of minocycline topical suspension (Test Article) versus Vehicle administered twice daily for twelve weeks in subjects with a diagnosis of inflamed meibomian gland dysfunction, the following procedures are carried out.

The trial is structured as a multi-center, double-masked, randomized, vehicle-controlled, parallel-group study. Subjects are randomized into three groups: 0.3% BID Test Article, 1% BID Test Article or Vehicle BID in a 1:1:1 ratio. BID refers to twice daily administration.

Double-Masked Investigational Product (IP), which is 0.3% Test Article or 1% Test Article, is administered BID to both eyes for twelve weeks. Each dose is delivered using a fingertip, as an instillation of approximately ¼ inch strip (equivalent to approximately 50 µL drop) in each eye. IP is instilled to full eyelid margin. Subjects are instructed to wash hands thoroughly prior to administration of IP. Following administration of the IP, subjects are allowed to blot or clean the lower eyelid skin, if necessary.

At Visit 1 (Screening) informed consent is obtained from subjects and eligibility is determined. After the screening assessment, eligible subjects are entered into a 2-week Single-Masked Run-In period, during which a Single-Masked Vehicle BID is instilled in each eye.

At Visit 2 (Randomization/Baseline) eligibility is reconfirmed and subjects are randomly assigned to one of the three Double-Masked treatment groups (0.3% or 1% Test Article or Vehicle) and IP is instilled BID for twelve weeks. The randomization is stratified on the presence/absence of evaporative dry eye disease (DED) diagnosis. At Visit 3 (Week 2), Visit 4 (Week 4), Visit 5 (Week 8), and Visit 6 (Week 12) subjects attend clinic visits where efficacy and safety evaluations are performed. Treatment with Double-Masked IP is discontinued at Visit 6. Subjects who discontinue before Visit 6 undergo Visit 6 evaluations (at the Early Termination visit).

At Visit 7 (Week 16) Post-Treatment Follow-up Visit, efficacy and safety evaluations are performed.

Since the Vehicle is not color matched with the active product, there is a Dedicated Dosing Coordinator who is responsible for handling of IP and activities surrounding the use of IP. Further, the subjects are informed via the Informed Consent (IC) Process and document, that they will receive Vehicle at some unspecified time in the study. This supports masking efforts as the subjects are unable to differentiate which product is Vehicle and which is active.

B. Investigational Product (IP)

Test Article is supplied as a sterile ointment. Test Article is packaged in a 5 gm lacquer-lined aluminum tube with a nasal tip and a low density polyethylene cap closure. Subjects randomized to the Vehicle control arm receive the same tubes containing all components at the concentrations used in the Test Article except for the active component.

TABLE 1-A

Composition of 0.3% Test Article

| Component | Amount | Function |
| --- | --- | --- |
| Minocycline base | 0.3% w/w | active ingredient |
| Polymeric hydrocarbon gelling agent commercially available under the tradename VERSAGEL ® M-750 | 69.8% w/w | gelling agent |
| Mineral oil | 29.9% w/w | wetting agent |

TABLE 2-B

Composition of 1% Test Article

| Component | Amount | Function |
| --- | --- | --- |
| Minocycline base | 1% w/w | active ingredient |
| Polymeric hydrocarbon gelling agent commercially available under the tradename VERSAGEL ® M-750 | 69.3% w/w | gelling agent |
| Mineral oil | 29.7% w/w | wetting agent |

TABLE 3

Composition of Vehicle

| Component | Function |
| --- | --- |
| Polymeric hydrocarbon gelling agent commercially available under the tradename VERSAGEL ® M-750 | gelling agent |
| Mineral oil | wetting agent |

The minocycline base is minocycline base in crystalline Form II. The polymeric hydrocarbon gelling agent commercially available under the tradename VERSAGEL® M-750 is a mixture of ethylene-propylene-styrene copolymer, butylene-ethylene-styrene copolymer, butylated-hydroxytoluene, and mineral oil. The ethylene-propylene-styrene copolymer (e.g., weight-average molecular weight of about 200,000 g/mol) is present in an amount within the range of 2.5% to 10% (w/w), the butylene-ethylene-styrene copolymer (e.g., weight-average molecular weight of about 100,000 g/mol) is present in an amount within the range of 0.1% to 2.5% (w/w), the butylated-hydroxytoluene is present in an amount <0.5% (w/w), and the remainder is mineral oil (e.g., having a weight-average molecular weight in the range of 230-700 g/mol).

The Single-Masked Run-In product contains a tube of IP which is sufficient for 3-weeks of dosing. Each randomized, double-masked IP kit contains six tubes of IP, each sufficient for 3 weeks of dosing.

C. IP Dispensation Instructions

At Visit 1, (Day −14/Screening), subjects receive their first dose of Single-Masked Run-In product which is self-administered in the clinic under the supervision of the Dedicated Dosing Coordinator. IP is instilled to the full eyelid margin. Subjects are instructed to wash hands thoroughly prior to administration of IP. (Following administration of the IP, subjects are allowed to blot or clean the lower eyelid skin, if necessary.)

They then receive one tube of Run-In from a general supply to take home for self-administration. The tube of Single-Masked Run-In is returned to the site at Visit 2 (Day 1/Randomization).

At Visit 2, randomized subjects are assigned to an Investigational Product Kit which contains six tubes of Double-Masked IP (Test Article or Vehicle). The first dose of Double-Masked IP (Test Article or Vehicle) is self-administered in the clinic by the subject under the supervision of the Dedicated Dosing Coordinator. They then receive one tube of Double-Masked IP from their assigned kit to take home for self-administration. Subjects are instructed to apply IP to the full eyelid margin and to wash hands thoroughly prior to administration of IP as was the same at Visit 1.

Subjects will return the used tube of IP at Visit 3 and at Visit 3 will receive one new tube of IP which is returned at Visit 4. At Visits 4 and 5, subjects will receive two new tubes of IP at each visit which are returned at Visits 5 and 6, respectively. The Double-Masked box labels and the tubes will contain the following information: sponsor name, protocol number, kit number, storage temperature, and required statement(s) per the appropriate regulatory agency.

Test Article is stored at 20-25° C. (68-77° F.); excursions permitted between 15-30° C. (59-86° F.). IP is protected from light and moisture.

To minimize bias, the following measures are taken:
Investigational product allocation (Test Article versus Vehicle) is randomized and masked to the Sponsor, subjects, and select investigative staff The randomization schedule is generated by and independent unmasked statistician (who is not on the project team) or designee and maintained in a secure and limited-access location separate from the study Investigator and members of the project team.

To account for the use of a non-color matched Vehicle, a Dedicated Dosing Coordinator, who is otherwise uninvolved in study assessments, dispense the tube of investigational product to the subject and supervise the subjects' in clinic instilled dose.

To account for potential bias, the investigative staff should acknowledge and report any instance where unmasking may have occurred (outside of the dedicated dosing coordinator role). This report should include which individual(s) were involved (e.g., investigator, study coordinator, subject, monitor, etc.).

D. Timing of Self-Administration

At Visit 1, subjects self-administer the first dose of Single-Masked Run-In product in the clinic under the supervision of the Dedicated Dosing Coordinator. Subjects then self-administer additional doses of investigational product during the remainder of the Run-In period. At Visit 2, subjects self-administer their first dose of Double-Masked IP under the supervision of the Dedicated Dosing Coordinator. Subjects then self-administer additional doses of IP during the remainder of the study. It is recommended that visits be scheduled in the morning to allow subjects to receive the two daily doses 8 to 12 hours apart, with the AM dose occurring in the clinic for Visit 2/Day 1±2 days.

Subjects are asked to instill the first daily dose upon awakening and then the second daily dose approximately 8 to 12 hours later. The two daily doses are described as "Morning (AM) Dose" and "Evening (PM) Dose."

Following Visit 2, clinic visits are scheduled prior to the subject administration of their morning dose if possible. If the subject does take a dose, the visit is scheduled at least 2 hours following the morning dose to prevent the subject from being evaluated with residual investigational product on the eyelids.

E. Efficacy Endpoints

1. Primary Efficacy Endpoints

The primary endpoints of this study are evaluated using hierarchical statistical testing in the following sequence (Note: the analysis are performed on the intent-to-treat (ITT) population as well as a subset of subjects who meet the criteria for both inflamed meibomian gland dysfunction and evaporative dry eye disease):

Changes in Vascular Engorgement at the study eyelid margin as graded by the investigator at Week 12 (Visit 6) from Randomization/Baseline (Visit 2) in 1% Test Article compared to Vehicle Change in Eye Discomfort Visual Analogue Score (VAS) at Week 12 (Visit 6) from Randomization/Baseline (Visit 2) in 1% Test Article compared to Vehicle Changes in Vascular Engorgement at the study eyelid margin as graded by the investigator at Week 12 (Visit 6) from Randomization/Baseline (Visit 2) in 0.3% Test Article compared to Vehicle Change in Eye Discomfort VAS at Week 12 (Visit 6) from Randomization/Baseline (Visit 2) in 0.3% Test Article compared to Vehicle 2. Secondary Efficacy Endpoints The secondary endpoints of the study include:

Change in Fluorescein Corneal Staining (FCS) total score (NEI/Industry Workshop 0-15 scale) in the study eye at Week 4 (Visit 4), Week 8 (Visit 5), Week 12 (Visit 6), and Week 16 (Visit 7) from Randomization/Baseline (Visit 2).

Change in FCS inferior, nasal, and central combined score (NEI/Industry Workshop section 1, 4 and 5 with a 0-9 scale) in the study eye at Week 4 (Visit 4), Week 8 (Visit 5), Week 12 (Visit 6), and Week 16 (Visit 7) from Randomization/Baseline (Visit 2).

Change in FCS inferior score (NEI/Industry Workshop section 5 with a 0-3 scale) in the study eye at Week 4 (Visit 4), Week 8 (Visit 5), Week 12 (Visit 6), and Week 16 (Visit 7) from Randomization/Baseline (Visit 2).

Changes in Eye Discomfort Visual Analogue Score (VAS) at Week 4 (Visit 4), Week 8 (Visit 5), Week 12 (Visit 6), and Week 16 (Visit 7) from Randomization/Baseline (Visit 2).

Changes in Investigator-rated assessments of objective signs of meibomian gland dysfunction (MGD) including change from Randomization/Baseline (Visit 2) at each follow up visit using individual severity scores:
Vascular engorgement of the eyelid margin
Plugging of Meibomian Gland
Character of Secretion Expressed
Expressibility of the Meibomian Gland Changes in Investigator reported scores on objective signs of Meibomian Gland Dysfunction for Total Clinical Outcome Severity Score from Randomization/Baseline (Visit 2) defined as the sum of the four individual severity scores for the clinical signs of:
Vascular Engorgement of eyelid margin
Plugging of Meibomian Gland
Character of Secretion Expressed
Expressibility of the Meibomian Gland Changes in Investigator reported scores on objective Conjunctival Tarsal Erythema change from Randomization/Baseline (Visit 2) at each follow up visit.

Changes in Tear Film Break-Up Time (TFBUT) from Randomization/Baseline (Visit 2) at each follow up visit.

Changes in the following Dry Eye-related ocular symptoms at each follow-up visit:
VAS Scale Symptoms (other than eye discomfort):
Eye Dryness
Foreign Body Sensation
SANDE change in the square root of the product of the two questions at each timepoint compared to baseline and the change from baseline of each individual question within the SANDE The mean tear osmolarity score at each follow up visit compared to baseline. (This are evaluated at a subset of clinical sites.)

The proportion of subjects converting from positive point of care matrix metalloproteinase-9 (MMP-9) to negative point of care MMP-9 at Week 12 (Visit 6).

Number of symptom flares during the 12 weeks of treatment.

The change from baseline in the unanesthetized Schirmer score.

3. Safety Endpoints

Safety endpoints of the study include:
Adverse Event (AE) Monitoring
Best Corrected Visual Acuity (BCVA)
Slit Lamp Biomicroscopy and External Eye Exam
Intraocular Pressure (IOP) Measurement
Dilated Ophthalmoscopy
Follow-Up Assessment F. Selection of Subjects 1. Subject Inclusion Criteria At Visit 1, individuals of any gender or any race is eligible for study participation if they:
1. Have provided written informed consent prior to any study procedures.
2. Are 18 years of age or above.
3. Have a clinical diagnosis of moderate to severe MGD and who meet the following criteria, in a qualifying eyelid, at both Visit 1 (Screening) and Visit 2 (Randomization) examinations:
   a. Clinical sign severity score of at least 2 (moderate) on vascular engorgement at the eyelid margin and
   b. Clinical sign severity score of at least 2 (moderate) on plugging of the meibomian glands.
   c. Eye Discomfort Symptom score of ≥40 using VAS (0-100 point scale)
4. Meet the following criteria, in a qualifying eye (same eye that qualifies for Inclusion #3), at both the Visit 1 (Screening) and Visit 2 (Randomization) examinations:
   a. Fluorescein corneal staining (FCS) total score ≥3 in the inferior, central, and nasal region combined score (NEI/Industry Workshop sections 1, 4 and 5 with 0-9 scale)
   b. Schirmer score of >7 mm without topical anesthesia
5. Are willing and able to follow instructions and can be present for the required study visits for the duration of the study.
6. Have a BCVA, using corrective lenses if necessary, in both eyes of at least +0.7 as assessed by Early Treatment of Diabetic Retinopathy Study (ETDRS) or modified ETDRS.
7. If female, are non-pregnant, non-lactating and women of childbearing potential (WOCBP) must be using an acceptable method of birth control [e.g., an Intrauterine Contraceptive Device (IUCD) with a failure rate of <1%, hormonal contraceptives, or a barrier method] for the duration of the study. If a female subject is currently abstinent, they must agree to use one of the acceptable methods of birth control before they become sexually active.

2. Subject Exclusion Criteria

In order for subjects to be eligible at Visit 1 they may not:
1. Have presence of inflammation and/or active structural change in the iris or anterior chamber.
2. Have lid structural abnormalities such as entropion or ectropion.
3. In the eyelid that qualifies (based on Inclusion #3), have grade level 4 (Obstructed) on Character of Secretion of Meibomian Glands or grade level 4 (No glands are expressible) on the Expressibility of Meibomian Glands.
4. Subjects with ocular inflammatory conditions (e.g., conjunctivitis, keratitis, anterior blepharitis, etc.) not related to MGD.
5. Subjects who have FCS total score=15 or a score=3, in either eye, in the superior region NEI/Industry Workshop scale or subjects who have FCS with diffuse confluent staining, filaments or frank epithelial defects.
6. Have suspected ocular fungal, viral or bacterial infection.
7. Have had penetrating intraocular surgery in the past 90 days or require penetrating intraocular surgery during the study.
8. Have had ocular surface surgery within 12 months of Visit 1 (e.g., LASIK, refractive, pterygium removal).
9. Subjects who within the past 90 days have had cauterization of the punctum or changes to the status (insertion or removal) of punctal plug(s) before the Screening Visit.
10. Have used topical ocular or oral antibiotics within 30 days of the study or expect to use during the study.
11. Have used LipiFlow or hypochlorous acid spray within 30 days of the study or expect to use during the study.
12. If using inhaled or intranasal corticosteroids, unable to maintain a stable dose for the duration of the study.
13. Have ever used isotretinoin.
14. If using Omega-3 supplements, dose must be stable for 3 months prior to Visit 1 and for the duration of the study.
15. Have used topical cyclosporine within 30 days of the study or during the study.
16. Have used topical lifitegrast within 30 days of the study or during the study.
17. Have used systemic corticosteroids within 30 days prior to study entry or during study participation.
18. Have used topical ocular corticosteroids or ocular non-steroidal anti-inflammatory drugs (NSAIDs) within 30 days prior to study entry and during study participation.
19. Have used topical ocular antihistamine and/or mast cell stabilizers within 30 days prior to study entry or during study participation.
20. Are unable or unwilling to discontinue using any preserved or unpreserved topical ocular medications (including artificial tears) upon Screening and for the duration of the study.
21. Are unwilling to discontinue use of contact lenses during the study.
22. Are unwilling to discontinue use of cosmetic makeup applied to the eyelids or eye lashes at the Screening Visit and during the study. If makeup was used, it should be removed at least 12 hours prior to the Visit 1.
23. Have a known hypersensitivity to minocycline, any other tetracycline antibiotic, or to any of the other ingredients in the investigational product.
24. Are unable or unwilling to withhold the use of eyelid scrubs or use of mechanical therapy during the study.
25. Have been diagnosed with glaucoma or are currently using any glaucoma medication.
26. Have a history of herpetic keratitis.
27. Have a concomitant ocular pathology other than condition under study assessed as potentially confounding by the investigator.
28. Have a serious systemic disease or uncontrolled medical condition that in the judgment of the investigator could confound study assessments or limit compliance.
29. Have been exposed to any investigational drug or investigational device within the preceding 30 days.
30. Are an employee of the site that is directly involved in the management, administration, or support of this study or be an immediate family member of the same.
31. Have trigger factors including conjunctivochalasis, allergic conjunctivitis, contact lens intolerance, trichiasis, epithelial basement membrane dystrophy, infectious keratitis or conjunctivitis
32. Have a documented history of ocular allergies, which, in the judgment of the investigator, are likely to have an acute increase in severity due to the expected timing of the exposure to the allergen to which the subject is sensitive. Subjects sensitive to seasonal allergens that are not expected to be present during the study are permitted.

3. Study Eye Selection

The study eye is the eye with the eyelid at Visit 2, having the worst (higher) score defined as the sum of the following two severity scores for the clinical signs of Meibomian Gland Disease (Note, the study eye and eyelid must have met qualifying eligibility criteria at Visit 1 and Visit 2):
1. Vascular Engorgement of eyelid margin
2. Plugging of the Meibomian Gland If both eyes, and eyelids, have the same score, then the right eye and upper eyelid is selected.

G. Randomization

At the Randomization Visit (Visit 2), an eligible subject must continue to meet all clinical inclusion/exclusion criteria as defined above. Subjects must meet all criteria from Visit 1 and inflamed MGD criteria in the same qualifying eye and/or qualifying eyelid as in Visit 1. Further, subjects must be 80% compliant with respect to dosing of Run-In IP and diary completion.

Randomization is stratified by absence and presence of evaporative DED in the study eye (identified prior to randomization). A clinical diagnosis of evaporative DED in the study eye, is defined as meeting the following criteria at Visit 2 (Randomization/Baseline):
1. Fluorescein corneal staining (FCS) total score ≥6 in the inferior, central, and nasal region combined score (NEI/Industry Workshop section 1, 4 and 5 with 0-9 scale) and
2. Symptom Severity score of ≥50 using the SANDE questionnaire H. Visit Descriptions Written Informed Consent and Health Insurance Portability and Accountability Act (HIPAA) authorization are obtained from all subjects prior to any study procedures being performed. Visit assessments are performed in the order suggested in both eyes.

1. Visit 1 (Screening): 14 (+2) Days Prior to Visit 2

The following is performed/assessed in the order suggested below and in both eyes:
Explain the purpose and conduct of the study to the subject, answer the subject's questions, and obtain written informed consent.
Obtain information including: demographics, concomitant medications, ocular and systemic medical and medication history and surgical history.
A Screening ID is assigned to the Subject once any Visit 1 procedures are performed.
Subject Rated Symptom Assessments (in this order):
 1. Individual Symptom Assessment via VAS
 2. SANDE
For all eligible women of childbearing potential, perform a urine pregnancy test (UPT) to confirm that the subject is not pregnant.
BCVA
Tear Osmolarity (conducted at a subset of sites)
External Eye Exam
Slit-lamp biomicroscopy
Investigator-rated assessment of Meibomian Gland Dysfunction (in both eyes for upper and lower lids)
 See Section N. Assessment of Efficacy for full description of investigator-rated assessments for objective signs of change from baseline using five individual severity scores TFBUT
FCS (NEI/Industry Workshop scale)
Unanesthetized Schirmer test
Wait 10 minutes prior to MMP-9 Assessment
MMP-9 Point of Care Assessment
IOP
Dilated Ophthalmoscopy
Determine if the subject is eligible to continue in the study. Do not continue screening any subject who does not meet eligibility requirements. Any subject who does not meet eligibility requirements are designated as a Screen Failure.
Instruct the subject to discontinue using all ophthalmic medications that he/she had been using before the screening visit. Remind the subject that they are not to use artificial tears or any other OTC or prescription or any other topical eye medication other than the investigational drug they have been given during the remainder of the study.
If the subject is qualified, a three-week supply of Single-Masked Vehicle IP is dispensed.
The first dose of IP is taken in the clinic under the supervision of a designated Dosing Coordinator. This Dosing Coordinator, who is not responsible for study assessments, is required to dispense and retrieve investigational product to/from the subjects and dispense investigational product dosing instructions and daily dosing diaries. The following is the process regarding administration of investigational product whereby the Dosing Coordinator conducts the following procedures:
Explain the proper method of investigational product administration. Subjects are instructed to thoroughly wash their hands prior to administration of IP.
Following administration of the IP, subjects are allowed to blot or clean the lower eyelid skin, if necessary.
Observe subject instillation of first dose of Single-Masked IP
Assess for occurrence of any IP related AEs
Dispense Single-Masked Vehicle IP to the subject.
Dispense Daily Dosing Diary (without symptom exacerbation question)
Give the subject instructions to instill IP in each eye, BID and to record each administration on the daily dosing diary.
Schedule the subject to return for Visit 2 (Randomization), Day 1-14 days later plus or minus 2 days.
Remind subjects to withhold their morning dose prior to attending the next clinic visit. If subject forgets to withhold the dose prior to the clinic visit, the ocular clinical assessments are scheduled at least 2 hours following the dose to prevent the subject from being evaluated with residual investigational product on the eyelids.

2. Visit 2 (Randomization): Day 1 (+2 Days)

Visit 2 occurs 14 (±2) days after Visit 1 (Screening). The following is performed/assessed in both eyes:
Subject Rated Symptom Assessments (in this order):
 1. Individual Symptom Assessment via VAS
 2. SANDE
Subject is asked the following question regarding symptom flare experienced the day prior to the visit:
 During the prior day, did you experience any discrete and severe episodes of eye discomfort (related to your MGD) lasting more than a minute, and if so, how many episodes?
Use of any concomitant medications since the last visit
Occurrence of any AEs since the last visit Compliance is assessed via review of the daily dosing information recorded by the subject. Subjects must be 80% compliant with respect to dosing and diary completion for eligibility.

BCVA

Tear Osmolarity (at a subset of sites)

External Eye Exam

Slit-lamp biomicroscopy

Investigator-rated assessment of signs of Meibomian Gland Dysfunction (in both eyes for upper and lower lids)

See Section N. Assessment of Efficacy for full description of investigator-rated assessments for objective signs of change from baseline using five individual severity scores

TFBUT

FCS (NEI/Industry Workshop scale)

Unanesthetized Schirmer test

IOP

Determine if subject is eligible for randomization

Enter subject information into IWRS to determine randomization code and Kit Number For eligible subjects, the following is the process regarding administration of Double-Masked IP whereby the Dosing Coordinator conducts the following procedures:

Receive, weigh and record weight of returned Single-Masked IP dispensed at Visit 1

Observe subject instillation of first dose of AM self-administration of Double-Masked IP Following administration of the investigational product, subjects are allowed to blot or clean the lower eyelid skin, if necessary.

Assess for occurrence of any IP related AEs

Dispense 1 tube of Double-Masked IP to the subject.

Collect Daily Dosing diary (without symptom exacerbation question)

Dispense Daily Dosing Diary (with symptom exacerbation question)

Give the subject instructions to instill IP in each eye, BID and to record each administration on the daily dosing diary.

Schedule the subject to return for Visit 3 (Day 15 plus or minus 2 days).

Remind subjects to withhold their morning dose prior to attending the next clinic visit. If subject forgets to withhold the dose prior to the clinic visit, the ocular clinical assessments are scheduled at least 2 hours following the dose to prevent the subject from being evaluated with residual investigational product on the eyelids.

Remind subjects to bring their IP and diaries to the next visit.

3. Visit 3: Day 15 (+2 Days)

This visit occurs on Day 15 as calculated from Visit 2: Day 1, and the following is performed in both eyes:

Subject Rated Symptom Assessments (in this order):
1. Individual Symptom Assessment via VAS
2. SANDE Use of any concomitant medications since the last visit Occurrence of any AEs since the last visit

BCVA

Tear Osmolarity (at a subset of sites)

External Eye Exam

Slit-lamp biomicroscopy

Investigator-rated assessment of signs of Meibomian Gland Dysfunction

See Section N. Assessment of Efficacy for full description of investigator-rated assessments for objective signs of change from baseline using five individual severity scores

TFBUT

FCS (NEI/Industry Workshop scale)

IOP

The following is the process regarding administration of Double-Masked IP whereby the Dosing Coordinator conducts the following procedures:

Compliance is assessed via review of the daily dosing information recorded by the subject.

Receive, weigh and record weight of returned Double-Masked IP dispensed at Visit 2.

Dispense one tube of Double-Masked IP to the subject from their assigned kit.

Collect Daily Dosing Diary (with symptom exacerbation question).

Dispense Daily Dosing Diary (with symptom exacerbation question).

Schedule the subject to return for Visit 4 (Day 29 plus or minus 2 days).

Remind subjects to withhold their morning dose prior to attending the next clinic visit. If subject forgets to withhold the dose prior to the clinic visit, the ocular clinical assessments are scheduled at least 2 hours following the dose to prevent the subject from being evaluated with residual investigational product on the eyelids.

4. Visit 4: Day 29 (+2 Days)

This visit occurs on Day 29 as calculated from Visit 2: Day 1, and the following is performed in both eyes:

For all eligible women of childbearing potential, perform a urine pregnancy test to confirm that the subject is not pregnant.

Subject Rated Symptom Assessments (in this order):
1. Individual Symptom Assessment via VAS
2. SANDE Use of any concomitant medications since the last visit Occurrence of any AEs since the last visit

BCVA

Tear Osmolarity (at a subset of sites)

External Eye Exam

Slit-lamp biomicroscopy

Investigator-rated assessment of signs of Meibomian Gland Dysfunction

See Section N. Assessment of Efficacy for full description of investigator-rated assessments for objective signs of change from baseline using five individual severity scores

TFBUT

FCS (NEI/Industry Workshop scale)

TOP

The following is the process regarding administration of Double-Masked IP whereby the Dosing Coordinator conduct the following procedures:

The Dosing Coordinator reviews compliance of the daily dosing information recorded by the subject.

Receive, weigh and record weight of returned Double-Masked IP dispensed at Visit 3.

Dispense two tubes of Double-Masked IP to the subject from their assigned kit.

Collect Daily Dosing Diary (with symptom exacerbation question.)

Dispense Daily Dosing Diary (with symptom exacerbation question).

Schedule the subject to return for Visit 5 (Day 57 plus or minus 2 days).

Remind subjects to withhold their morning dose prior to attending the next clinic visit. If subject forgets to withhold the dose prior to the clinic visit, the ocular clinical assessments are scheduled at least 2 hours following the dose to prevent the subject from being evaluated with residual investigational product on the eyelids.

5. Visit 5: Day 57 (+2 Days)

This visit occurs on Day 57 as calculated from Visit 2: Day 1, and the following is performed in both eyes:

Subject Rated Symptom Assessments (in this order):
  1. Individual Symptom Assessment via VAS
  2. SANDE
Use of any concomitant medications since the last visit
Occurrence of any AEs since the last visit
BCVA
Tear Osmolarity (at a subset of sites)
External Eye Exam
Slit-lamp biomicroscopy
Investigator-rated assessment of signs of Meibomian Gland Dysfunction
  See Section N. Assessment of Efficacy for full description of investigator-rated assessments for objective signs of change from baseline using five individual severity scores
TFBUT
FCS (NEI/Industry Workshop scale)
IOP The following is the process regarding administration of Double-Masked IP whereby the Dosing Coordinator conduct the following procedures:

Compliance is assessed via review of the daily dosing information recorded by the subject
Receive, weigh and record weight of returned Double-Masked IP dispensed at Visit 4 (two tubes).
Dispense two tubes Double-Masked IP to the subject.
Collect Daily Dosing Diary (with symptom exacerbation question).
Dispense Daily Dosing Diary (with symptom exacerbation question).
Schedule the subject to return for Visit 6 (Day 85 plus or minus 2 days).
Remind subjects to withhold their morning dose prior to attending the next clinic visit. If subject forgets to withhold the dose prior to the clinic visit, the ocular clinical assessments are scheduled at least 2 hours following the dose to prevent the subject from being evaluated with residual investigational product on the eyelids.

6. Visit 6 (End of Treatment): Day 85 (+2 Days)

This visit occurs on Day 85 as calculated from Visit 2: Day 1, and the following is performed in both eyes:

UPT
Subject Rated Symptom Assessments (in this order):
  1. Individual Symptom Assessment via VAS
  2. SANDE
Use of any concomitant medications since the last visit
Occurrence of any AEs since the last visit
BCVA
Tear Osmolarity (at a subset of sites)
External Eye Exam
Slit-lamp biomicroscopy
Investigator-rated assessment of signs of Meibomian Gland Dysfunction
  See Section N. Assessment of Efficacy for full description of investigator-rated assessments for objective signs of change from baseline using five individual severity scores
TFBUT
FCS (NEI/Industry Workshop scale)
Unanesthetized Schirmer test
Wait 10 minutes prior to MMP-9 point of care test
MMP-9 point of care test
IOP
Dilated Ophthalmoscopy The following is the process regarding administration of Double-Masked IP whereby the Dosing Coordinator conduct the following procedures:

Compliance is assessed via review of the daily dosing information recorded by the subject.
Collect Used/Unused Double-Masked IP. Weigh and record weight of used IP (two tubes). Subject discontinues use of all IP following this visit.
Collect Daily Dosing Diary (with symptom exacerbation question)
Schedule the subject to return for Visit 7 (Day 113 plus or minus 2 days).

7. Visit 7 (Post-Treatment Follow-Up): Day 113 (+2 Days)

This visit occurs on Day 113 as calculated from Visit 6 (End of Treatment), and the following is performed in both eyes:

UPT
Subject Rated Symptom Assessments:
  1. Individual Symptom Assessment via VAS
  2. SANDE
Use of any concomitant medications since the last visit
Occurrence of any AEs since the last visit
BCVA
Tear Osmolarity (at a subset of sites)
External Eye Exam
Slit-lamp biomicroscopy
Investigator-rated assessment of signs of Meibomian Gland Dysfunction
TFBUT
FCS (NEI/Industry Workshop scale)
Unanesthetized Schirmer test
IOP
The subject may be discharged from the study at this visit.

8. Unscheduled Visit

Any visits or procedures performed beyond those specified within the protocol must be documented in the Unscheduled Visit pages of the electronic case report form (eCRF). Unscheduled visits may include but are not limited to reporting AEs, changes in concomitant medications, or ophthalmic assessments as deemed appropriate by an appropriately qualified physician.

9. Early Termination Visit

In the event of termination prior to Visit 6, every attempt is made to ensure that all the following Visit 6 assessments are performed in both eyes at the Early Termination Visit prior to discharge from the study:

Subject Rated Symptom Assessments: SANDE and Individual Symptom Assessment via VAS
Use of any concomitant medications since the last visit
Occurrence of any AEs since the last visit
Used and unused IP collected and compliance assessed via the daily dosing information recorded by the subject
UPT
BCVA
External Eye Exam
Slit lamp biomicroscopy Investigator-rated assessment of Meibomian Gland Dysfunction
Tear Osmolarity (at a subset of sites)
TFBUT
FCS (NEI/Industry Workshop scale)
Unanesthetized Schirmer test
Wait 10 minutes prior to MMP-9 point of care test
MMP-9 point of care test
IOP measurement
Dilated Ophthalmoscopy Include subject withdrawal criteria (i.e., terminating investigational product treatment/trial treatment).

I. Subject Withdrawal and/or Discontinuation

Any subject who wishes to discontinue IP use or withdraw from participation in the study for any reason is entitled to do so without obligation. The Investigator may also discontinue any subject from investigational product use or from study participation, if deemed necessary.

Investigational product use may be discontinued, and any subject may be discontinued from study participation at any time during the study at the discretion of the Investigator or the Sponsor for any reason including but not limited to:

1. Occurrence of any medical condition or circumstance that exposes the subject to substantial risk and/or does not allow the subject to adhere to the requirements of the protocol.

2. Any Serious Adverse Event (SAE), clinically significant AE, severe laboratory abnormality, intercurrent illness, or other medical condition that indicates to the Investigator that continued participation is not in the best interest of the subject.

3. Subject's decision to withdraw.

4. Any woman who becomes pregnant while participating in the study. Information on the pregnancy and outcome is requested.

5. Subject's failure to comply with protocol requirements or study related procedures.

6. Termination of the study by the Sponsor, FDA, or other regulatory authorities.

In the event study discontinuation of a randomized subject is necessary, the Investigator should make every attempt to have the subject complete Visit 6 assessments as possible. If a non-serious AE is unresolved at the time of the subject's final study visit, an effort is made to follow up until the AE is resolved or stabilized, the subject is lost to follow-up, or there is some other resolution of the event. The Investigator should make every attempt to follow all SAEs to resolution. The reason for premature discontinuation is entered into the eCRF and recorded in the subject chart.

Subjects who withdraw from the study are not replaced.

Additionally, the trial or parts of the trial may be discontinued by the Sponsor or at the recommendation of the Investigator after consultation with Hovione Scientia, Ltd. This may be based on a significant number of AEs of a similar nature that warrant such action.

J. Collection of Data

Source documentation for data collected in this study is maintained at the investigative site. In cases where no source is used (e.g., dosing diary), it is noted in the Investigator files.

K. Treatment of Subjects

1. Investigational Products to be Administered

All subjects meeting eligibility criteria at Visit 1 is provided with a Single-Masked Run-In product (Vehicle). One tube of Run-In is allocated to each subject at Visit 1 and returned at Visit 2. All subjects meeting Randomization criteria at Visit 2 are randomized to either Test Article or Vehicle. A 3-week supply (one tube) of randomized Double-Masked IP is allocated to each subject at Visit 2 for self-administration. The used tube of IP is returned to the site at Visit 3 and at Visit 3 the subjects receive one new tube of IP which is returned at Visit 4. At Visits 4 and 5, subjects receive two new tubes of IP at each visit which is returned at Visits 5 and 6, respectively. The IP is stored at the site in a secure area with limited access at controlled room temperature (20-25° C. [68-77° F.] with excursions permitted between 15-30° C. [59-86° F.]).

Subjects are asked to administer IP BID. It is important that IP is instilled to full eyelid margin. Subjects are instructed to wash hands thoroughly prior to administration of IP.

(Following administration of the IP, subjects are allowed to blot or clean the lower eyelid skin, if necessary.)

The subjects record the date and time of administration of each dose of IP at the time of instillation in a dosing diary. Compliance with instillation of investigational product is reviewed and assessed at Visits 2 through Visit 6.

2. Concomitant Medications

All medications that the subject has taken 60 days prior to Visit 1 and through Visit 7 or discontinuation from the study is recorded in the eCRF and the subject chart. The generic name of the drug, dose, route of administration, duration of treatment (including start and stop dates), frequency, indication, and whether or not the medication was taken due to an AE are recorded for each medication. Medications and therapies not specifically excluded below may be taken as necessary. Omega-3 supplements are permitted if the dose is stable within 3 months of Visit 1. Inhaled or intranasal corticosteroids are permitted if the dose is stable for the duration of the study.

The following procedures and medications are not allowed for the time periods specified:

Previous use of isotretinoin is not permitted.

Within 12 months prior to Screening (Visit 1) and for the duration of the study:
  Have had ocular surface surgery (e.g., LASIK, refractive, pterygium removal).

Within 90 days prior to Screening (Visit 1) and for the duration of the study:
  Have had or require penetrating intraocular surgery during the study
  Have had or require cauterization of the punctum or changes in the status of punctal plugs Within 30 days prior to Screening (Visit 1) and for the duration of the study:
  Systemic corticosteroids
  Topical ocular corticosteroids or ocular non-steroidal anti-inflammatory drugs (NSAIDs)
  Topical ocular or oral antibiotics
  Topical ocular antihistamines or mast cell stabilizers
  Any investigational drug
  Topical cyclosporine (RESTASIS®)
  Topical lifitegrast (XIIDRA®)
  LipiFlow
  Hypochlorous Acid Spray From Visit 1 (Screening/Randomization) and for the duration of the study:
  Preserved or unpreserved topical ocular medications including artificial tears
  Any glaucoma medications
  Eyelid scrubs or use of mechanical therapy 3. Investigational Product Use Compliance Compliance is assessed by comparing investigational product accountability records with the dosing information recorded daily by the subject. The Dedicated Dosing Coordinator documents this comparison along with verification of returned used investigational product tubes. The number of missed doses as assessed at each clinic visit is documented in the eCRF.

L. Drug Accountability

Sponsor study monitors or designees conduct accountability of investigational product (Test Article or Vehicle). Accountability is ascertained by performing reconciliation between the number of kits/tubes sent to the site and those accounted for at the time of reconciliation during routine monitoring and at the end of the study.

M. Maintenance of Randomization and Procedure for Breaking the Code

The Sponsor, the project teams at the designated Contract Research Organizations (CROs), and investigative staff responsible for assessments of study endpoints are masked to investigational product assignments. A designated dosing coordinator, who is not responsible for study assessments, is required to dispense and retrieve double-masked, investigational product and daily dosing diaries to the subjects. In case of medical emergency, or occurrence of an SAE, the randomization code may be unmasked and made available to the Investigator, Sponsor, and/or other personnel involved in the monitoring or conduct of this study. In the absence of medical need, the randomization code is not available to the above individuals until after the study is completed and the database is locked.

In the event of a medical need, the Investigator treats each subject as needed. Since there is no specific antidote to Test Article, immediate emergency unmasking is not necessary. If the Investigator feels it is necessary to unmask a subject's assignment after an emergency situation, the Investigator may call the medical monitor and notify the Sponsor. The investigational product assignment is revealed on a subject-by-subject basis with the approval of the medical monitor and Sponsor, thus leaving the masking of the remaining subjects intact.

A randomization code is computer-generated by the Sponsor or designee. Randomization team members work independently of other team members at the CRO. Study personnel, study subjects, the Sponsor, and project teams at the CROs involved in the study are masked to investigational product assignments.

N. Assessment of Efficacy

Efficacy assessments include the following:

1. Symptom Assessment in Dry Eye (SANDE)

The SANDE questionnaire is assessed at each visit. The subject is asked the following questions regarding the frequency and severity of their dry eye symptoms:

1. Frequency of Symptoms:
Please place a vertical mark on the line to indicate how often, on average, your eyes feel dry and/or irritated:
Rarely_All the time 2. Severity of Symptoms:
Please place a vertical mark on the line to indicate how severe, on average, you feel your symptoms of dryness and/or irritation are:
Very Mild_Very Severe 2. Individual Symptom Assessments Via VAS Subjects are asked the following questions regarding their current symptoms (unrelated to study drug instillation) at each visit. The subject is asked to subjectively rate each ocular symptom (OU) by placing a vertical mark on the horizontal line to indicate the level of discomfort. 0 corresponds to "No Symptoms" and 100 corresponds to "Severe Symptoms"

Subject Instructions: Please review the symptoms below. After your review, please rate how your eyes feel for each of the following symptoms by placing a single vertical mark that represents how your symptom feels at this moment.

| | | |
|---|---|---|
| Eye Discomfort | 0 |_____| 100 |
| Foreign Body Sensation (grain of sand/grittiness) | 0 |_____| 100 |
| Eye Dryness | 0 |_____| 100 |

0 = No Symptoms and 100 = Severe Symptoms

3. Patient Reports of MGD Flare (Assessed Via Daily Dosing Diary with Symptom Flare Question)

Subjects are asked to record each day the following information related to administration of investigational product:

Date
Time of Administration
Symptom Exacerbation Question (see below)
Symptom Flare Question: Each evening, the subject is asked to respond to the following question:
During the day, did you experience any discrete and severe episodes of eye discomfort (related to your MGD) lasting more than a minute, and if so, how many episodes?
No=0
Yes, how many (circle number)? 1, 2, 3, 4, More than 4

4. Tear Osmolarity Assessment

Tear osmolarity is collected at each visit at a subset of clinical sites. Tear osmolarity is an objective measurement of the salinity and its concentration in an individual's tears. The mean tear osmolarity score is obtained at each visit. Tear osmolarity is checked in a well-controlled environment. An osmometer takes a sample of tears from an individual using the osmolarity test pen with the attached card. A sample from each eye is collected by carefully pressing the card against a non-iris portion of the eye. The osmolarity card is entered into the Osmolarity System.

Figure 7:
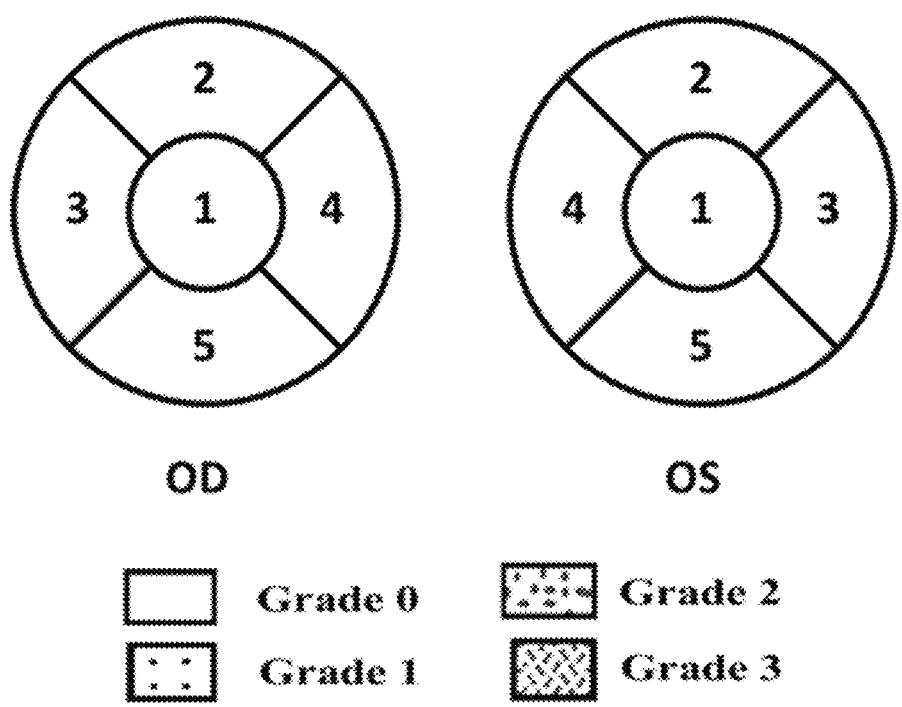
FIG. 7 depicts a diagram illustrating regions of a patient's eye assessed using Fluorescein Corneal Staining to determine corneal damage.
Figure 8:
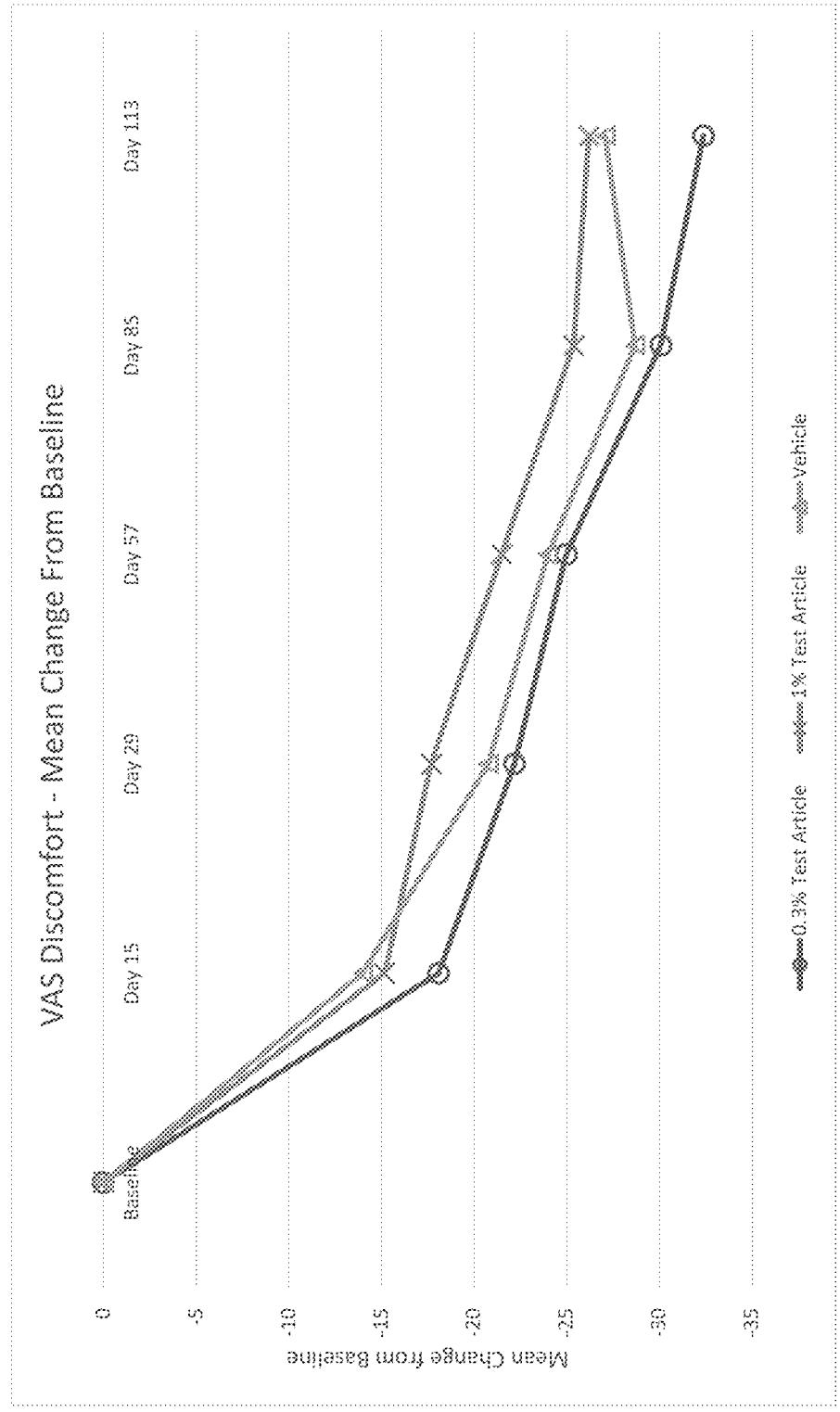
FIG. 8 is a line graph depicting VAS discomfort (mean change from baseline) results from the clinical study in Example 1.
Figure 9:
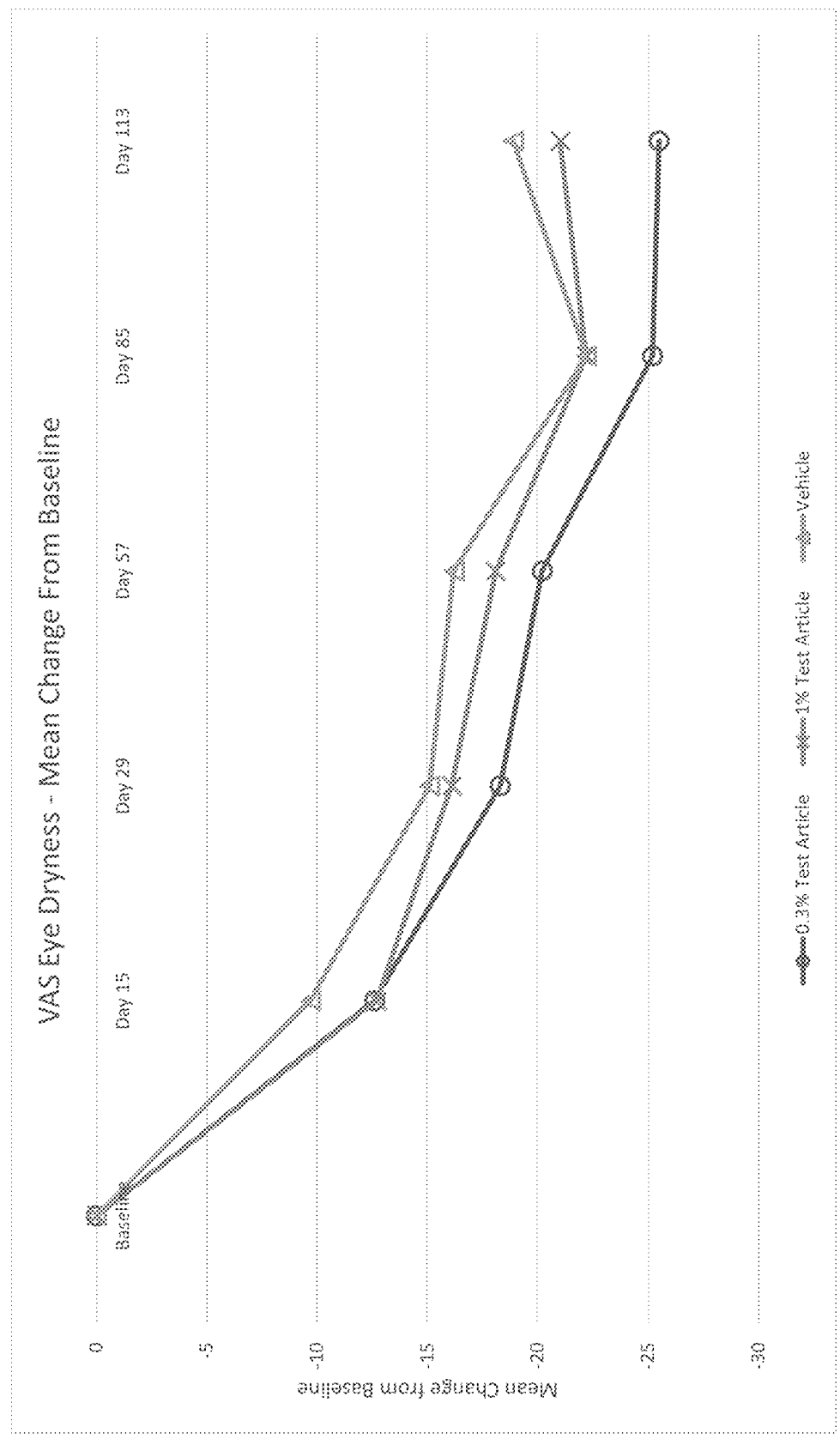
FIG. 9 is a line graph depicting VAS eye dryness (mean change from baseline) results from the clinical study in Example 1.
Figure 10:
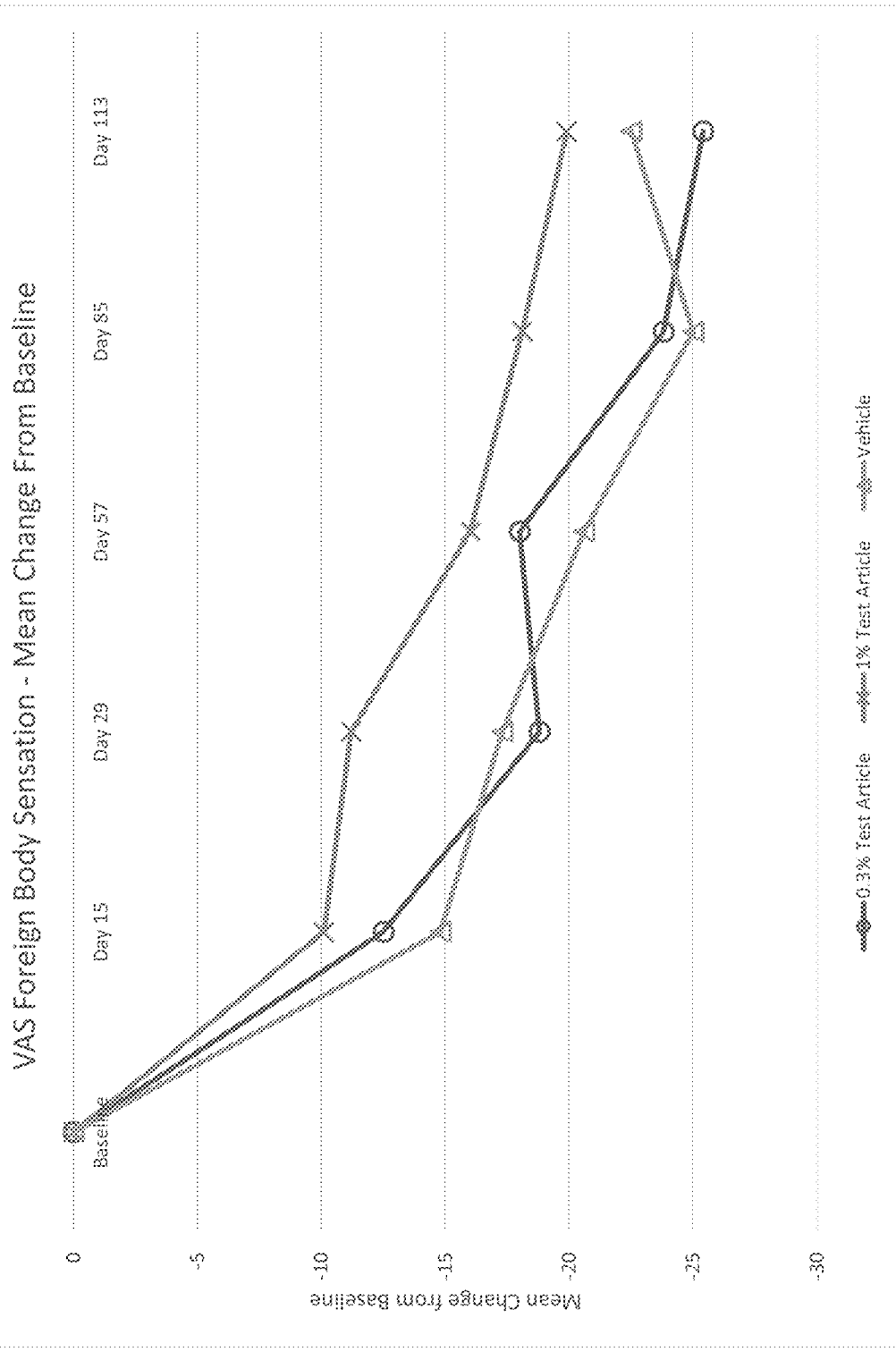
FIG. 10 is a line graph depicting VAS foreign body sensation (mean change from baseline) results from the clinical study in Example 1.
Figure 11:
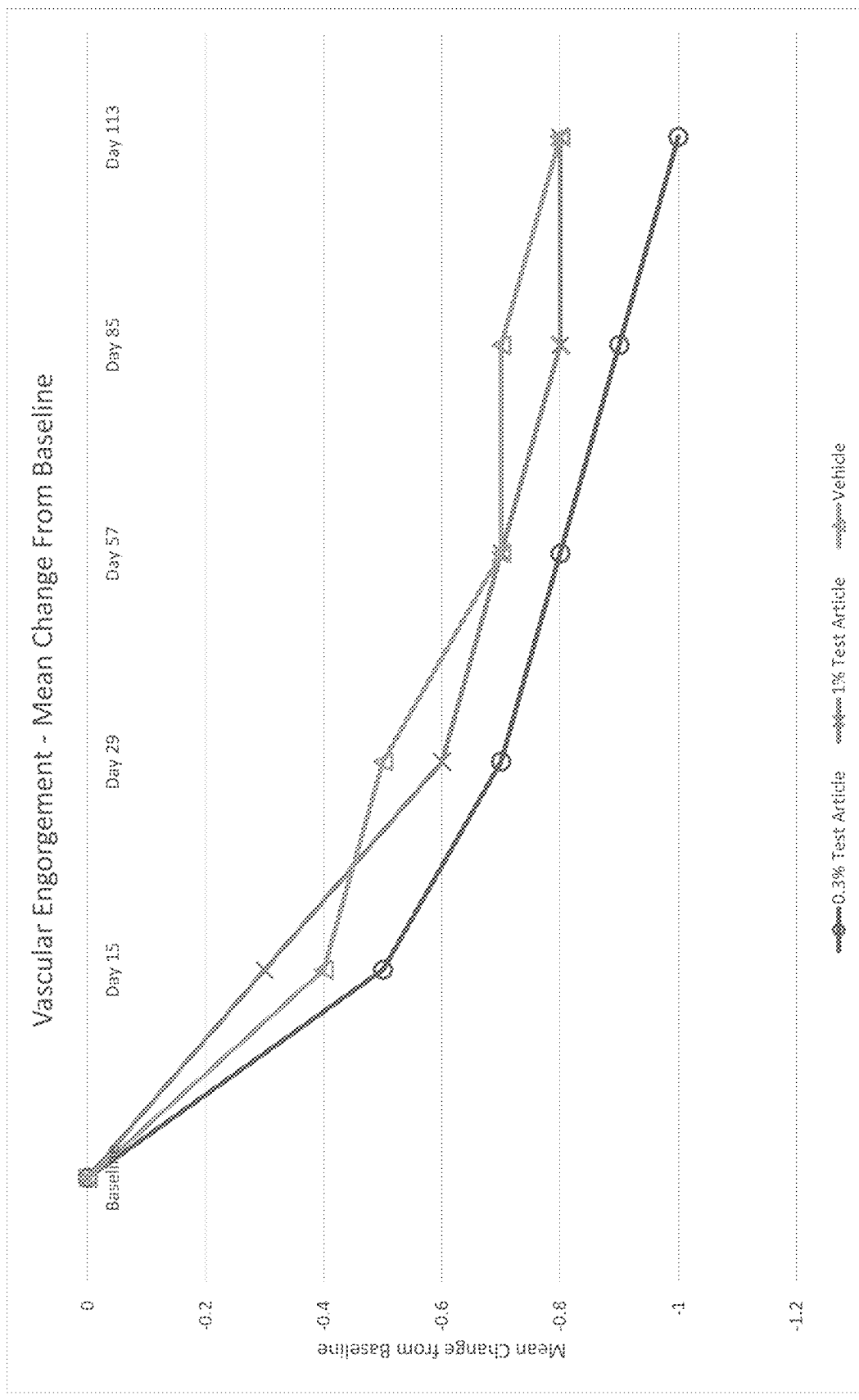
FIG. 11 is a line graph depicting vascular engorgement (mean change from baseline) results from the clinical study in Example 1.
Figure 12:
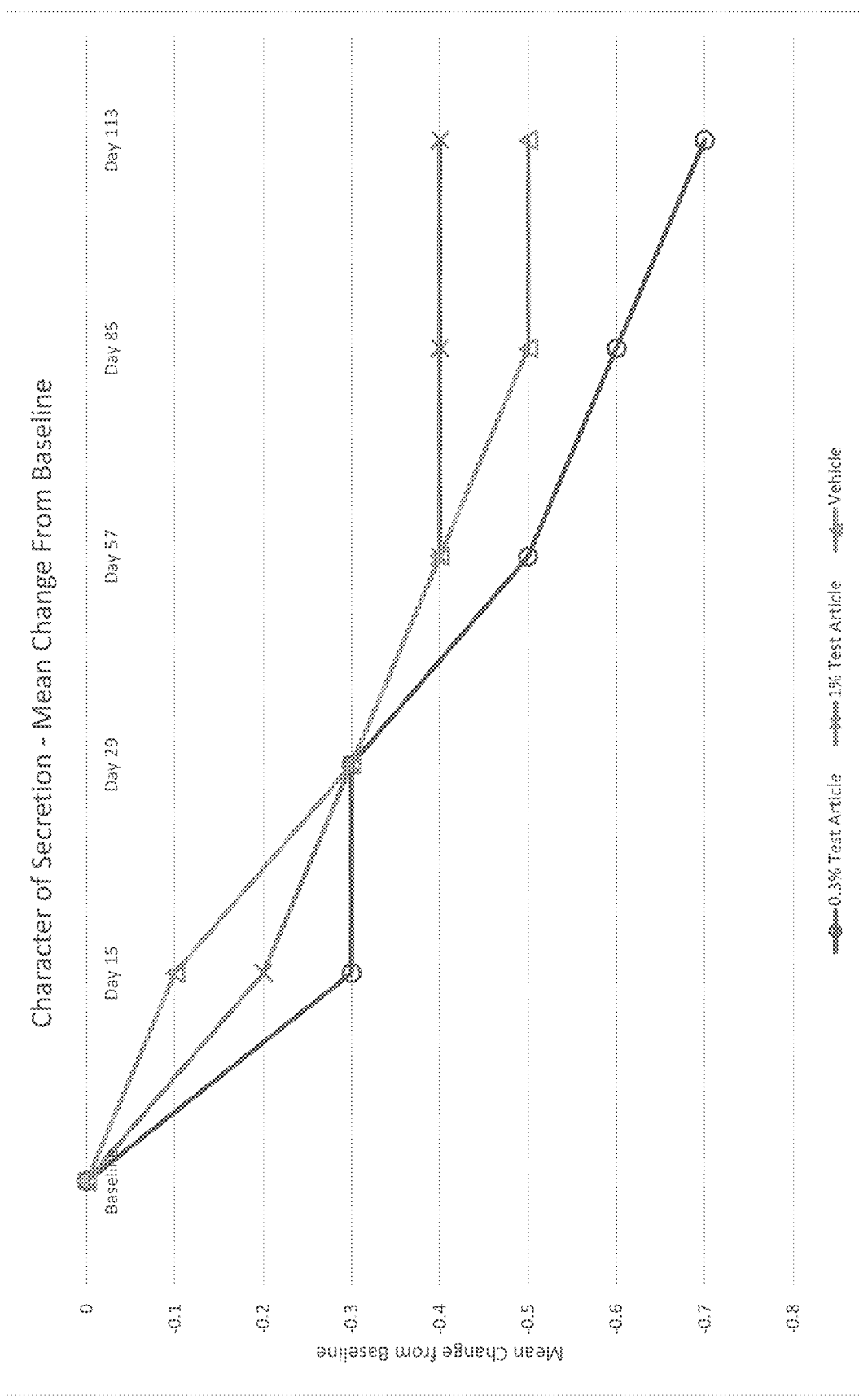
FIG. 12 is a line graph depicting character of secretion (mean change from baseline) results from the clinical study in Example 1.
Figure 13:
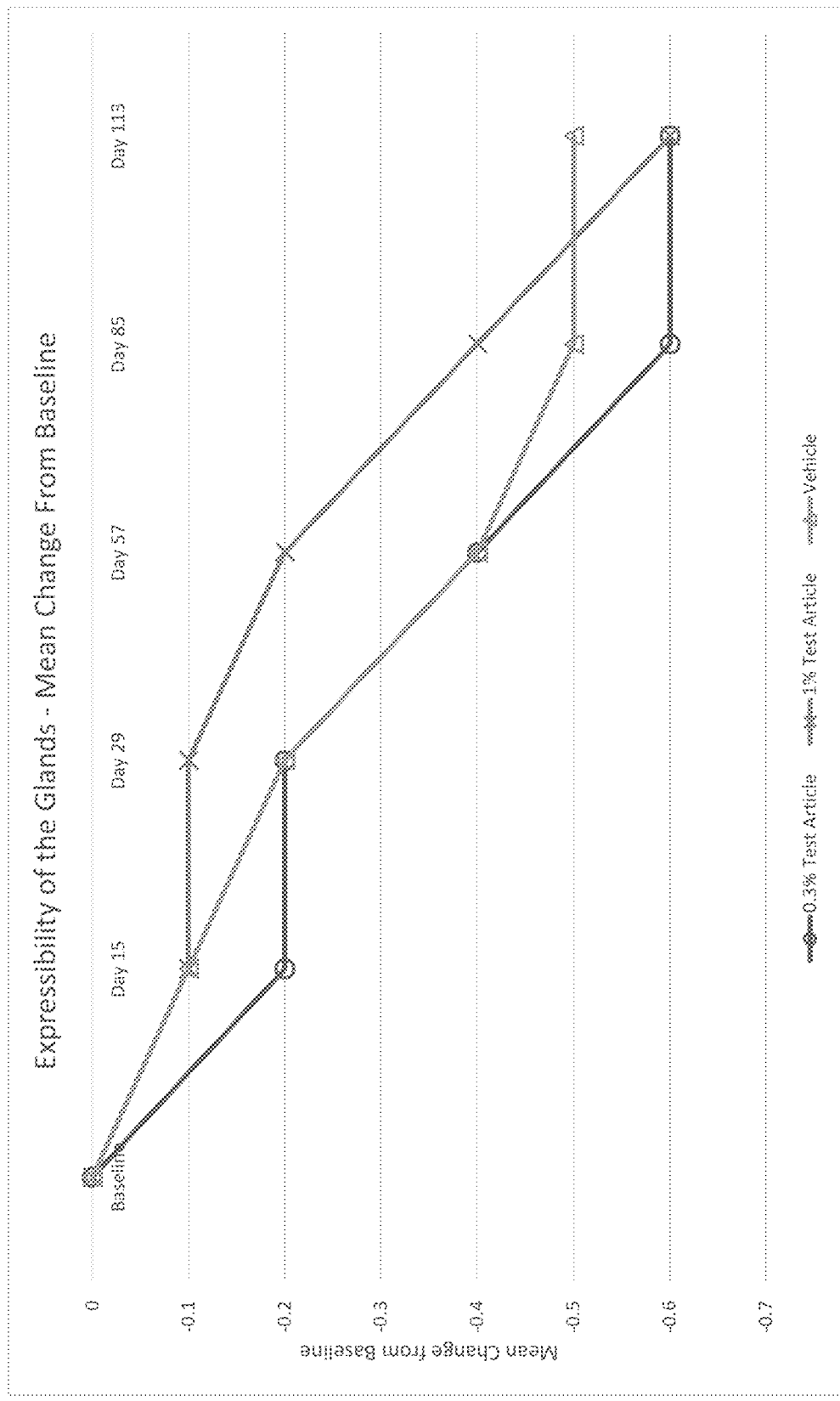
FIG. 13 is a line graph depicting expressibility of the glands (mean change from baseline) results from the clinical study in Example 1.
Figure 14:
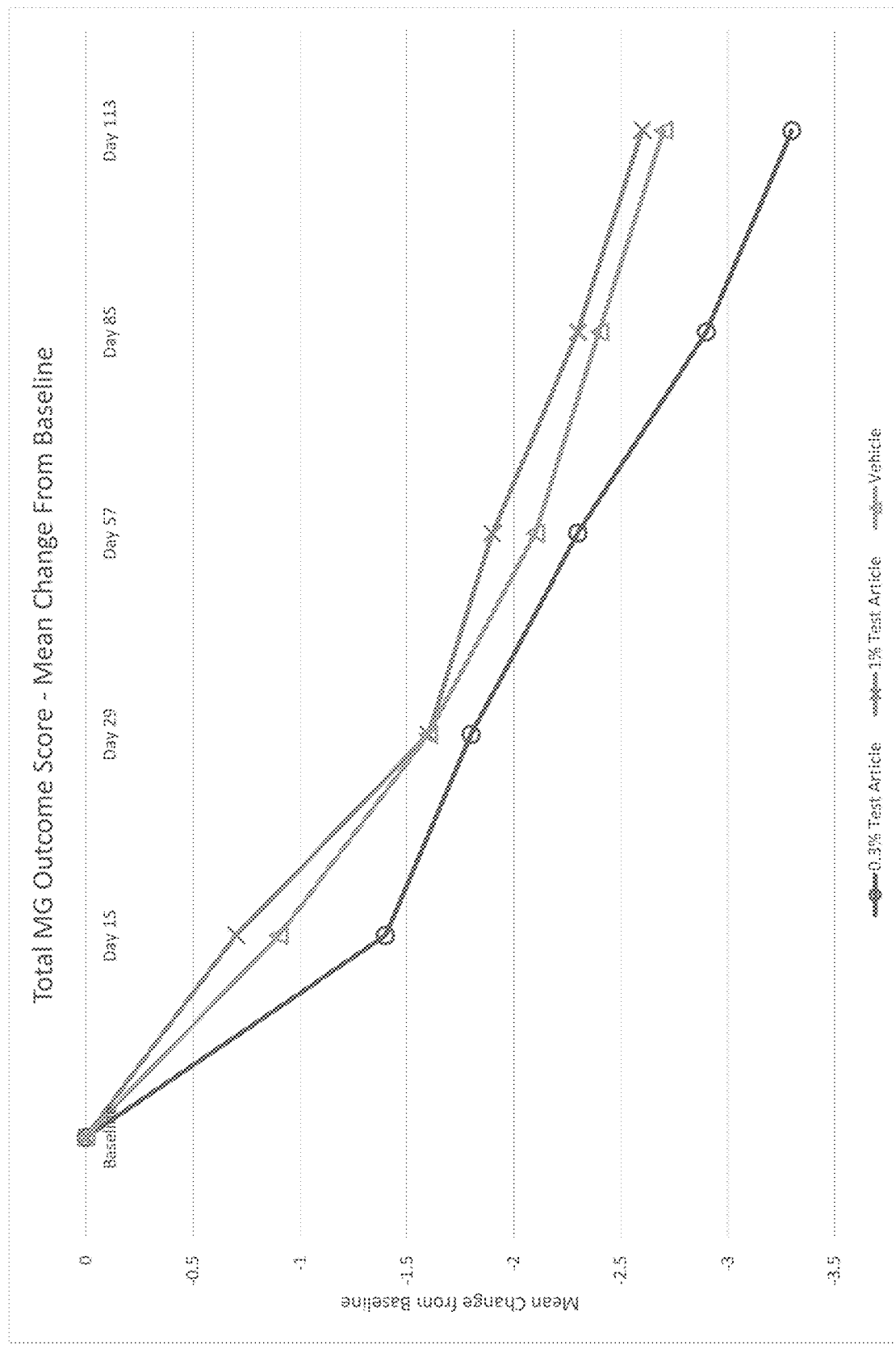
FIG. 14 is a line graph depicting total MG outcome score (mean change from baseline) results from the clinical study in Example 1.
Figure 15:
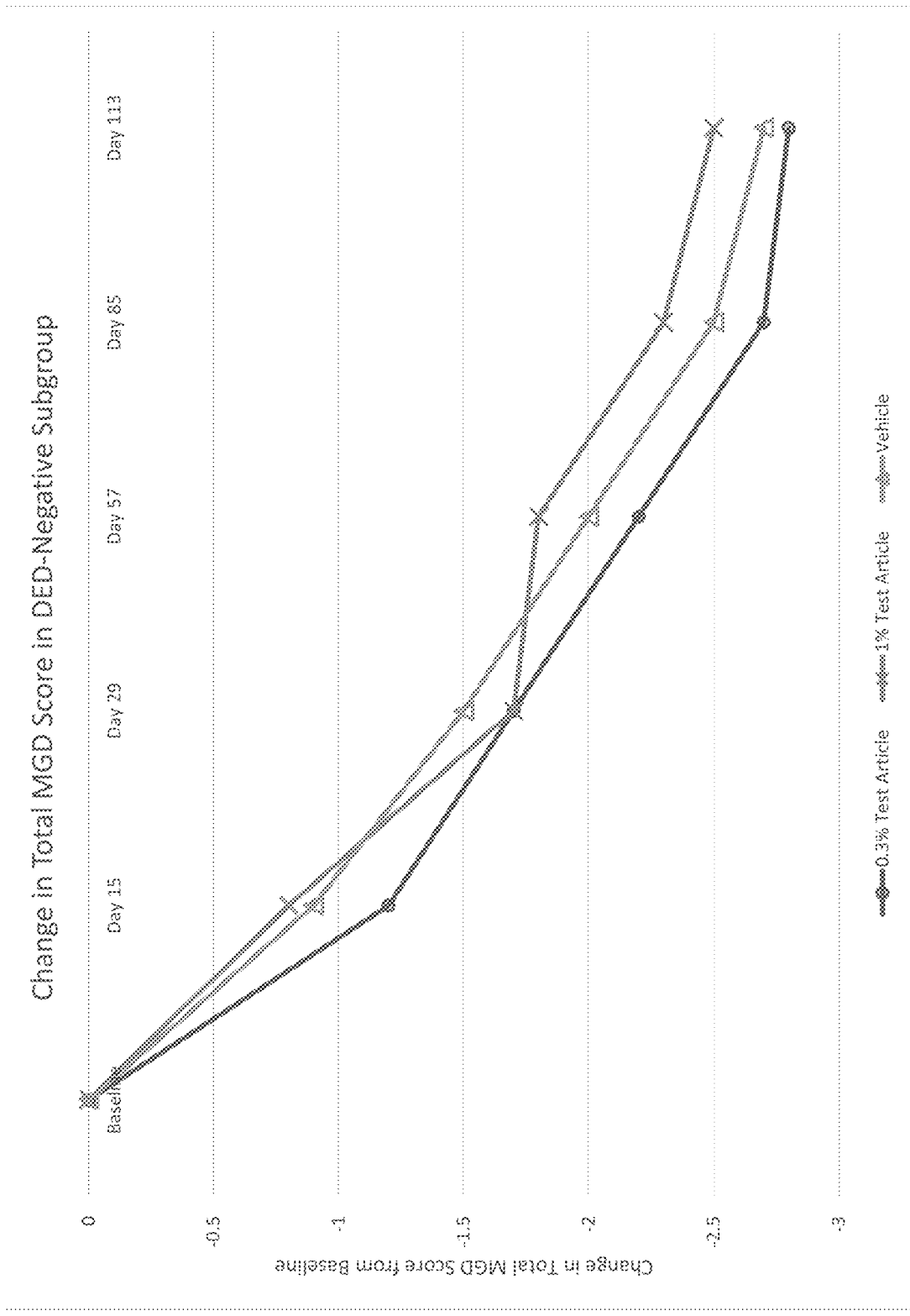
FIG. 15 is a line graph depicting change in total MGD score in Dry Eye Disease (DED)-negative subgroup results from the clinical study in Example 1.
Figure 16:
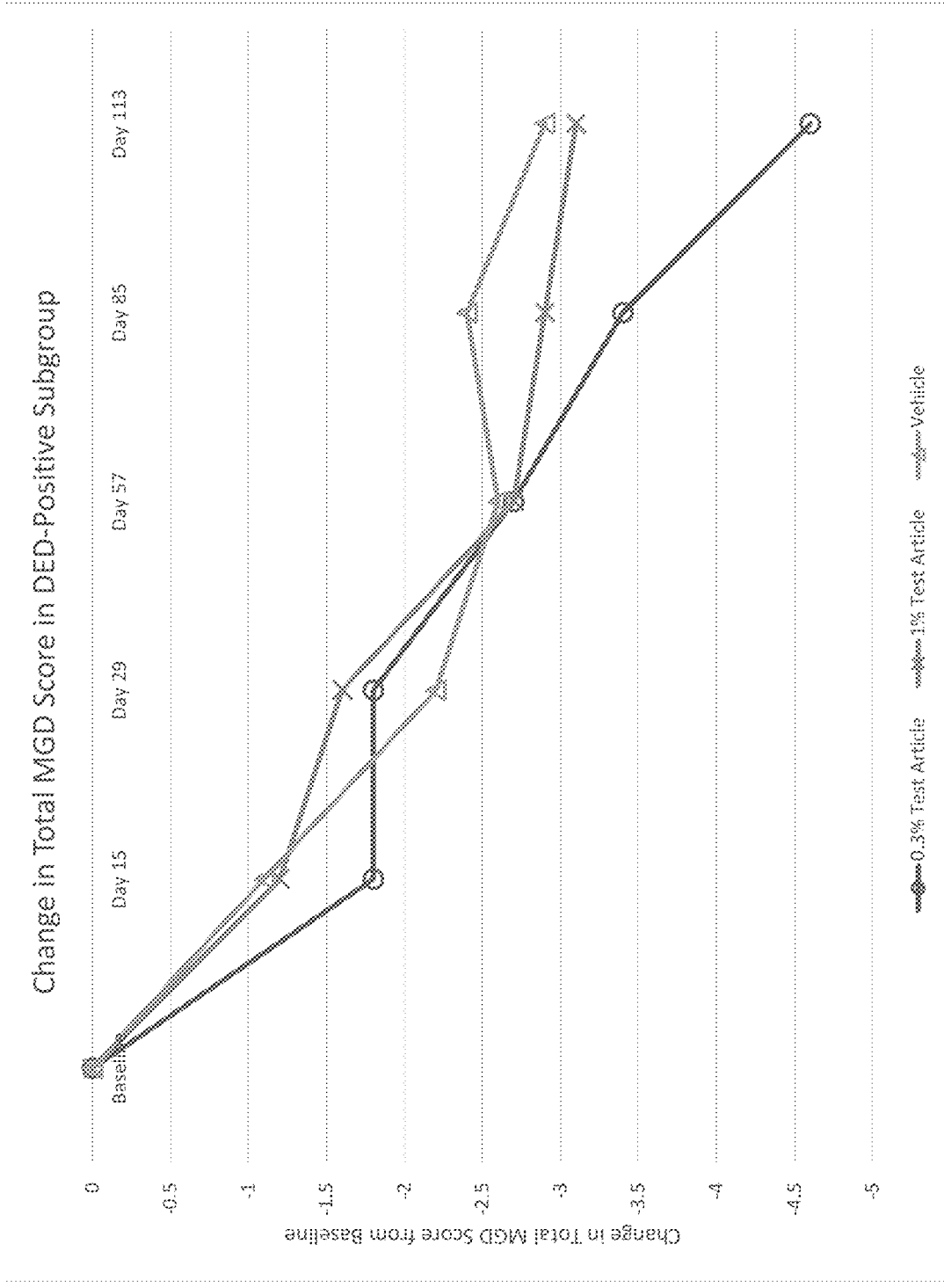
FIG. 16 is a line graph depicting change in total MGD score in DED-positive subgroup results from the clinical study in Example 1.
Figure 17:
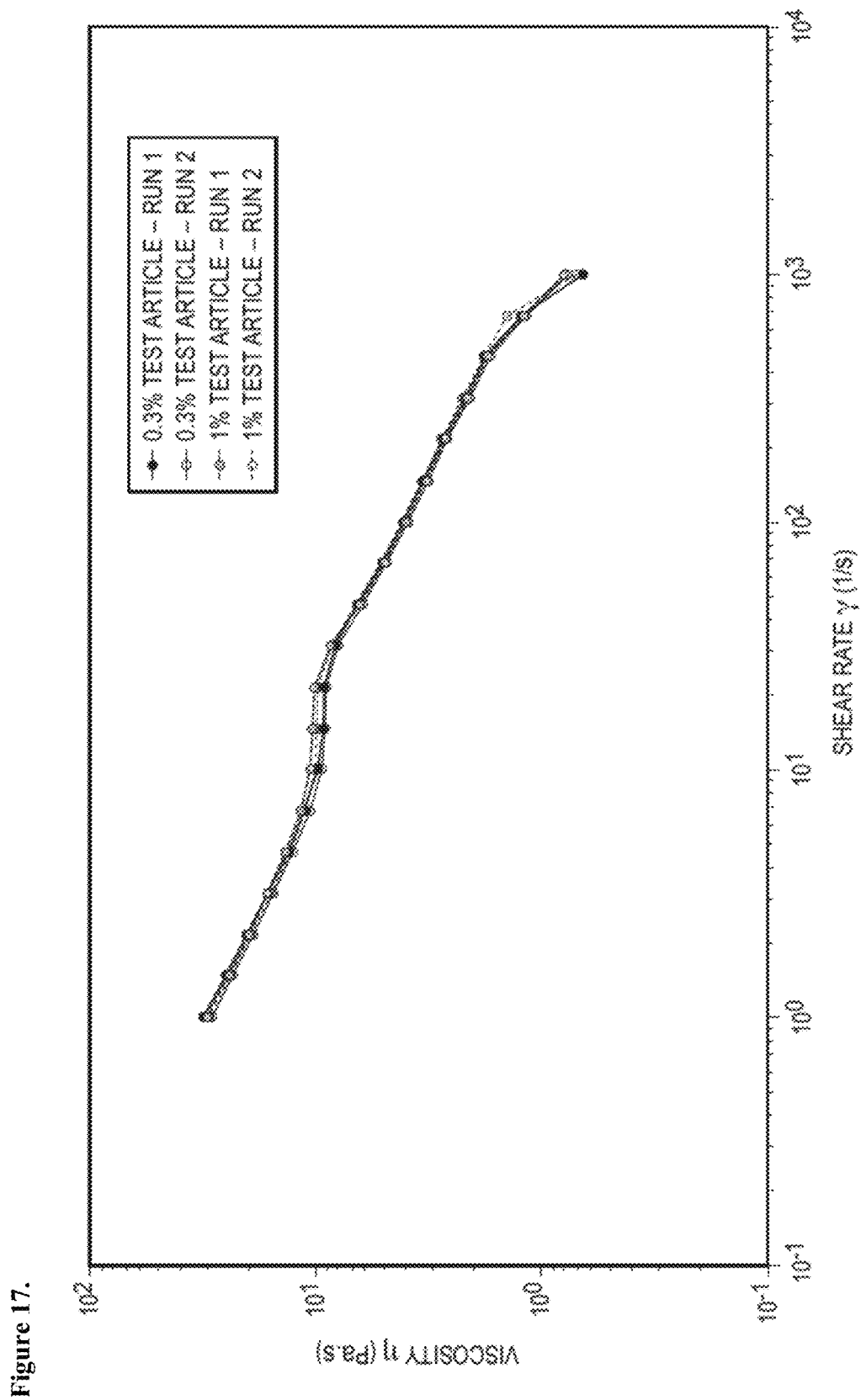
FIG. 17 is a line graph depicting results of the shear rate sweep experiment conducted on 0.3% Test Article and 1% Test Article, as further described in Example 7.
Figure 18:
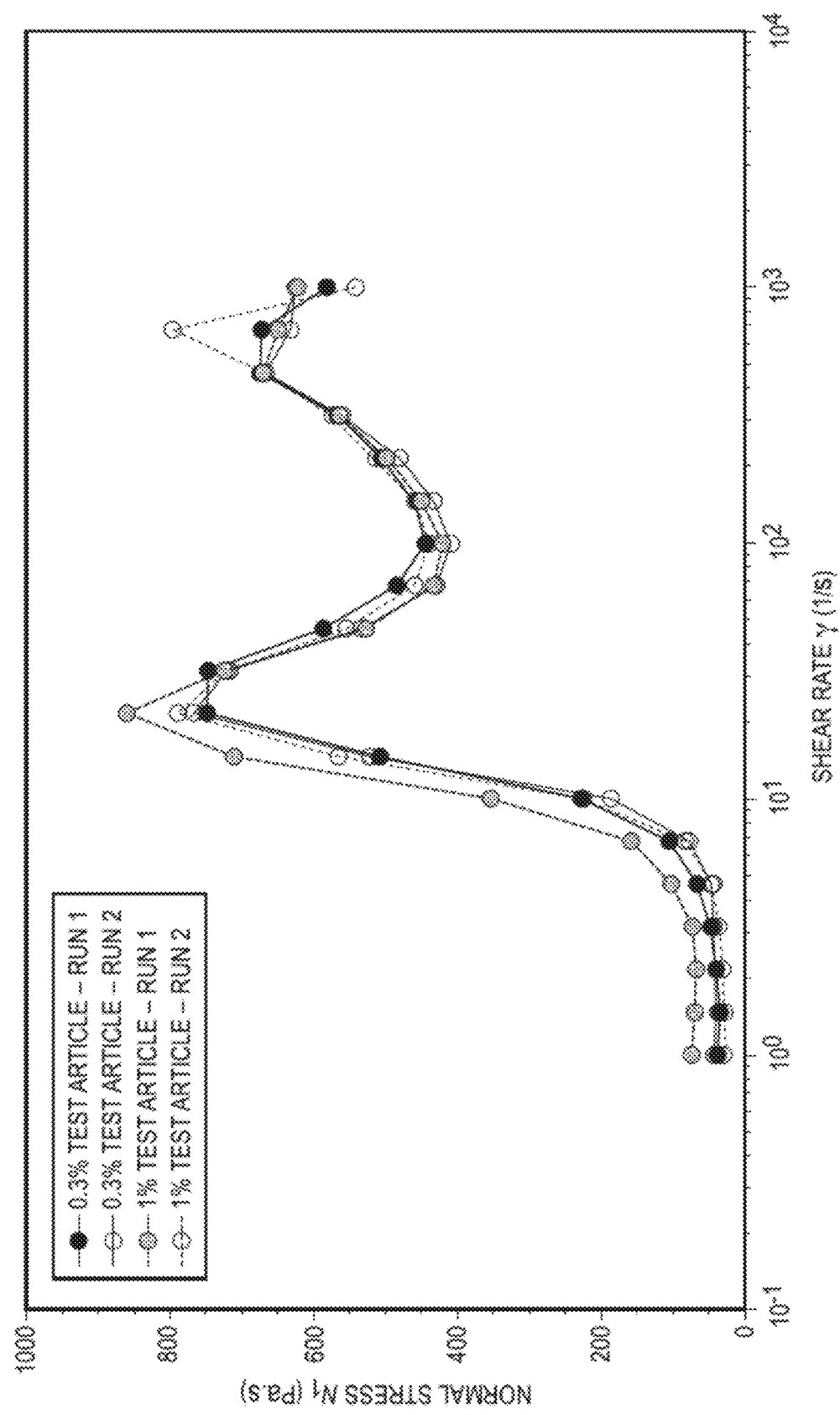
FIG. 18 is a line graph depicting results of the shear rate sweep experiment conducted on 0.3% Test Article and 1% Test Article, as further described in Example 7.
Figure 19:
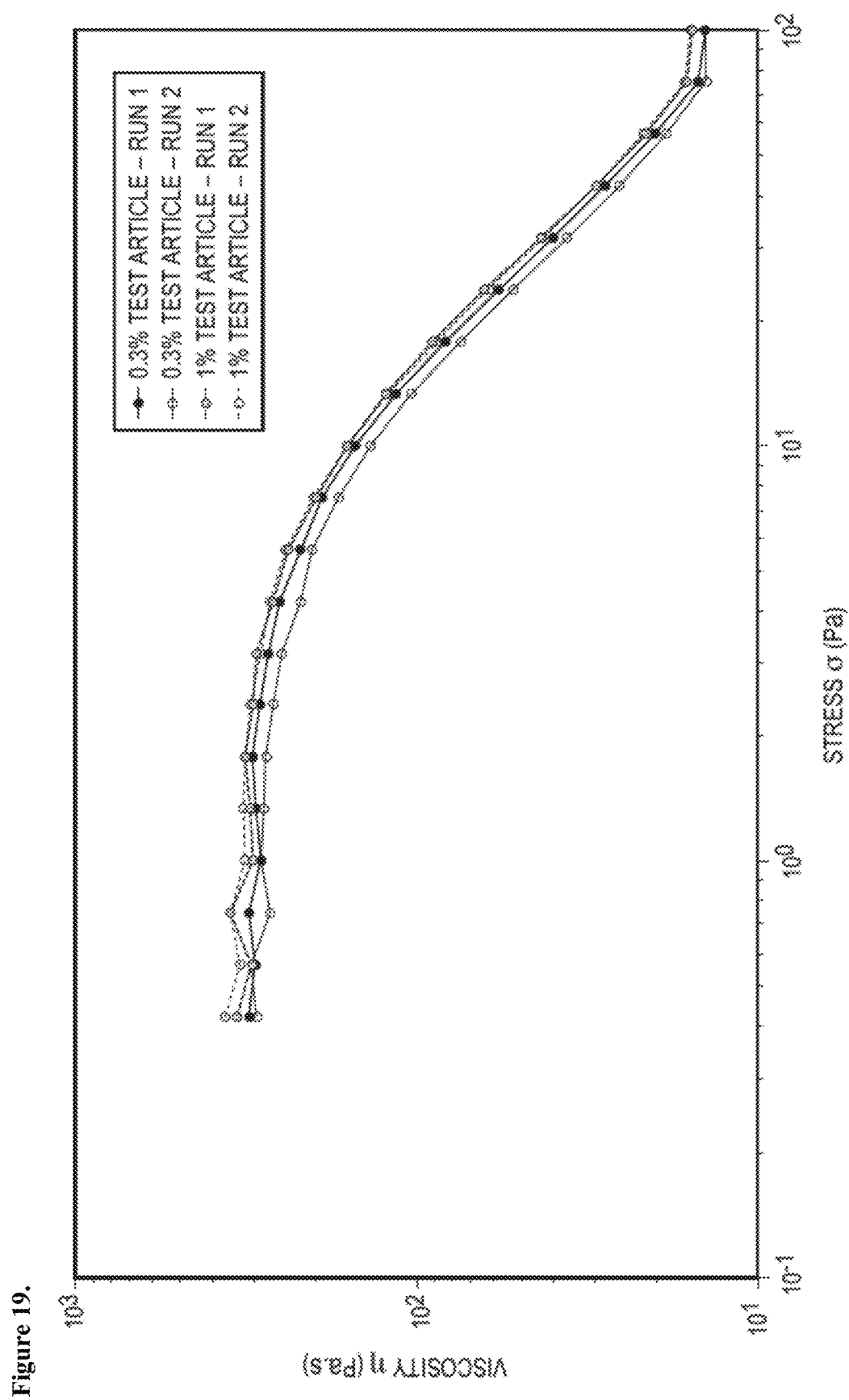
FIG. 19 is a line graph depicting results of the shear stress sweep experiment conducted on 0.3% Test Article and 1% Test Article, as further described in Example 7.
Figure 20:
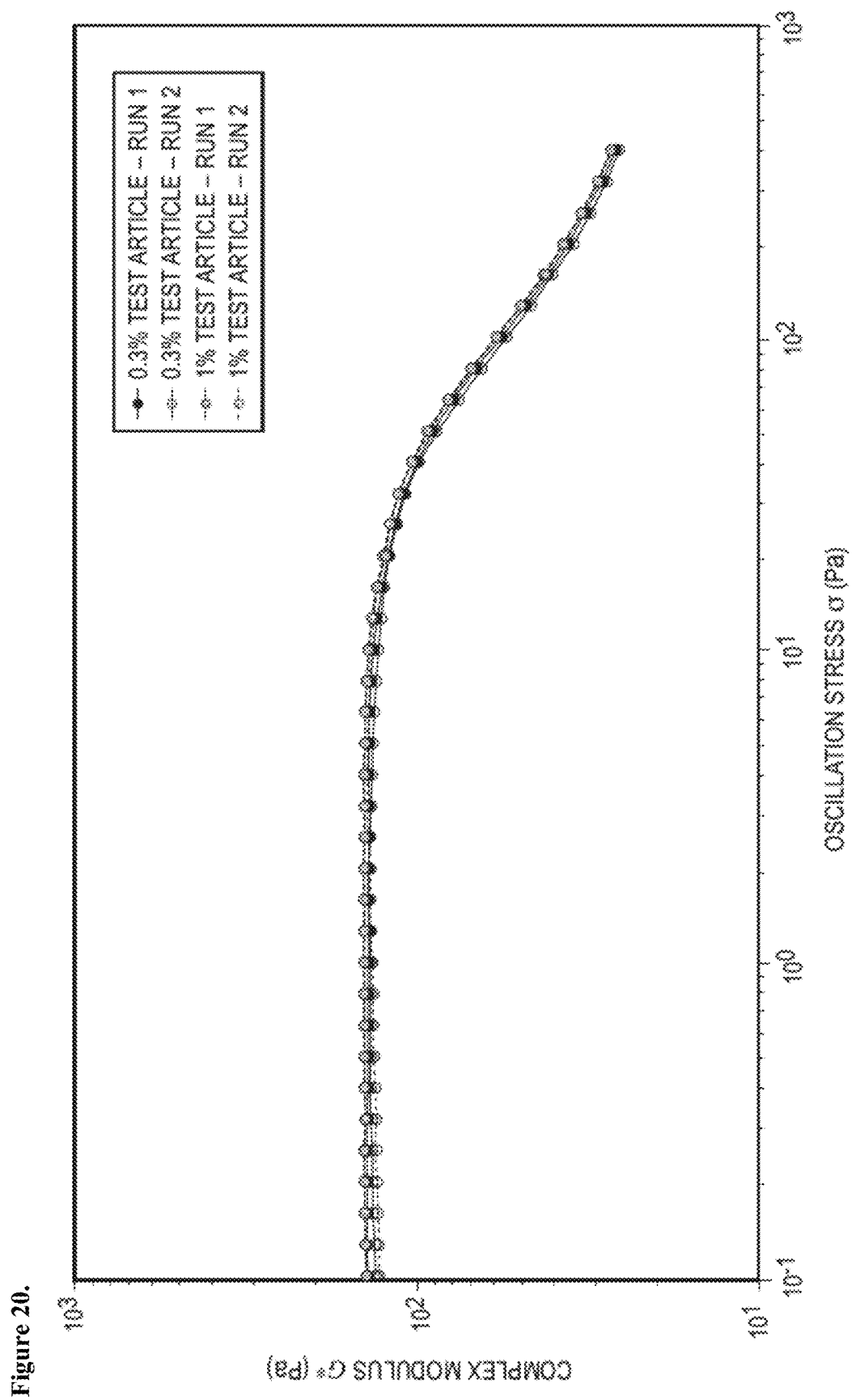
FIG. 20 is a line graph depicting results of the oscillation stress sweep experiment conducted on 0.3% Test Article and 1% Test Article, as further described in Example 7.
Figure 21:
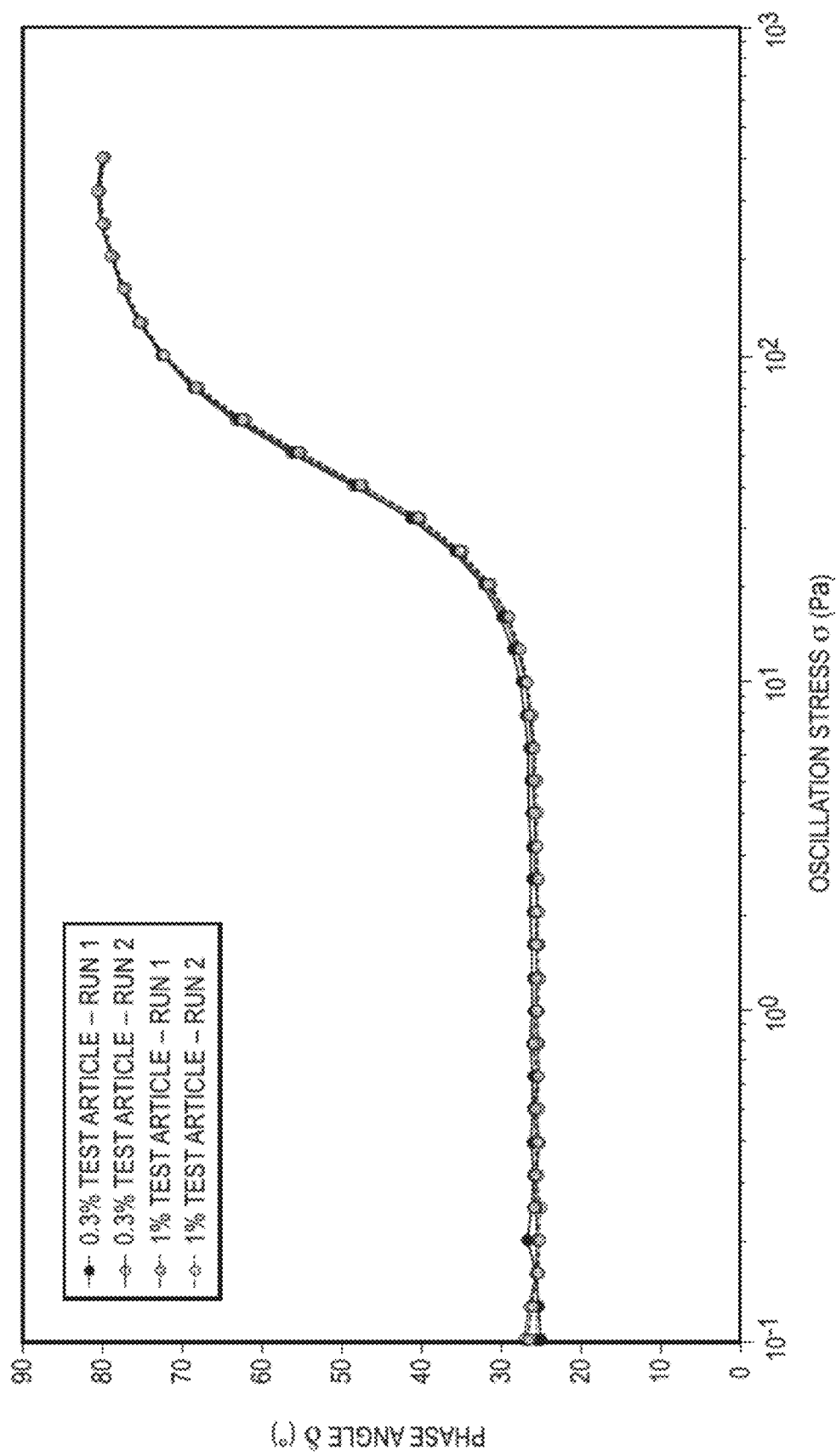
FIG. 21 is a line graph depicting results of the oscillation stress sweep experiment conducted on 0.3% Test Article and 1% Test Article, as further described in Example 7.

5. Fluorescein Corneal Staining (FCS)/National Eye Institute/Industry Workshop Scale FCS is assessed at each visit. The five areas of the cornea are scored by the investigator according to the scoring system shown in FIG. 7, and the total score is also calculated.

6. Unanesthetized Schirmer Test

The Schirmer test is conducted on unanesthetized eyes at Visits 1, 2, 6, and 7. A 35 mm×5 mm filter paper strip is used to measure the amount of tears that are produced over 5 minutes. The strip is placed in the lower eyelid margin without the use of a preplaced ophthalmic anesthetic drop. After 5 minutes, the strip is removed and the amount of wetting is measured in millimeters.

7. MMP-9 Point of Care Assessment

The MMP-9 point of care assessment is conducted at Visit 1 and Visit 6. The Quidel InflammaDry test system is used to assess the tear film for the presence of MMP-9. The sample is obtained, and the test performed according to package instructions. Gently dab the sampling fleece in multiple locations along the palpebral conjunctiva until the fleece glistens, and then place the fleece in the test cassette for analysis. Do not use a dragging motion when collecting the sample and ensure that the fleece is sufficiently moistened prior to testing.

8. Tear Film Break-up Time (TFBUT)

TFBUT is measured at each visit. To measure TFBUT, fluorescein is instilled into the subject's tear film, the subject is allowed to blink once or twice to disperse the fluorescein, and the subject is then asked not to blink while the tear film is observed under a broad beam of cobalt blue illumination using a slit-lamp. The TFBUT is recorded as the number of seconds that elapse between the last blink and the appearance of the first dry spot in the tear film. A TFBUT under 10 seconds is considered abnormal.

9. Investigator-Rated Assessment of Objective Signs Including Change from Baseline for Five Individual Severity Scores The investigator rates the bilateral severity of the subject's MGD signs at each visit according to the following classification:
1. Vascular engorgement at the eyelid margin (evaluate the entire lid margin and evaluate both upper and low eyelid margins separately)
   (0) Normal
   (1) Mild engorgement
   (2) Moderate engorgement
   (3) Severe engorgement
   (4) Very Severe engorgement
2. Plugging of the meibomian gland (evaluate middle part of upper and lower lid, n=10)
   (0) Normal: Clear orifices of meibomian glands (n=0)
   (1) Mild: Less than ⅓ of orifices plugged but at least one appears to contain turbid or oily secretions (n=1-3)
   (2) Moderate: Between ⅓ and ⅔ of orifices plugged (n=4-6)
   (3) Severe: More than ⅔ of orifices plugged (n=7-9)
   (4) Very severe: All orifices plugged (n=10)
3. Character of secretion expressed from the meibomian gland (evaluate middle part of lower lid, n=10 and middle part of upper lid, n=10))
   (0) Normal: minimal clear secretion
   (1) Mild: cloudy
   (2) Moderate: granular
   (3) Severe: paste
   (4) Obstructed: no observable expressate
4. Expressibility of Meibomian Glands (upper and lower lid out of 10 glands)
   (0) All glands expressible
   (1) At least 5 glands expressible
   (2) Only 3-4 glands expressible
   (3) Only 1-2 glands expressible
   (4) No glands are expressible
5. Conjunctival Tarsal Erythema (evaluate upper and lower tarsal conjunctiva) (Note: Level of severity is not required for eligibility)
   (0) Normal: normal age appropriate vascularity of the tarsal conjunctiva
   (1) Trace erythema: slightly dilated blood vessels; vessels colored pink
   (2) Mild erythema: dilated vessels, color light red
   (3) Moderate erythema: diffuse dilated vessels, bright red in color
   (4) Severe erythema: diffuse dilated vessels, deep red color 10. Total Clinical Outcome Severity Score Defined as the Sum of the Four Severity Scores for the Clinical Signs of Meibomian Gland Disease, as Determined Above in "9. Investigator-Rated Assessment of Objective Signs Including Change from Baseline for Five Individual Severity Scores":
   1. Vascular Engorgement of eyelid margin
   2. Plugging of the Meibomian Gland
   3. Character of Secretion Expressed from the Meibomian Gland
   4. Expressibility of the Meibomian Gland O. Assessment of Safety
   Safety parameters include:
1. Adverse Event Monitoring
   See Section O. Adverse Event Definitions
2. ETDRS Best Corrected Visual Acuity BCVA is conducted at each visit. Visual acuity testing should precede any examination requiring contact with the eye or instillation of study dyes, as is detailed in the order of assessments for each Visit in Section 5.1. Logarithm of the Minimal Angle of Resolution (Log MAR) visual acuity must be assessed using an ETDRS or modified ETDRS chart. Visual acuity testing is performed with best correction using subject's own corrective lenses (spectacles only) or pinhole refraction.

An ETDRS or modified ETDRS chart may be used. If a Lighthouse chart is used (24.5" by 25"; either reflectance or retro-illuminated), the subject must view the chart from a distance of exactly 4 meters (13.1 feet). If smaller reproductions (18" by 18", e.g., Prevent Blindness) are used, the subject viewing distance is exactly 10 feet. Reflectance wall charts are frontally illuminated (60 watt bulb or a well-lit room).

The subject is positioned according to the elevation of the chart (either seated or standing) so that the chart is at a comfortable viewing angle. The right eye is tested first. The subject should attempt to read each letter, line-by-line, left to right, beginning with line 1 at the top of the chart. The subject is told that the chart has letters only, no numbers. If the subject reads a number, he or she is reminded that the chart contains no numbers, and the examiner should then request a letter instead of the number. The subject is asked to read slowly, about 1 letter per second, to achieve the best identification of each letter. He/she is not to proceed to the next letter until he/she has given a definite response. If the subject changes a response before he has read aloud the next letter, then the change must be accepted.

Maximum effort is made to identify each letter on the chart; the subject is encouraged to guess. When it becomes evident that no further meaningful readings can be made, the examiner should stop the test. The number of letters missed or read incorrectly is noted.

In order to provide standardized and well-controlled assessments of visual acuity during the study, the same lighting conditions must be used consistently throughout the study.

Calculations: $\log \text{MAR } VA = \text{Baseline value} + (n \times 0.02)$ where: the baseline value is the log MAR number of the last line read (at least 1 letter read correctly in this line), and "n" is the total number of letters missed up to and including the last line read, and "0.02" is the value for each letter 3. Slit Lamp Biomicroscopy and External Eye Exam The biomicroscopy exam is performed at each visit. It is performed with the slit lamp using a beam width and intensity that provide optimal evaluation of the anterior segment. This procedure is performed in the same manner for all subjects observed at the Investigator's site.

Lashes
   0=Normal
   1=Abnormal

Eyelid
    Edema
        0=Normal, no swelling of the lid tissue
        1=Abnormal
Conjunctiva
    Edema
        0=Normal, no swelling of the conjunctiva
        1=Abnormal
Palpebral Conjunctival Erythema
        0=Normal, no redness of the conjunctiva
        1=Abnormal
Cornea
    Infiltrates
        0=Absent
        1=Present
    Endothelial Changes
        0=Normal, None
        1=Abnormal, pigment, keratoprecipitates, guttata
    Edema
        0=Normal None, transparent and clear
        1=Abnormal
Anterior Chamber
    Cells
        0=Normal, No cells seen
        1=Abnormal (+ to +++ cells)
    Flare
        0=Normal, No Tyndall effect
        1=Abnormal, Tyndall beam in the anterior chamber
Lens Pathology
        0=Normal; no opacity in the lens
        1=Abnormal; existing opacity in the lens; aphakic or pseudophakic eyes or other abnormal findings.
Sclera
    Injection
        0=Normal, without any redness
        1=Abnormal 4. IOP Measurement TOP measurements are performed utilizing Goldmann applanation tonometry according to the Investigator's standard procedure. All pressures are recorded in mmHg.

5. Dilated Ophthalmoscopy

Dilated ophthalmoscopy includes assessment of the optic nerve head for pallor and cupping (cup to disc ratio), and is performed at Visit 1 and Visit 6. After the ophthalmoscopy procedure, the Investigator determines if findings are within normal limits or are abnormal. For abnormal findings at Visit 1, the Investigator determines whether or not the abnormality would exclude subject from study participation.

P. Adverse Event Definitions

Adverse Event (AE): Any untoward medical occurrence associated with the use of an investigational product in humans, whether or not considered drug related.

Adverse Reaction (AR): any AE caused by a drug. Adverse reactions are a subset of all suspected adverse reactions where there is reason to conclude that the drug caused the event.

Suspected Adverse Reaction (SAR): Any AE for which there is a reasonable possibility that the drug caused the AE. For the purposes of IND safety reporting, "reasonable possibility" means there is evidence to suggest a causal relationship between the drug and the AE. A SAR implies a lesser degree of certainty about causality than adverse reaction, which means any AE caused by a drug.

Unexpected: An AE or SAR is considered "unexpected" if it is not listed in the Investigator's Brochure or is not listed at the specificity or severity that has been observed; or, if an Investigator's Brochure is not required or available, is not consistent with the risk information described in the general investigational plan or elsewhere in the current application.

Life-threatening: An AE or SAR is considered "life-threatening" if, in the view of either the Investigator or Sponsor, its occurrence places the patient or subject at immediate risk of death. It does not include an AE or suspected adverse reaction that, had it occurred in a more severe form, might have caused death.

Serious Adverse Event (SAE): any AE or suspected adverse reaction occurring at any dose that:
    Results in death.
    Is life-threatening.
    Results in a persistent or significant incapacity or substantial disruption of the ability to conduct normal life functions.
    Requires inpatient hospitalization.
    Prolongs inpatient hospitalization.
    Is a congenital anomaly/birth defect.
    Is a significant medical event (i.e., one that may jeopardize the subject or may require intervention to prevent one or more of the other outcomes listed above).

Non-Serious Adverse Event: any AE that does not meet the definitions for SAEs as described above.

Each AE is classified as SERIOUS or NON-SERIOUS using the definitions provided above.

The SEVERITY of each AE is classified as MILD, MODERATE, or SEVERE.

The Investigator reviews each event and assess its relationship to use of investigational product (unrelated, unlikely, possibly, probably, definitely). The AE is assessed using the following definitions:
    Unrelated:
    Event occurring before dosing.
    Event or intercurrent illness due wholly to factors other than investigational product use.
    Unlikely:
    Poor temporal relationship with investigational product use.
    Event easily explained by subject's clinical state or other factors.
    Possible:
    Reasonable temporal relationship with investigational product use.
    Event could be explained by subject's clinical state or other factors.
    Probable:
    Reasonable temporal relationship with investigational product use.
    Likely to be known reaction to agent or chemical group, or predicted by known pharmacology.
    Event cannot easily be explained by subject's clinical state or other factors.
    Definite:
    Distinct temporal relationship with investigational product use.
    Known reaction to agent or chemical group, or predicted by known pharmacology.
    Event cannot be explained by subject's clinical state or other factors.

Q. Procedures for AE Reporting by the Investigator

AEs are monitored throughout the study and are recorded on the eCRF with the date and time of onset, date and time of resolution, severity, seriousness, causality (relationship to use of investigational product), treatment required, and the outcome. To elicit AEs, simple questions with minimal suggestions or implications are used as the initial questions at all evaluation points during the trial. For example:

How have you felt since your last assessment?

Have you had any health problems since your last assessment?

The severity of each AE is categorized as mild, moderate, or severe. The causality of use of investigational product in relation to the AE is assessed by the Principal Investigator after careful medical consideration and categorized as unrelated, unlikely, possible, probable, or definite. If an AE occurs, the Investigator institutes support and/or treat as deemed appropriate. If a non-SAE is unresolved at the time of the last day of the study, an effort is made to follow up until the AE is resolved or stabilized, the subject is lost to follow-up, or there is some other resolution of the event. The Investigator should make every attempt to follow SAES to resolution.

It is the responsibility of the Investigators or their designees to report any event of this nature to the Sponsor or a designee within 24 hours of the event being brought to the Investigators' or their staffs' attention. It is also the responsibility of the Investigator to report all SAES reported at their site to their Institutional Review Board (IRB), as required. The Investigator should make every attempt to follow all SAES to resolution.

The following information is provided when an SAE is reported to the Sponsor or designee:

1. Protocol Number
1. Site Number
2. Subject Number
3. Subject Demographic information, including:
Date of Birth
Sex
Race
4. Investigational product start date
5. Date of last dose of investigational product
6. Date investigational product reinitiated (if investigational product interrupted)
7. SAE information, including:
SAE term (diagnosis only; if known or serious signs/symptoms)
Description of SAE/narrative
Date/time of onset
Severity
Outcome
Date/time of resolution or death (if duration <24 hours)
Relationship to investigational product
Action taken with investigational product
8. Criteria for classifying the event as serious, including whether the SAE:
Resulted in death.
Was life-threatening
Required inpatient hospitalization.
Prolonged inpatient hospitalization.
Resulted in a persistent or significant incapacity or substantial disruption of the ability to conduct normal life functions.
Was a congenital anomaly/birth defect
Important medical events that may not result in death, were not life-threatening, or did not require hospitalization may be considered serious when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.
9. Concomitant medications
10. Relevant history
11. Possible causes of SAE other than investigational product
12. Copy of AE page from the CRF If an SAE occurs in any study involving Test Article or Vehicle that is unexpected and is determined to be related or possibly related to investigational product, all sites are notified by the Sponsor and each site should report it to its IRB.

R. Statistical Methods

Continuous measures (e.g., age) are summarized descriptively by the mean, standard deviation, median, minimum and maximum values. Categorical measures are summarized by the number and percent of subjects. The statistical analyses are performed in accordance with the Statistical Analysis Plan. All study data is listed by treatment, patient and visit (as applicable). Subject disposition, demographic characteristics, and background variables are summarized by treatment group.

1. Analysis of Efficacy
Analysis Populations:
Intent-to-Treat (ITT) Population: The ITT population includes all randomized subjects who took at least 1 dose of study drug. This population is the primary population for efficacy analyses and is used to summarize all efficacy variables by treatment group as randomized.
Per Protocol (PP) Population: The PP population is a subset of the ITT population, which includes those subjects who do not have important protocol deviations likely to seriously affect the primary efficacy outcomes of the study. This population is the secondary population for efficacy analyses by treatment group as treated. The Per Protocol Population is defined and documented by the clinical study team and the biostatistician prior to database lock and unmasking of the subjects.
Evaporative Dry Eye Disease (DED) Population: The Evaporative DED population is a subset of PP population, which includes those subjects with associated evaporative DED as determined at baseline. Further a positive Screening for MMP-9 is evaluated as a subset of the PP population.

To assess whether Test Article is more effective than Vehicle, a repeated measures mixed model analysis of covariance (ANCOVA) is used where change from baseline is the outcome, treatment group is a fixed effect with baseline score as a covariate and visit as a repeated measure. The presence/absence of DED and its interaction with treatment may be included in the model as appropriate. Least squares means are used to test each concentration of Test Article compared to Vehicle. Statistical testing is carried out at the 0.05 significance level. A hierarchical testing scheme is implemented for the Primary Endpoints in the following sequential order:

1. Changes in Vascular Engorgement at the study eyelid margin as graded by the investigator at Week 12 (Visit 6) from Randomization/Baseline (Visit 2) in 1% Test Article compared to Vehicle
2. Change in Eye Discomfort Visual Analogue Score (VAS) at Week 12 (Visit 6) from Randomization/Baseline (Visit 2) in 1% Test Article compared to Vehicle 3. Changes in Vascular Engorgement at the study eyelid margin as graded by the investigator at Week 12 (Visit 6) from Randomization/Baseline (Visit 2) in 0.3% Test Article compared to Vehicle
4. Change in Eye Discomfort Visual Analogue Score (VAS) at Week 12 (Visit 6) from Randomization/Baseline (Visit 2) in 0.3% Test Article compared to Vehicle Each comparison is made in the above pre-specified order to determine if the difference is statistically significant (p-value≤0.05). If the difference is statistically significant, then the same test is repeated for the next comparison. If, at any time, the p-value is >0.05 then testing is stopped. Secondary endpoints are tabulated by descriptive statistics:

Change in FCS total score (NEI/Industry Workshop 0-15 scale) in the study eye at Week 4 (Visit 4), Week 8 (Visit 5), Week 12 (Visit 6), and Week 16 (Visit 7) from Randomization/Baseline (Visit 2).

Change in FCS inferior, nasal, and central combined score (NEI/Industry Workshop Section 1, 4 and 5 with a 0-9 scale) in the study eye at Week 4 (Visit 4), Week 8 (Visit 5), Week 12 (Visit 6) and Week 16 (Visit 7) from Randomization/Baseline (Visit 2).

Change in FCS inferior score (NEI/Industry Workshop sections 5 with a 0-3 scale) in the study eye at Week 4 (Visit 4), Week 8 (Visit 5), Week 12 (Visit 6), and Week 16 (Visit 7) from Randomization/Baseline (Visit 2).

Changes in Eye Discomfort Visual Analogue Score (VAS) at Changes in Eye Discomfort Visual Analogue Score (VAS) at Week 4 (Visit 4), Week 8 (Visit 5), Week 12 (Visit 6), and Week 16 (Visit 7) from Randomization/Baseline (Visit 2).

Investigator reported scores on objective signs of inflamed MGD including change from baseline at each follow up visit for four individual severity scores:
1. Plugging of Meibomian Gland
2. Character of Meibomian Gland Secretion
3. Vascular Engorgement of eyelid margin
4. Expressibility of Meibomian Glands Total Clinical Outcome Severity Score defined as the sum of the following four severity scores for the clinical signs of:
1. Plugging of Meibomian Gland
2. Character of Meibomian Gland Secretion
3. Vascular Engorgement of eyelid margin
4. Expressibility of Meibomian Glands Changes in Investigator reported scores on objective Conjunctival Tarsal Erythema change from Randomization/Baseline (Visit 2) at each follow up visit.

Tear Film Break-Up Time (TFBUT) change from baseline at each follow up visit.

Other Dry Eye-related ocular symptoms at each follow-up visit:
VAS Scale Symptoms (other than eye discomfort):
Eye Dryness
Foreign Body Sensation
SANDE change in the square root of the product of the two questions at each timepoint compared to baseline and the change from baseline of each individual question within the SANDE The mean tear osmolarity score at each follow up visit compared to baseline. (Analysis is conducted at a subset of sites.)

The change from baseline in the unanesthetized Schirmer score.

The portion of subjects who are positive at Screening for MMP-9 point of care test and convert to negative at the final treatment visit.

Number of symptom flares during the twelve weeks of treatment.

2. Analysis of Safety

Analysis of safety data is presented for all subjects in the Safety population (i.e., all subjects receiving randomized investigational product). AEs are coded using Medical Dictionary for Regulatory Activities (MedDRA, most current version) and categorized by system organ class using preferred terms. AEs are tabulated by treatment group with respect to their Severity and relationship to the investigational product. Ophthalmoscopy findings are summarized descriptively. TOP measurements, BCVA, dilated ophthalmoscopy, external eye exam, and slit-lamp biomicroscopy are summarized as safety outcomes.

3. Sample Size Estimation

Based on other similar clinical studies, assuming the treatment effect size is at least 0.43, a sample of 85 subjects per group provides a power of 80% on a two-sided t-test at an alpha level of 0.05.

4. Level of Significance

The primary assessment of the dose-response is evaluated using a 5% level of significance. All other reported p-values are considered descriptive and hypothesis generating.

Part II—Results

The clinical study included randomized 270 subjects, of which 91 subjects received 0.3% Test Article, 89 subjects received 1% Test Article, and 90 subjects received only Vehicle according to the dosing protocol described above. Results of the clinical study are provided in Tables 4-29 and FIGS. 8-16. Experimental results in Table 4 demonstrate that the 0.3% Test Article has superior tolerability compared to the 1% Test Article or Vehicle alone—only 8.8% of subjects that received 0.3% Test Article left the study early, whereas 12.4% of subjects that received 1% Test Article left the study early and 12.2% of subjects that received only Vehicle left the study early.

Additionally, experimental results in Tables 5, 6, 11, and 12 demonstrate that the 0.3% Test Article produced superior results in the primary efficacy endpoints of VAS Discomfort Mean Change from Baseline and Vascular Engorgement Mean Change from Baseline compared to 1% Test Article or Vehicle alone. At day 113 of the study, VAS Discomfort mean Change from Baseline was −32.4 for subjects that received 0.3% Test Article, whereas VAS Discomfort Mean Change from Baseline was −26.2 for subjects that received 1% Test Article and VAS Discomfort mean Change from Baseline was −27.1 for subjects that received Vehicle alone. At day 113 of the study, Vascular Engorgement Mean Change from Baseline was −1 for subjects that received 0.3% Test Article, whereas Vascular Engorgement Mean Change from Baseline was −0.8 for subjects that received 1% Test Article or Vehicle alone.

TABLE 4

| | 0.3% Test Article | | 1% Test Article | | Vehicle | | Total | |
| --- | --- | --- | --- | --- | --- | --- | --- | --- |
| Subjects | n | % | n | % | n | % | n | % |
| Subjects Who Completed the Study | 83 | 91.2 | 78 | 87.6 | 79 | 87.8 | 240 | 88.9 |

TABLE 4-continued

| Subjects | 0.3% Test Article | | 1% Test Article | | Vehicle | | Total | |
|---|---|---|---|---|---|---|---|---|
| | n | % | n | % | n | % | n | % |
| Subjects Who Discontinued the Study | 8 | 8.8 | 11 | 12.4 | 11 | 12.2 | 30 | 11.1 |
| Adverse Event | 3 | 3.3 | 7 | 7.9 | 5 | 5.6 | 15 | 5.6 |
| Withdrawn by Subject | 5 | 5.5 | 3 | 3.4 | 3 | 3.3 | 11 | 4.1 |
| Lost to Follow-Up | 0 | 0 | 1 | 1.1 | 2 | 2.2 | 3 | 1.1 |
| Other | 0 | 0 | 0 | 0 | 1 | 1.1 | 1 | 0.4 |

TABLE 5

VAS Discomfort

Mean VAS Score

| Timepoint | 0.3% Test Article | 1% Test Article | Vehicle |
|---|---|---|---|
| Baseline | 67.8 | 66.7 | 65.9 |
| Day 15 | 49.3 | 52 | 53.5 |
| Day 29 | 45.6 | 49.4 | 44.4 |
| Day 57 | 42.8 | 45.4 | 41.4 |
| Day 85 | 38 | 41 | 35.8 |
| Day 113 | 36.1 | 40.1 | 37.7 |

TABLE 6

VAS Discomfort

Mean Change From Baseline

| Timepoint | 0.3% Test Article | 1% Test Article | Vehicle |
|---|---|---|---|
| Baseline | 0 | 0 | 0 |
| Day 15 | −18.1 | −15.2 | −14 |
| Day 29 | −22.2 | −17.7 | −20.8 |
| Day 57 | −25 | −21.5 | −24 |
| Day 85 | −30.1 | −25.4 | −28.7 |
| Day 113 | −32.4 | −26.2 | −27.1 |

TABLE 7

VAS Eye Dryness

Mean VAS Score

| Timepoint | 0.3% Test Article | 1% Test Article | Vehicle |
|---|---|---|---|
| Baseline | 64.4 | 62.8 | 60.1 |
| Day 15 | 51.3 | 50.6 | 49.7 |
| Day 29 | 46.3 | 47.7 | 44 |
| Day 57 | 44.5 | 45.4 | 43.1 |
| Day 85 | 39.6 | 41.2 | 36.5 |
| Day 113 | 39.6 | 42.4 | 40 |

TABLE 8

VAS Eye Dryness

Mean Change From Baseline

| Timepoint | 0.3% Test Article | 1% Test Article | Vehicle |
|---|---|---|---|
| Baseline | 0 | 0 | 0 |
| Day 15 | −12.6 | −12.7 | −9.7 |
| Day 29 | −18.3 | −16.1 | −15.1 |
| Day 57 | −20.2 | −18.1 | −16.2 |
| Day 85 | −25.2 | −22.2 | −22.2 |
| Day 113 | −25.5 | −21 | −18.9 |

TABLE 9

VAS Foreign Body Sensation

Mean VAS Score

| Timepoint | 0.3% Test Article | 1% Test Article | Vehicle |
|---|---|---|---|
| Baseline | 59 | 57 | 59.4 |
| Day 15 | 45.9 | 47.3 | 43.9 |
| Day 29 | 39.5 | 46.7 | 41.3 |
| Day 57 | 40.1 | 41.3 | 37.9 |
| Day 85 | 34.8 | 39.3 | 33.5 |
| Day 113 | 33.3 | 37.4 | 35.8 |

TABLE 10

VAS Foreign Body Sensation

Mean Change From Baseline

| Timepoint | 0.3% Test Article | 1% Test Article | Vehicle |
|---|---|---|---|
| Baseline | 0 | 0 | 0 |
| Day 15 | −12.5 | −10.1 | −14.8 |
| Day 29 | −18.8 | −11.2 | −17.3 |
| Day 57 | −18 | −16 | −20.6 |
| Day 85 | −23.8 | −18.1 | −25 |
| Day 113 | −25.4 | −19.9 | −22.5 |

TABLE 11

Vascular Engorgement

Mean Score

| Timepoint | 0.3% Test Article | 1% Test Article | Vehicle |
|---|---|---|---|
| Baseline | 2.3 | 2.3 | 2.3 |
| Day 15 | 1.8 | 2 | 1.9 |
| Day 29 | 1.7 | 1.7 | 1.8 |
| Day 57 | 1.6 | 1.6 | 1.6 |
| Day 85 | 1.4 | 1.5 | 1.5 |
| Day 113 | 1.3 | 1.4 | 1.5 |

TABLE 12

Vascular Engorgement

Mean Change From Baseline

| Timepoint | 0.3% Test Article | 1% Test Article | Vehicle |
|---|---|---|---|
| Baseline | 0 | 0 | 0 |
| Day 15 | −0.5 | −0.3 | −0.4 |
| Day 29 | −0.7 | −0.6 | −0.5 |
| Day 57 | −0.8 | −0.7 | −0.7 |
| Day 85 | −0.9 | −0.8 | −0.7 |
| Day 113 | −1 | −0.8 | −0.8 |

TABLE 13

Tarsal Conjunctival Erythema

Mean Score

| Timepoint | 0.3% Test Article | 1% Test Article | Vehicle |
|---|---|---|---|
| Baseline | 2.2 | 2.3 | 2.2 |
| Day 15 | 1.9 | 2 | 2 |
| Day 29 | 1.8 | 1.8 | 1.8 |
| Day 57 | 1.7 | 1.7 | 1.6 |
| Day 85 | 1.5 | 1.7 | 1.5 |
| Day 113 | 1.4 | 1.5 | 1.4 |

TABLE 14

Tarsal Conjunctival Erythema

Mean Change From Baseline

| Timepoint | 0.3% Test Article | 1% Test Article | Vehicle |
|---|---|---|---|
| Baseline | 0 | 0 | 0 |
| Day 15 | −0.3 | −0.2 | −0.2 |
| Day 29 | −0.4 | −0.5 | −0.4 |
| Day 57 | −0.5 | −0.5 | −0.6 |
| Day 85 | −0.8 | −0.6 | −0.7 |
| Day 113 | −0.8 | −0.7 | −0.9 |

TABLE 15

Total FCS

Mean Score

| Timepoint | 0.3% Test Article | 1% Test Article | Vehicle |
|---|---|---|---|
| Baseline | 6 | 6.2 | 5.9 |
| Day 15 | 4.5 | 4.9 | 4.7 |
| Day 29 | 4.3 | 4.4 | 4.2 |
| Day 57 | 4 | 4 | 4.1 |
| Day 85 | 3.7 | 4.3 | 3.8 |
| Day 113 | 3.5 | 3.4 | 3.5 |

TABLE 16

Total FCS

Mean Change From Baseline

| Timepoint | 0.3% Test Article | 1% Test Article | Vehicle |
|---|---|---|---|
| Baseline | 0 | 0 | 0 |
| Day 15 | −1.5 | −1.3 | −1.2 |
| Day 29 | −1.8 | −1.9 | −1.4 |
| Day 57 | −2.2 | −2.3 | −1.7 |
| Day 85 | −2.4 | −2 | −2 |
| Day 113 | −2.6 | −2.9 | −2.4 |

TABLE 17

Inferior FCS

Mean Score

| Timepoint | 0.3% Test Article | 1% Test Article | Vehicle |
|---|---|---|---|
| Baseline | 1.9 | 2 | 1.9 |
| Day 15 | 1.6 | 1.8 | 1.6 |
| Day 29 | 1.5 | 1.6 | 1.5 |
| Day 57 | 1.4 | 1.5 | 1.5 |
| Day 85 | 1.4 | 1.5 | 1.5 |
| Day 113 | 1.3 | 1.2 | 1.4 |

TABLE 18

Inferior FCS

Mean Change From Baseline

| Timepoint | 0.3% Test Article | 1% Test Article | Vehicle |
|---|---|---|---|
| Baseline | 0 | 0 | 0 |
| Day 15 | −0.3 | −0.2 | −0.3 |
| Day 29 | −0.4 | −0.4 | −0.4 |
| Day 57 | −0.5 | −0.5 | −0.4 |
| Day 85 | −0.5 | −0.5 | −0.4 |
| Day 113 | −0.6 | −0.8 | −0.5 |

TABLE 19

Combined FCS

Mean Score

| Timepoint | 0.3% Test Article | 1% Test Article | Vehicle |
|---|---|---|---|
| Baseline | 4.3 | 4.5 | 4.3 |
| Day 15 | 3.3 | 3.6 | 3.5 |
| Day 29 | 3.1 | 3.2 | 3.1 |
| Day 57 | 2.9 | 2.9 | 3.1 |
| Day 85 | 2.7 | 3.1 | 2.8 |
| Day 113 | 2.4 | 2.5 | 2.5 |

TABLE 20

Combined FCS

Mean Change From Baseline

| Timepoint | 0.3% Test Article | 1% Test Article | Vehicle |
|---|---|---|---|
| Baseline | 0 | 0 | 0 |
| Day 15 | −1 | −0.9 | −0.8 |
| Day 29 | −1.2 | −1.3 | −1.2 |
| Day 57 | −1.4 | −1.6 | −1.2 |
| Day 85 | −1.6 | −1.4 | −1.5 |
| Day 113 | −1.9 | −2 | −1.8 |

TABLE 21

VAS Discomfort MMP9-Positive Subgroup

Mean VAS Score

| Timepoint | 0.3% Test Article | 1% Test Article | Vehicle |
|---|---|---|---|
| Baseline | 69 | 66.7 | 65.3 |
| Day 15 | 48.1 | 47.7 | 54.8 |
| Day 29 | 44.9 | 45 | 47.5 |
| Day 57 | 41.3 | 42.7 | 45.6 |
| Day 85 | 36 | 39.5 | 38.9 |
| Day 113 | 34.6 | 36.9 | 41.2 |

TABLE 22

VAS Discomfort MMP9-Positive Subgroup

Mean Percentage Change From Baseline

| Timepoint | 0.3% Test Article | 1% Test Article | Vehicle |
|---|---|---|---|
| Baseline | 0 | 0 | 0 |
| Day 15 | −30.29% | −28.49% | −16.08% |
| Day 29 | −34.93% | −32.53% | −27.26% |
| Day 57 | −40.14% | −35.98% | −30.17% |
| Day 85 | −47.83% | −40.78% | −40.43% |
| Day 113 | −49.86% | −44.68% | −36.91% |

TABLE 23

Vascular Engorgement MMP9-Positive Subgroup

Mean VAS Score

| Timepoint | 0.3% Test Article | 1% Test Article | Vehicle |
|---|---|---|---|
| Baseline | 2.3 | 2.3 | 2.3 |
| Day 15 | 1.8 | 2 | 1.9 |
| Day 29 | 1.7 | 1.8 | 1.8 |
| Day 57 | 1.6 | 1.6 | 1.6 |
| Day 85 | 1.5 | 1.5 | 1.5 |
| Day 113 | 1.4 | 1.5 | 1.5 |

TABLE 24

Vascular Engorgement MMP9-Positive Subgroup

Mean Percent Change From Baseline

| Timepoint | 0.3% Test Article | 1% Test Article | Vehicle |
|---|---|---|---|
| Baseline | 0 | 0 | 0 |
| Day 15 | −21.74% | −13.04% | −17.39% |
| Day 29 | −26.09% | −21.74% | −21.74% |
| Day 57 | −30.43% | −30.43% | −30.43% |
| Day 85 | −34.78% | −34.78% | −34.78% |
| Day 113 | −39.13% | −34.78% | −34.78% |

TABLE 25

FCS Combined Score MMP9-Positive Subgroup

FCS Combined Score

| Timepoint | 0.3% Test Article | 1% Test Article | Vehicle |
|---|---|---|---|
| Baseline | 4.3 | 4.4 | 4.2 |
| Day 15 | 3.3 | 3.5 | 3.4 |
| Day 29 | 3.1 | 3.3 | 3.2 |
| Day 57 | 2.9 | 2.9 | 3.4 |
| Day 85 | 2.7 | 2.9 | 3 |
| Day 113 | 2.3 | 2.3 | 2.6 |

TABLE 26

FCS Combined Score MMP9-Positive Subgroup

Mean Percent Change from Baseline

| Timepoint | 0.3% Test Article | 1% Test Article | Vehicle |
|---|---|---|---|
| Baseline | 0 | 0 | 0 |
| Day 15 | −23.26% | −20.45% | −19.05% |
| Day 29 | −27.91% | −25.00% | −23.81% |
| Day 57 | −32.56% | −34.09% | −19.05% |
| Day 85 | −37.21% | −34.09% | −28.57% |
| Day 113 | −46.51% | −47.73% | −38.10% |

TABLE 27

FCS Inferior Score MMP9-Positive Subgroup

FCS Inferior Score

| Timepoint | 0.3% Test Article | 1% Test Article | Vehicle |
|---|---|---|---|
| Baseline | 1.9 | 1.9 | 1.8 |
| Day 15 | 1.7 | 1.6 | 1.6 |
| Day 29 | 1.5 | 1.6 | 1.6 |
| Day 57 | 1.4 | 1.4 | 1.7 |
| Day 85 | 1.4 | 1.5 | 1.5 |
| Day 113 | 1.2 | 1.1 | 1.4 |

TABLE 28

FCS Inferior Score MMP9-Positive Subgroup

| | Mean Percent Change from Baseline | | |
|---|---|---|---|
| Timepoint | 0.3% Test Article | 1% Test Article | Vehicle |
| Baseline | 0 | 0 | 0 |
| Day 15 | −10.53% | −15.79% | −11.11% |
| Day 29 | −21.05% | −15.79% | −11.11% |
| Day 57 | −26.32% | −26.32% | −5.56% |
| Day 85 | −26.32% | −21.05% | −16.67% |
| Day 113 | −36.84% | −42.11% | −22.22% |

TABLE 29

Outcome of MMP9 Point of Care Test (Quidel InflammaDry Test) Performed After 12 Weeks of Treatment in Subject Subgroup That Was MMP-9 Positive at Visit 1 at the Beginning of the Clinical Study

| | 0.3% Test Article | 1% Test Article | Vehicle |
|---|---|---|---|
| Positive MMP-9 Test Result After 12 Weeks of Treatment | 60% | 65% | 79% |
| Negative MMP-9 Test Result After 12 Weeks of Treatment | 40% | 35% | 21% |

Results in Table 29 are test results of a MMP-9 Point of Care Test (Quidel InflammaDry Test) on subjects that had a baseline positive test result in the MMP-9 Point of Care Test (Quidel InflammaDry Test) conducted on Visit 1 at the beginning of the clinical study. The results in Table 29 show that for the subset of subjects having a baseline positive test result in the MMP-9 Point of Care Test (Quidel InflammaDry Test) on Visit 1 at the beginning of the clinical study who then received 0.3% Test Article during the clinical study, 40% of those subjects tested negative in the MMP-9 Point of Care Test (Quidel InflammaDry Test) performed on the subject after the subject had received 12 weeks of treatment in the clinical study. Results in Table 29 show that a greater percentage of subjects converted to a negative test result in the MMP-9 Point of Care Test (Quidel InflammaDry Test) when 0.3% Test Article was administered compared to 1% Test Article or Vehicle.

Example 2—Efficacy Study for Treatment of Meibomian Gland Dysfunction by Minocycline Topical Suspension in Human Subjects A multi-center, Phase 3, double-masked, randomized, vehicle-control study is undertaken to study the efficacy and safety of minocycline topical suspension (Test Article) versus Vehicle administered twice daily for twelve weeks in subjects with a diagnosis of meibomian gland dysfunction.

In order to test the safety and efficacy of the minocycline topical suspension Test Article, 750 subjects are randomized into two groups: Test Article or Vehicle BID in a 1:1 ratio. After the screening assessment, Single-Masked Vehicle is administered BID for 2 weeks. Following this Single-Masked Run-In period, Double-Masked Investigational Product (IP) is administered BID to both eyes for 12 weeks. The Test Article and Vehicle correspond to those described in Example 1.

The safety endpoints of this study include (see Example 1 for additional details):
Adverse Event (AE) Monitoring
Best Corrected Visual Acuity (BCVA)
Slit Lamp Biomicroscopy and External Eye Exam
Intraocular Pressure (IOP) Measurement
Dilated Ophthalmoscopy
Follow-Up Assessment The primary efficacy endpoints of this study are evaluated using hierarchical statistical testing in the following sequence. (Note: the analysis is performed on the intent-to-treat (ITT) population):

1. Changes in Vascular Engorgement at the study eyelid margin as graded by the investigator at Week 12 (Visit 6) from Randomization/Baseline (Visit 2) in Test Article compared to Vehicle
2. Change in Eye Discomfort Visual Analogue Score (VAS) at Week 12 (Visit 6) from Randomization/Baseline (Visit 2) in Test Article compared to Vehicle The secondary efficacy endpoints of this study include (see Example 1 for additional details regarding specific testing procedures):

1. Change in Fluorescein Corneal Staining (FCS) total score (National Eye Institute [NEI]/Industry Workshop 0-15 scale) in the study eye at Week 4 (Visit 4), Week 8 (Visit 5), and Week 12 (Visit 6) from Randomization/Baseline (Visit 2).
2. Change in FCS inferior, nasal, and central combined score (NEI/Industry Workshop section 1, 4 and 5 with a 0-9 scale) in the study eye at Week 4 (Visit 4), Week 8 (Visit 5), and Week 12 (Visit 6) from Randomization/Baseline (Visit 2).
3. Change in FCS inferior score (NEI/Industry Workshop section 5 with a 0-3 scale) in the study eye at Week 4 (Visit 4), Week 8 (Visit 5), and Week 12 (Visit 6), from Randomization/Baseline (Visit 2).
4. Changes in Eye Discomfort VAS at Week 4 (Visit 4), Week 8 (Visit 5), and Week 12 (Visit 6), from Randomization/Baseline (Visit 2).
5. Changes in Investigator reported scores on objective signs of inflamed MGD including change from Randomization/Baseline (Visit 2) at each follow up visit for individual severity scores:
Vascular Engorgement of eyelid margin
Plugging of Meibomian Gland
Character of Meibomian Gland Secretion
Expressibility of the Meibomian Gland
6. Changes in Investigator reported scores on objective signs of MGD for Total Clinical Outcome Severity Score from Randomization/Baseline (Visit 2) defined as the sum of the four individual severity scores for the clinical signs of:
Plugging of Meibomian Gland
Character of Meibomian Gland Secretion
Vascular Engorgement of eyelid margin
Expressibility of the Meibomian Gland
7. Changes in Investigator reported scores on objective Conjunctival Tarsal Erythema change from Randomization/Baseline (Visit 2) at each follow up visit.
8. Changes in Tear Film Break-Up Time (TFBUT) from Randomization/Baseline (Visit 2) at each follow-up visit.
9. Changes in the following Dry Eye-related ocular symptoms at each follow-up visit:
VAS Scale Symptoms (other than eye discomfort):
Eye Dryness
Foreign Body Sensation
SANDE change in the square root of the product of the two questions at each timepoint compared to baseline and the change from baseline of each individual question within the SANDE
10. Number of symptom flares during the 12 weeks of treatment.
11. The change from baseline in the unanesthetized Schirmer score.

At Visit 1, individuals of any gender or any race are eligible for study participation if they:
1. Have provided written informed consent prior to any study procedures.
2. Are 18 years of age or above.
3. Have a clinical diagnosis of moderate to severe MGD and who meet the following criteria, in a qualifying eyelid, at both Visit 1 (Screening) and Visit 2 (Randomization) examinations:
   a. Clinical sign severity score of at least 2 (moderate) on vascular engorgement at the eyelid margin and
   b. Clinical sign severity score of at least 2 (moderate) on plugging of the meibomian glands.
   c. Eye Discomfort Symptom score of ≥40 using VAS (0-100 point scale)
4. Meet the following criteria, in a qualifying eye (same eye that qualifies for Inclusion #3), at both the Visit 1 (Screening) and Visit 2 (Randomization) examinations:
   a. Fluorescein corneal staining (FCS) total score ≥3 in the inferior, central, and nasal region combined score (NEI/Industry Workshop sections 1, 4 and 5 with 0-9 scale)
   b. Schirmer score of >7 mm without topical anesthesia
5. Are willing and able to follow instructions and can be present for the required study visits for the duration of the study.
6. Have a BCVA, using corrective lenses if necessary, in both eyes of at least +0.7 as assessed by Early Treatment of Diabetic Retinopathy Study (ETDRS) or modified ETDRS.
7. If female, are non-pregnant, non-lactating and women of childbearing potential (WOCBP) must be using an acceptable method of birth control [e.g., an Intrauterine Contraceptive Device (IUCD) with a failure rate of <1%, hormonal contraceptives, or a barrier method] for the duration of the study. If a female subject is currently abstinent, they must agree to use one of the acceptable methods of birth control before they become sexually active.

In order for subjects to be eligible at Visit 1 they may not:
1. Have presence of inflammation and/or active structural change in the iris or anterior chamber.
2. Have lid structural abnormalities such as entropion or ectropion.
3. In the eyelid that qualifies (based on Inclusion #3), have grade level 4 (Obstructed) on Character of Secretion of Meibomian Glands or grade level 4 (No glands are expressible) on the Expressibility of Meibomian Glands.
4. Subjects with ocular inflammatory conditions (e.g., conjunctivitis, keratitis, anterior blepharitis, etc.) not related to MGD.
5. Subjects who have FCS total score=15 or a score=3, in either eye, in the superior region NEI/Industry Workshop scale or subjects who have FCS with diffuse confluent staining, filaments or frank epithelial defects.
6. Have suspected ocular fungal, viral or bacterial infection.
7. Have had penetrating intraocular surgery in the past 90 days or require penetrating intraocular surgery during the study.
8. Have had ocular surface surgery within 12 months of Visit 1 (e.g., LASIK, refractive, pterygium removal).
9. Subjects who within the past 90 days have had cauterization of the punctum or changes to the status (insertion or removal) of punctal plug(s) before the Screening Visit.
10. Have used topical ocular or oral antibiotics within 30 days of the study or expect to use during the study.
11. Have used LipiFlow or hypochlorous acid spray within 30 days of the study or expect to use during the study.
12. If using inhaled or intranasal corticosteroids, unable to maintain a stable dose for the duration of the study.
13. Have ever used isotretinoin.
14. If using Omega-3 supplements, dose must be stable for 3 months prior to Visit 1 and for the duration of the study.
15. Have used topical cyclosporine within 30 days of the study or during the study.
16. Have used topical lifitegrast within 30 days of the study or during the study.
17. Have used systemic corticosteroids within 30 days prior to study entry or during study participation.
18. Have used topical ocular corticosteroids or ocular non-steroidal anti-inflammatory drugs (NSAIDs) within 30 days prior to study entry and during study participation.
19. Have used topical ocular antihistamine and/or mast cell stabilizers within 30 days prior to study entry or during study participation.
20. Are unable or unwilling to discontinue using any preserved or unpreserved topical ocular medications (including artificial tears) upon Screening and for the duration of the study.
21. Are unwilling to discontinue use of contact lenses during the study.
22. Are unwilling to discontinue use of cosmetic makeup applied to the eyelids or eye lashes at the Screening Visit and during the study. If makeup was used, it should be removed at least 12 hours prior to Visit 1.
23. Have a known hypersensitivity to minocycline, any other tetracycline antibiotic, or to any of the other ingredients in the investigational product.
24. Are unable or unwilling to withhold the use of eyelid scrubs or use of mechanical therapy during the study.
25. Have been diagnosed with glaucoma or are currently using any glaucoma medication.
26. Have a history of herpetic keratitis.
27. Have a concomitant ocular pathology other than condition under study assessed as potentially confounding by the investigator.
28. Have a serious systemic disease or uncontrolled medical condition that in the judgment of the investigator could confound study assessments or limit compliance.
29. Have been exposed to any investigational drug or investigational device within the preceding 30 days.
30. Are an employee of the site that is directly involved in the management, administration, or support of this study or be an immediate family member of the same.
31. Have trigger factors including conjunctivochalasis, allergic conjunctivitis, contact lens intolerance, trichiasis, epithelial basement membrane dystrophy, infectious keratitis or conjunctivitis.
32. Have a documented history of ocular allergies, which, in the judgment of the investigator, are likely to have an acute increase in severity due to the expected timing of the exposure to the allergen to which the subject is sensitive. Subjects sensitive to seasonal allergens that are not expected to be present during the study are permitted.

Example 3—Open Label Long Term Efficacy Study for Treatment of Meibomian Gland Dysfunction by Minocycline Topical Suspension in Human Subjects An open label study is undertaken to study the long term efficacy and safety of minocycline topical suspension (Test Article) administered twice daily for 9 months in subjects with a diagnosis of meibomian gland dysfunction.

In order to test the long term safety and efficacy of the minocycline topical suspension Test Article, 400 subjects are given Test Article to use twice daily for 9 months. The subjects will be evaluated for safety and efficacy monthly for the duration of the trial. The Test Article and Vehicle correspond to those described in Example 1.

The safety endpoints of this study include (see Example 1 for additional details):
  Adverse Event (AE) Monitoring
  Best Corrected Visual Acuity (BCVA)
  Slit Lamp Biomicroscopy and External Eye Exam
  Intraocular Pressure (IOP) Measurement
  Dilated Ophthalmoscopy
  Follow-Up Assessment The primary efficacy endpoints of this study are evaluated using hierarchical statistical testing in the following sequence. (Note: the analysis is performed on the intent-to-treat (ITT) population):
  1. Changes in Vascular Engorgement at the study eyelid margin as graded by the investigator at Month 9 from Baseline in Test Article compared to Vehicle.
  2. Change in Eye Discomfort Visual Analogue Score (VAS) at Month 9 from Baseline in Test Article compared to Vehicle.

The secondary efficacy endpoints of this study include (see Example 1 for additional details regarding specific testing procedures):
  1. Change in Fluorescein Corneal Staining (FCS) total score (National Eye Institute [NEI]/Industry Workshop 0-15 scale) in the study eye at each visit from Baseline.
  2. Change in FCS inferior, nasal, and central combined score (NEI/Industry Workshop section 1, 4 and 5 with a 0-9 scale) in the study eye at each visit from Baseline.
  3. Change in FCS inferior score (NEI/Industry Workshop section 5 with a 0-3 scale) in the study eye at each visit from Baseline.
  4. Changes in Eye Discomfort VAS at each visit from Baseline.
  5. Changes in Investigator reported scores on objective signs of inflamed MGD including change from Baseline at each follow up visit for individual severity scores:
    Vascular Engorgement of eyelid margin
    Plugging of Meibomian Gland
    Character of Meibomian Gland Secretion
    Expressibility of the Meibomian Gland.
  6. Changes in Investigator reported scores on objective signs of MGD for Total Clinical Outcome Severity Score from Baseline defined as the sum of the four individual severity scores for the clinical signs of:
    Plugging of Meibomian Gland
    Character of Meibomian Gland Secretion
    Vascular Engorgement of eyelid margin
    Expressibility of the Meibomian Gland.
  7. Changes in Investigator reported scores on objective Conjunctival Tarsal Erythema change from Baseline at each follow up visit.
  8. Changes in Tear Film Break-Up Time (TFBUT) from Baseline at each follow-up visit.
  9. Changes in the following Dry Eye-related ocular symptoms at each follow-up visit:
    VAS Scale Symptoms (other than eye discomfort):
      Eye Dryness
      Foreign Body Sensation
    SANDE change in the square root of the product of the two questions at each timepoint compared to baseline and the change from baseline of each individual question within the SANDE
  10. Number of symptom flares during the 12 weeks of treatment.
  11. The change from baseline in the unanesthetized Schirmer score.

At Visit 1, individuals of any gender or any race are eligible for study participation if they:
  1. Have provided written informed consent prior to any study procedures.
  2. Are 18 years of age or above.
  3. Have met the criteria for inclusion and successfully completed the phase 3 trial described in Example 2.
  4. Did not have worsening of VAS symptom or eyelid vascularity over the course of the phase 3 trial described in Example 2.

Example 4—Pharmacokinetic Profile Study for Treatment of Meibomian Gland Dysfunction by Minocycline Topical Suspension in Human Subjects An open label, multiple dose study is undertaken to assess the pharmacokinetic profile of minocycline topical suspension (Test Article) in subjects with a diagnosis of meibomian gland dysfunction.

In order to test the pharmacokinetic profile of the minocycline topical suspension Test Article, 20 subjects are given Test Article to use twice daily for 4 weeks. On days 1, 2, 3, 7, 9, 14, 21, and 28 blood will be drawn for pharmacokinetic analysis. End of study follow up will take place 7-10 days following cessation of treatment. Adverse events, vital signs, physical exam, and subject symptoms will be recorded at each visit. The Test Article and Vehicle correspond to those described in Example 1.

The safety endpoints of this study include (see Example 1 for additional details):
  Adverse Event (AE) Monitoring
  Best Corrected Visual Acuity (BCVA)
  Slit Lamp Biomicroscopy and External Eye Exam
  Intraocular Pressure (IOP) Measurement
  Dilated Ophthalmoscopy
  Follow-Up Assessment The primary efficacy endpoints of this study include:
  1. The maximal plasma concentration of minocycline (Cmax)
  2. The time to maximal plasma minocycline concentration (Tmax)
  3. The exposure over 4 weeks of treatment to minocycline by evaluating the area under the curve (AUC).
  4. The half life of plasma minocycline At Visit 1, individuals of any gender or any race are eligible for study participation if they:
1. Have provided written informed consent prior to any study procedures.
2. Are 18 years of age or above.
3. Have a clinical diagnosis of moderate to severe MGD and who meet the following criteria, in a qualifying eyelid, at both Visit 1 examinations:
   a. Clinical sign severity score of at least 2 (moderate) on vascular engorgement at the eyelid margin and
   b. Clinical sign severity score of at least 2 (moderate) on plugging of the meibomian glands.
   c. Eye Discomfort Symptom score of ≥40 using VAS (0-100 point scale)
4. Are willing and able to follow instructions and can be present for the required study visits for the duration of the study.
5. Have a BCVA, using corrective lenses if necessary, in both eyes of at least +0.7 as assessed by Early Treatment of Diabetic Retinopathy Study (ETDRS) or modified ETDRS.
6. If female, are non-pregnant, non-lactating and women of childbearing potential (WOCBP) must be using an acceptable method of birth control [e.g., an Intrauterine Contraceptive Device (IUCD) with a failure rate of <1%, hormonal contraceptives, or a barrier method] for the duration of the study. If a female subject is currently abstinent, they must agree to use one of the acceptable methods of birth control before they become sexually active.
7. Have a negative HIV, Hepatitis B, and Hepatitis C serology at screening.
8. No significant abnormalities in hematology, blood chemistry, or urinalysis at screening.
9. Body mass index (BMI) 19-30 kg/m2
10. Otherwise healthy subjects In order for subjects to be eligible at Visit 1 they may not be in violation of any of the exclusion criteria described in Example 2.

Example 5—Comparative Dosing Frequency Study for Treatment of Meibomian Gland Dysfunction by Minocycline Topical Suspension in Human Subjects A multi-center, double-masked, randomized, vehicle-controlled study of the noninferiority of once daily administration of minocycline topical suspension (Test Article), as compared to twice daily administration is undertaken to assess the optimal dosing regimen to treat subjects with a diagnosis of meibomian gland dysfunction.

In order to evaluate the noninferiority of efficacy and safety of Test Article administration twice daily versus once daily for twelve weeks, subjects will be randomized into two groups: Test Article administered twice daily (BID) or Test Article administered once daily in a 1:1 ratio. After the screening assessment, Single-Masked Vehicle will be administered for 2 weeks. Following this Single-Masked Run-In period, Double-Masked Investigational Product (IP) will be administered to both eyes for 12 weeks. The Test Article and Vehicle correspond to those described in Example 1.

The safety end points, primary efficacy endpoints, inclusion criteria and exclusion criteria are the same as those noted in Example 2.

Example 6—Preparation of Minocycline Topical Suspension

A minocycline topical suspension was prepared according to the experimental procedures described below.

Particles of minocycline crystalline Form II (having a D90 particle size less than 5 microns, in an amount sufficient to result in the final minocycline topical suspension containing 1% (w/w) minocycline) were added to mineral oil (the amount of mineral oil corresponded to 29.7% (w/w) of the final minocycline topical suspension, and the mineral oil was Mineral Oil USP having a specific gravity in the range of 0.845 to 0.905 and a viscosity greater than 34.5 centistokes when the viscosity is measured at 40° C.) and the resulting mixture was stirred for about 30 minutes at room temperature. To the resulting mixture was added the polymeric hydrocarbon gelling agent commercially available under the tradename VERSAGEL® M-750 (in an amount corresponding to 69.3% (w/w) of the final minocycline topical suspension) and the mixture was stirred for about one hour at room temperature. Samples from different parts of the mixing vessel were analyzed by HPLC to determine content homogeneity. The mixture was then dispensed, filled in aluminum tubes, and terminally sterilized to provide tubes of the minocycline topical suspension containing 1% (w/w) minocycline. Composition of the 1% (w/w) minocycline topical suspension is set forth in the table below.

| Component | Amount | Function |
| --- | --- | --- |
| Minocycline base | 1% w/w | active ingredient |
| Polymeric hydrocarbon gelling agent commercially available under the tradename VERSAGEL ® M-750 | 69.3% w/w | gelling agent |
| Mineral oil | 29.7% w/w | wetting agent |

Particles of minocycline crystalline Form II having a D90 particle size less than 5 microns were obtained by controlled jet-milling micronization of minocycline crystalline Form II. The polymeric hydrocarbon gelling agent commercially available under the tradename VERSAGEL® M-750 is a mixture of ethylene-propylene-styrene copolymer, butylene-ethylene-styrene copolymer, butylated-hydroxytoluene, and mineral oil. The ethylene-propylene-styrene copolymer (e.g., weight-average molecular weight of about 200,000 g/mol) is present in an amount within the range of 2.5% to 10% (w/w), the butylene-ethylene-styrene copolymer (e.g., weight-average molecular weight of about 100,000 g/mol) is present in an amount within the range of 0.1% to 2.5% (w/w), the butylated-hydroxytoluene is present in an amount <0.5% (w/w), and the remainder is mineral oil (e.g., having a weight-average molecular weight in the range of 230-700 g/mol).

Example 7—Rheological Evaluation of Minocycline Topical Suspensions

Minocycline topical suspensions were subjected to rheological evaluation. Experimental procedures and results are described below.

Part I—Experimental Procedures

The following rheological tests were conducted on a sample of the 0.3% Test Article and 1% Test Article described in Tables 30 and 31 below: Shear Rate Sweep, Sear Stress Sweep, and Oscillation Stress Sweep.

TABLE 30

Composition of 0.3% Test Article

| Component | Amount | Function |
|---|---|---|
| Minocycline base | 0.3% w/w | active ingredient |
| Polymeric hydrocarbon gelling agent commercially available under the tradename VERSAGEL ® M–750 | 69.8% w/w | gelling agent |
| Mineral oil | 29.9% w/w | wetting agent |

TABLE 31

Composition of 1% Test Article

| Component | Amount | Function |
|---|---|---|
| Minocycline base | 1% w/w | active ingredient |
| Polymeric hydrocarbon gelling agent commercially available under the tradename VERSAGEL ® M–750 | 69.3% w/w | gelling agent |
| Mineral oil | 29.7% w/w | wetting agent |

The minocycline base was minocycline base in crystalline Form II. The polymeric hydrocarbon gelling agent commercially available under the tradename VERSAGEL® M-750 is a mixture of ethylene-propylene-styrene copolymer, butylene-ethylene-styrene copolymer, butylated-hydroxytoluene, and mineral oil. The ethylene-propylene-styrene copolymer (e.g., weight-average molecular weight of about 200,000 g/mol) is present in an amount within the range of 2.5% to 10% (w/w), the butylene-ethylene-styrene copolymer (e.g., weight-average molecular weight of about 100,000 g/mol) is present in an amount within the range of 0.1% to 2.5% (w/w), the butylated-hydroxytoluene is present in an amount <0.5% (w/w), and the remainder is mineral oil (e.g., having a weight-average molecular weight in the range of 230-700 g/mol).

Shear Rate Sweep

The Shear Rate Sweep analysis was performed as follows: following a 30 s equilibration time at 34° C., the sample was exposed to a 30 s pre-shear at a rate of 1 $s^{-1}$ before leading directly into a shear rate sweep, 1.0 $s^{-14}$ to 1000 $s^{-1}$, logarithmically scaled, 6 points per decade of shear rate, shear applied for 30 s at each rate with viscosity calculated over the final 5 seconds of each step.

Shear Stress Sweep

The Shear Stress Sweep analysis was performed as follows: following a 60 s equilibration time at 25° C., the sample was subjected to a shear stress sweep from 0.1 Pa to 100 Pa, logarithmically spaced, 8 points per decade of shear stress. Steady-state sensing was employed to ensure individual viscosity readings reached an acceptable degree of elastic or thixotropic equilibrium before being recorded. At each step of the test, viscosity was monitored every 5 seconds. Viscosity was recorded only when 3 successive measurements were within 5% of each other. A 60 s timeout was set: if an equilibrium viscosity was not achieved after that time the viscosity at that instant was recorded regardless of degree of equilibrium.

Oscillation Stress Sweep

The Oscillation Stress Sweep analysis was performed as follows: following a 60 s equilibration time at 25° C., the sample was exposed to an oscillatory stress sweep ranging from 0.1 Pa to 1000 Pa, 10 points per decade, at 1 Hz oscillation frequency. A step termination was set such that if at any point the oscillation strain exceeded 1500%, the test would immediately end.

Part I—Results

Results of the rheological tests are depicted in Tables 32-35 below along with FIGS. 17-21.

TABLE 32

CONTROLLED RATE VISCOSITY DATA

| | Viscosity at 1 $s^{-1}$ (Pa · s) | | | Viscosity at 1000 $s^{-1}$ (Pa · s) | | |
|---|---|---|---|---|---|---|
| Sample | Run 1 | Run 2 | Mean | Run 1 | Run 2 | Mean |
| 0.3% Test Article | 31.7 | 29.1 | 30.4 | 0.659 | 0.777 | 0.718 |
| 1% Test Article | 30.7 | 30.2 | 30.5 | 0.796 | 0.700 | 0.748 |

TABLE 33

ZERO SHEAR VISCOSITY – QUANTIFIED AS THE AVERAGE OF THE OBSERVED PLATEAU

| | Zero Shear Viscosity (Pa · s) | | |
|---|---|---|---|
| Sample | Run 1 | Run 2 | Mean |
| 0.3% Test Article | 303 | 286 | 295 |
| 1% Test Article | 322 | 334 | 328 |

TABLE 34

OSCILLATION STRESS SWEEP DATA

| | Complex Modulus Plateau (Pa) | | | Phase Angle Plateau (°) | | |
|---|---|---|---|---|---|---|
| Sample | Run 1 | Run 2 | Mean | Run 1 | Run 2 | Mean |
| 0.3% Test Article | 140 | 138 | 139 | 26.2 | 25.9 | 26.1 |
| 1% Test Article | 143 | 136 | 140 | 25.9 | 25.5 | 25.7 |

TABLE 35

OSCILLATION STRESS SWEEP ADDITIONAL DATA

| | Yield Stress (Pa) | | |
|---|---|---|---|
| Sample | Run 1 | Run 2 | Mean |
| 0.3% Test Article | 21.1 | 20.5 | 20.8 |
| 1% Test Article | 20.6 | 21.8 | 21.2 |

The results demonstrate a clear soft solid structure present under low stress conditions, yielding to non-Newtonian shear thinning flow as the applied stress is increased past a certain yielding stress. The 0.3% Test Article has slightly lower viscosity under zero shear conditions than the 1% Test Article.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating meibomian gland dysfunction, comprising topically administering to the eyelid margin of a patient in need thereof twice per day a dose of a minocycline topical suspension to treat the meibomian gland dysfunction, wherein the dose provides from about 0.1 mg to about 0.3 mg or about 0.3 mg to about 0.7 mg of minocycline, and the minocycline topical suspension comprises:
   a) minocycline in a suspended form within the topical suspension;
   b) a liquid medium that dissolves less than 5% (w/w) of the minocycline at room temperature after two hours, wherein the liquid medium contains mineral oil; and
   c) a polymeric hydrocarbon gelling agent;
   wherein particles of minocycline in the topical suspension have a D90 particle size less than 8 microns, and the topical suspension comprises about 0.3% (w/w) minocycline.

2. The method of claim 1, wherein the dose of minocycline topical suspension provides from about 0.1 mg to about 0.2 mg of minocycline.

3. The method of claim 2, wherein the topical suspension comprises 0.3% (w/w) minocycline.

4. The method of claim 3, wherein an amount of about 50 µL of the minocycline topical suspension is topically administered to the eyelid margin of the patient.

5. The method of claim 3, wherein the minocycline topical suspension is topically administered to the eyelid margin of the patient to form a strip having a width less than or equal to one-quarter inches.

6. The method of claim 3, wherein the minocycline topical suspension is topically administered across the full margin of the eyelid.

7. The method of claim 3, wherein the first dose of minocycline topical suspension is administered in the morning and the second dose of minocycline topical suspension is administered in the evening.

8. The method of claim 3, wherein the polymeric hydrocarbon gelling agent comprises from about 2.5% (w/w) to about 10% (w/w) of ethylene-propylene-styrene copolymer, and the ethylene-propylene-styrene copolymer has a weight-average molecular weight in the range of from about 150,000 g/mol to about 250,000 g/mol.

9. The method of claim 8, wherein the polymeric hydrocarbon gelling agent comprises from about 0.1% (w/w) to about 2.5% (w/w) of butylene-ethylene-styrene copolymer, and the butylene-ethylene-styrene copolymer has a weight-average molecular weight in the range of from about 50,000 g/mol to about 150,000 g/mol.

10. The method of claim 9, wherein the polymeric hydrocarbon gelling agent comprises at least about 80% (w/w) mineral oil.

11. The method of claim 10, wherein the minocycline topical suspension comprises from about 67% (w/w) to about 71% (w/w) of the polymeric hydrocarbon gelling agent.

12. The method of claim 11, wherein the minocycline topical suspension comprises from about 28% (w/w) to about 32% (w/w) of the liquid medium that dissolves less than 5% (w/w) of the minocycline at room temperature after two hours, wherein the liquid medium contains mineral oil.

13. The method of claim 12, wherein the liquid medium that dissolves less than 5% (w/w) of the minocycline at room temperature after two hours comprises at least 90% (w/w) mineral oil.

14. The method of claim 1, wherein the dose of minocycline topical suspension provides about 0.15 mg of minocycline.

15. The method of claim 1, wherein the dose of minocycline topical suspension provides from about 0.45 mg to about 0.55 mg of minocycline.

16. The method of claim 1, wherein the dose of minocycline topical suspension provides about 0.5 mg of minocycline.

17. The method of claim 1, wherein an amount of from about 45 µL to about 55 µL of the minocycline topical suspension is topically administered to the eyelid margin of the patient.

18. The method of claim 1, wherein the patient has an inflamed meibomian gland.

19. The method of claim 1, wherein maximum blood plasma concentration of minocycline does not exceed 3 µg/mL.

20. The method of claim 1, wherein the AUC of minocycline determined from monitoring blood plasma amounts of minocycline does not exceed 46 hiig/mL.

21. The method of claim 1, wherein the polymeric hydrocarbon gelling agent comprises an ethylene-propylene-styrene copolymer and a butylene-ethylene-styrene copolymer.

22. The method of claim 1, wherein the method produces at least a 35 percent reduction in the patient's Eye Discomfort Visual Analog Score.

* * * * *